US012624119B2

(12) United States Patent　　　　(10) Patent No.:　US 12,624,119 B2
Zhang et al.　　　　　　　　　　　(45) Date of Patent:　　May 12, 2026

(54) ISOLATED ANTIGEN-BINDING PROTEIN AND APPLICATION THEREOF

(71) Applicant: SHIHUIDA PHARMACEUTICAL GROUP (JILIN) CO., LTD., Baishan City (CN)

(72) Inventors: Xin Zhang, Suzhou (CN); Ting Xu, Suzhou (CN); Hui Ma, Suzhou (CN); Yangyang Yuan, Suzhou (CN); Shanshan Ning, Suzhou (CN); Shilong Fu, Suzhou (CN); Xiaolong Pan, Suzhou (CN); Liyao Zhou, Suzhou (CN); Meng Zhao, Suzhou (CN); Erxia Shi, Suzhou (CN)

(73) Assignee: SHIHUDA PHARMACEUTICAL GROUP (JILIN) CO., LTD., Baishan City (CN)

( * ) Notice: Subject to any disclaimer, the term of this patent is extended or adjusted under 35 U.S.C. 154(b) by 977 days.

(21) Appl. No.: 17/626,955

(22) PCT Filed: Jul. 16, 2020

(86) PCT No.: PCT/CN2020/102472
§ 371 (c)(1),
(2) Date: Jan. 13, 2022

(87) PCT Pub. No.: WO2021/008590
PCT Pub. Date: Jan. 21, 2021

(65) Prior Publication Data
US 2022/0356259 A1　　Nov. 10, 2022

(30) Foreign Application Priority Data
Jul. 17, 2019　(CN) .......................... 201910646093.8

(51) Int. Cl.
*C07K 16/28*　　　(2006.01)
*A61K 39/00*　　　(2006.01)

(52) U.S. Cl.
CPC .......... *C07K 16/2878* (2013.01); *A61K 39/00* (2013.01); *C07K 2317/92* (2013.01)

(58) Field of Classification Search
None
See application file for complete search history.

(56) References Cited

U.S. PATENT DOCUMENTS

2017/0260282 A1　9/2017　Holland et al.

FOREIGN PATENT DOCUMENTS

| CN | 105829343 | A | 8/2016 |
| CN | 106459203 | A | 2/2017 |
| WO | 2007133822 | A1 | 11/2007 |
| WO | 2013039954 | A1 | 3/2013 |

OTHER PUBLICATIONS

PCT/CN2020/102472 International Search Report dated Oct. 20, 2020.
Sukumar, S., et al., Characterization of MK-4166, a Clinical Agonistic Antibody that Targets human GITR and Inhibits the Generation and Suppressive Effects of T Regulatory Cells, Cancer Research, vol. 77, No. 16, Jun. 13, 2017, pp. 4378-4388.
Zhu, L.X., et al., GITR Agonist enhances Vaccination Responses in Lung Cancer, OncoImmunology, vol. 4, No. 4, Apr. 30, 2015, article No. e992237.

*Primary Examiner* — Daniel E Kolker
*Assistant Examiner* — Cheom-Gil Cheong
(74) *Attorney, Agent, or Firm* — Sughrue Mion, PLLC

(57)　　　ABSTRACT

An isolated antigen-binding protein, having one or more of the following properties: 1) capable of binding to human and monkey-derived GITR proteins at a $K_D$ value of $7 \times 10^{-12}$ or below, wherein the $K_D$ value is measured by BLI method; 2) capable of stimulating immune cell proliferation; 3) capable of stimulating immune cells to secrete IFN-γ, wherein the secretion is measured in T cell viability assay; 4) capable of inhibiting tumor growth and/or tumor cell proliferation; 5) capable of activating GITR signaling pathway; 6) capable of inhibiting the binding of GITR to GITRL.

17 Claims, 10 Drawing Sheets

Specification includes a Sequence Listing.

Concentration

Concentration

SEQUENCE LISTING

```
<160> NUMBER OF SEQ ID NOS: 77

<210> SEQ ID NO 1
<211> LENGTH: 120
<212> TYPE: PRT
<213> ORGANISM: Artificial Sequence
<220> FEATURE:
<223> OTHER INFORMATION: 3E2VH

<400> SEQUENCE: 1

Gln Val Gln Leu Gln Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Val Leu Ile Leu Trp Asn Asp Ile Lys Tyr Tyr Asn Pro Ala
    50                  55                  60

Leu Lys Ser Leu Leu Thr Val Ser Lys Asp Thr Ser Asn Asn Gln Val
65                  70                  75                  80

Phe Leu Lys Ile Ala Ser Val Asp Thr Ala Asp Thr Ala Thr Tyr Tyr
            85                  90                  95

Cys Ala Arg Val Asp Gly Tyr Tyr Gly Tyr Phe Asp Val Trp Gly Thr
            100                 105                 110

Gly Thr Thr Val Thr Val Ser Ser
        115                 120

<210> SEQ ID NO 2
<211> LENGTH: 7
<212> TYPE: PRT
<213> ORGANISM: Artificial Sequence
<220> FEATURE:
<223> OTHER INFORMATION: 3E2HCDR1

<400> SEQUENCE: 2

Thr Phe Gly Met Gly Val Gly
1               5

<210> SEQ ID NO 3
<211> LENGTH: 14
<212> TYPE: PRT
<213> ORGANISM: Artificial Sequence
<220> FEATURE:
<223> OTHER INFORMATION: 3E2HCDR2

<400> SEQUENCE: 3

Leu Trp Asn Asp Ile Lys Tyr Tyr Asn Pro Ala Leu Lys Ser
1               5                   10

<210> SEQ ID NO 4
<211> LENGTH: 10
<212> TYPE: PRT
<213> ORGANISM: Artificial Sequence
<220> FEATURE:
```

```
<223> OTHER INFORMATION: 3E2HCDR3

<400> SEQUENCE: 4

Val Asp Gly Tyr Tyr Gly Tyr Phe Asp Val
1               5                   10

<210> SEQ ID NO 5
<211> LENGTH: 30
<212> TYPE: PRT
<213> ORGANISM: Artificial Sequence
<220> FEATURE:
<223> OTHER INFORMATION: 3E2HFR1

<400> SEQUENCE: 5

Gln Val Gln Leu Gln Glu Ser Gly Pro Gly Ile Leu Gln Pro Ser Gln
1               5                   10                  15

Thr Leu Ser Leu Thr Cys Ser Phe Ser Gly Phe Ser Leu Ser
                20                  25                  30

<210> SEQ ID NO 6
<211> LENGTH: 16
<212> TYPE: PRT
<213> ORGANISM: Artificial Sequence
<220> FEATURE:
<223> OTHER INFORMATION: 3E2HFR2VHV2 H-FR2VHV3 H-FR2

<400> SEQUENCE: 6

Trp Ile Arg Gln Pro Ser Gly Lys Gly Leu Glu Trp Leu Val Leu Ile
1               5                   10                  15

<210> SEQ ID NO 7
<211> LENGTH: 32
<212> TYPE: PRT
<213> ORGANISM: Artificial Sequence
<220> FEATURE:
<223> OTHER INFORMATION: 3E2HFR3

<400> SEQUENCE: 7

Leu Leu Thr Val Ser Lys Asp Thr Ser Asn Asn Gln Val Phe Leu Lys
1               5                   10                  15

Ile Ala Ser Val Asp Thr Ala Asp Thr Ala Thr Tyr Tyr Cys Ala Arg
                20                  25                  30

<210> SEQ ID NO 8
<211> LENGTH: 11
<212> TYPE: PRT
<213> ORGANISM: Artificial Sequence
<220> FEATURE:
<223> OTHER INFORMATION: 3E2HFR4VHV3 H-FR4

<400> SEQUENCE: 8

Trp Gly Thr Gly Thr Thr Val Thr Val Ser Ser
1               5                   10

<210> SEQ ID NO 9
<211> LENGTH: 112
<212> TYPE: PRT
<213> ORGANISM: Artificial Sequence
<220> FEATURE:
<223> OTHER INFORMATION: 3E2VL

<400> SEQUENCE: 9

Asp Ile Val Met Thr Gln Ser Pro Leu Ser Leu Pro Val Ser Leu Gly
1               5                   10                  15
```

```
Asp Gln Ala Ser Ile Ser Cys Arg Ser Gln Thr Ile Val His Ser
        20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
        100                 105                 110
```

```
<210> SEQ ID NO 10
<211> LENGTH: 16
<212> TYPE: PRT
<213> ORGANISM: Artificial Sequence
<220> FEATURE:
<223> OTHER INFORMATION: 3E2LCDR1

<400> SEQUENCE: 10

Arg Ser Ser Gln Thr Ile Val His Ser Asn Gly Asn Thr Tyr Leu Glu
1               5                   10                  15
```

```
<210> SEQ ID NO 11
<211> LENGTH: 7
<212> TYPE: PRT
<213> ORGANISM: Artificial Sequence
<220> FEATURE:
<223> OTHER INFORMATION: 3E2LCDR2

<400> SEQUENCE: 11

Lys Val Ser Asn Arg Phe Ser
1               5
```

```
<210> SEQ ID NO 12
<211> LENGTH: 9
<212> TYPE: PRT
<213> ORGANISM: Artificial Sequence
<220> FEATURE:
<223> OTHER INFORMATION: 3E2LCDR3

<400> SEQUENCE: 12

Phe Gln Gly Ser His Val Pro Trp Thr
1               5
```

```
<210> SEQ ID NO 13
<211> LENGTH: 23
<212> TYPE: PRT
<213> ORGANISM: Artificial Sequence
<220> FEATURE:
<223> OTHER INFORMATION: 3E2LFR1

<400> SEQUENCE: 13

Asp Ile Val Met Thr Gln Ser Pro Leu Ser Leu Pro Val Ser Leu Gly
1               5                   10                  15

Asp Gln Ala Ser Ile Ser Cys
            20
```

```
<210> SEQ ID NO 14
<211> LENGTH: 15
<212> TYPE: PRT
<213> ORGANISM: Artificial Sequence
```

<220> FEATURE:
<223> OTHER INFORMATION: 3E2LFR2VLV3 L-FR2VLV4 L-FR2

<400> SEQUENCE: 14

Trp Tyr Leu Gln Lys Pro Gly Gln Ser Pro Lys Leu Leu Ile Tyr
1               5                   10                  15

<210> SEQ ID NO 15
<211> LENGTH: 32
<212> TYPE: PRT
<213> ORGANISM: Artificial Sequence
<220> FEATURE:
<223> OTHER INFORMATION: 3E2LFR3

<400> SEQUENCE: 15

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 16
<211> LENGTH: 10
<212> TYPE: PRT
<213> ORGANISM: Artificial Sequence
<220> FEATURE:
<223> OTHER INFORMATION: 3E2LFR4VLV3 L-FR4VLV4 L-FR4

<400> SEQUENCE: 16

Phe Gly Gly Gly Thr Lys Leu Glu Ile Lys
1               5                   10

<210> SEQ ID NO 17
<211> LENGTH: 120
<212> TYPE: PRT
<213> ORGANISM: Artificial Sequence
<220> FEATURE:
<223> OTHER INFORMATION: VHV1

<400> SEQUENCE: 17

Gln Val Thr Leu Gln Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Gly Met Gly Val Gly Trp Ile Arg Gln Pro Pro Gly Lys Gly Leu Glu
        35                  40                  45

Trp Leu Val Leu Ile Leu Trp Asn Asp Ile Lys Tyr Tyr Asn Pro Ala
    50                  55                  60

Leu Lys Ser Leu Leu Thr Val Thr Lys Asp Thr Ser Lys Asn Gln Val
65                  70                  75                  80

Val Leu Thr Ile Thr Asn Met Asp Pro Val Asp Thr Ala Thr Tyr Tyr
                85                  90                  95

Cys Ala Arg Val Asp Gly Tyr Tyr Gly Tyr Phe Asp Val Trp Gly Gln
            100                 105                 110

Gly Thr Met Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: VHV2

-continued

```
<400> SEQUENCE: 18

Gln Val Gln Leu Gln Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Gly Met Gly Val Gly Trp Ile Arg Gln Pro Ser Gly Lys Gly Leu Glu
            35                  40                  45

Trp Leu Val Leu Ile Leu Trp Asn Asp Ile Lys Tyr Tyr Asn Pro Ala
        50                  55                  60

Leu Lys Ser Leu Leu Thr Val Thr Lys Asp Thr Ser Lys Asn Gln Val
65                  70                  75                  80

Val Leu Thr Ile Thr Asn Met Asp Pro Val Asp Thr Ala Thr Tyr Tyr
                85                  90                  95

Cys Ala Arg Val Asp Gly Tyr Tyr Gly Tyr Phe Asp Val Trp Gly Gln
            100                 105                 110

Gly Thr Met Val Thr Val Ser Ser
            115                 120

<210> SEQ ID NO 19
<211> LENGTH: 120
<212> TYPE: PRT
<213> ORGANISM: Artificial Sequence
<220> FEATURE:
<223> OTHER INFORMATION: VHV3

<400> SEQUENCE: 19

Gln Val Gln Leu Gln Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Gly Met Gly Val Gly Trp Ile Arg Gln Pro Ser Gly Lys Gly Leu Glu
            35                  40                  45

Trp Leu Val Leu Ile Leu Trp Asn Asp Ile Lys Tyr Tyr Asn Pro Ala
        50                  55                  60

Leu Lys Ser Leu Leu Thr Val Thr Lys Asp Thr Ser Lys Asn Gln Val
65                  70                  75                  80

Val Leu Thr Ile Thr Asn Met Asp Pro Val Asp Thr Ala Thr Tyr Tyr
                85                  90                  95

Cys Ala Arg Val Asp Gly Tyr Tyr Gly Tyr Phe Asp Val Trp Gly Thr
            100                 105                 110

Gly Thr Thr Val Thr Val Ser Ser
            115                 120

<210> SEQ ID NO 20
<211> LENGTH: 112
<212> TYPE: PRT
<213> ORGANISM: Artificial Sequence
<220> FEATURE:
<223> OTHER INFORMATION: VLV2

<400> SEQUENCE: 20

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Thr Ile Val His Ser
            20                  25                  30

Asn Gly Asn Thr Tyr Leu Glu Trp Tyr Leu Gln Arg Pro Gly Gln Ser
            35                  40                  45
```

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: VLV3

<400> SEQUENCE: 21

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Thr Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 22
<211> LENGTH: 112
<212> TYPE: PRT
<213> ORGANISM: Artificial Sequence
<220> FEATURE:
<223> OTHER INFORMATION: VLV4

<400> SEQUENCE: 22

Asp Ile Val Met Thr Gln Ser Pro Leu Ser Leu Pro Val Thr Leu Gly
1               5                   10                  15

Asp Gln Ala Ser Ile Ser Cys Arg Ser Ser Gln Thr Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 23
<211> LENGTH: 120
<212> TYPE: PRT
<213> ORGANISM: Artificial Sequence
```

```
<220> FEATURE:
<223> OTHER INFORMATION: VH general formula3E2 VHVHV1~VHV3)
<220> FEATURE:
<221> NAME/KEY: X
<222> LOCATION: (3)..(3)
<223> OTHER INFORMATION: X is T or Q
<220> FEATURE:
<221> NAME/KEY: X
<222> LOCATION: (10)..(10)
<223> OTHER INFORMATION: X is G or T
<220> FEATURE:
<221> NAME/KEY: X
<222> LOCATION: (11)..(11)
<223> OTHER INFORMATION: X is I or L
<220> FEATURE:
<221> NAME/KEY: X
<222> LOCATION: (12)..(12)
<223> OTHER INFORMATION: X is L or V
<220> FEATURE:
<221> NAME/KEY: X
<222> LOCATION: (13)..(13)
<223> OTHER INFORMATION: X is Q or K
<220> FEATURE:
<221> NAME/KEY: X
<222> LOCATION: (15)..(15)
<223> OTHER INFORMATION: X is S or T
<220> FEATURE:
<221> NAME/KEY: X
<222> LOCATION: (19)..(19)
<223> OTHER INFORMATION: X is S or T
<220> FEATURE:
<221> NAME/KEY: X
<222> LOCATION: (23)..(23)
<223> OTHER INFORMATION: X is S or T
<220> FEATURE:
<221> NAME/KEY: X
<222> LOCATION: (43)..(43)
<223> OTHER INFORMATION: X is P or S
<220> FEATURE:
<221> NAME/KEY: X
<222> LOCATION: (72)..(72)
<223> OTHER INFORMATION: X is S or T
<220> FEATURE:
<221> NAME/KEY: X
<222> LOCATION: (77)..(77)
<223> OTHER INFORMATION: X is N or K
<220> FEATURE:
<221> NAME/KEY: X
<222> LOCATION: (81)..(81)
<223> OTHER INFORMATION: X is FV
<220> FEATURE:
<221> NAME/KEY: X
<222> LOCATION: (83)..(83)
<223> OTHER INFORMATION: X is K or T
<220> FEATURE:
<221> NAME/KEY: X
<222> LOCATION: (85)..(85)
<223> OTHER INFORMATION: X is A or T
<220> FEATURE:
<221> NAME/KEY: X
<222> LOCATION: (86)..(86)
<223> OTHER INFORMATION: X is S or N
<220> FEATURE:
<221> NAME/KEY: X
<222> LOCATION: (87)..(87)
<223> OTHER INFORMATION: X is V or M
<220> FEATURE:
<221> NAME/KEY: X
<222> LOCATION: (89)..(89)
<223> OTHER INFORMATION: X is T or P
<220> FEATURE:
<221> NAME/KEY: X
<222> LOCATION: (90)..(90)
<223> OTHER INFORMATION: X is A or V
<220> FEATURE:
<221> NAME/KEY: X
<222> LOCATION: (112)..(112)
<223> OTHER INFORMATION: X is Q or T
<220> FEATURE:
```

```
<221> NAME/KEY: X
<222> LOCATION: (115)..(115)
<223> OTHER INFORMATION: X is M or T

<400> SEQUENCE: 23

Gln Val Xaa Leu Gln Glu Ser Gly Pro Xaa Xaa Xaa Xaa Pro Xaa Gln
1               5                   10                  15

Thr Leu Xaa Leu Thr Cys Xaa Phe Ser Gly Phe Ser Leu Ser Thr Phe
            20                  25                  30

Gly Met Gly Val Gly Trp Ile Arg Gln Pro Xaa Gly Lys Gly Leu Glu
        35                  40                  45

Trp Leu Val Leu Ile Leu Trp Asn Asp Ile Lys Tyr Tyr Asn Pro Ala
    50                  55                  60

Leu Lys Ser Leu Leu Thr Val Xaa Lys Asp Thr Ser Xaa Asn Gln Val
65                  70                  75                  80

Xaa Leu Xaa Ile Xaa Xaa Xaa Asp Xaa Xaa Asp Thr Ala Thr Tyr Tyr
                85                  90                  95

Cys Ala Arg Val Asp Gly Tyr Tyr Gly Tyr Phe Asp Val Trp Gly Xaa
            100                 105                 110

Gly Thr Xaa Val Thr Val Ser Ser
        115                 120

<210> SEQ ID NO 24
<211> LENGTH: 112
<212> TYPE: PRT
<213> ORGANISM: Artificial Sequence
<220> FEATURE:
<223> OTHER INFORMATION: VL general formula3E2 VLVLV2~VLV4)
<220> FEATURE:
<221> NAME/KEY: X
<222> LOCATION: (14)..(14)
<223> OTHER INFORMATION: X is S or T
<220> FEATURE:
<221> NAME/KEY: X
<222> LOCATION: (17)..(17)
<223> OTHER INFORMATION: X is Q or D
<220> FEATURE:
<221> NAME/KEY: X
<222> LOCATION: (18)..(18)
<223> OTHER INFORMATION: X is P or Q
<220> FEATURE:
<221> NAME/KEY: X
<222> LOCATION: (44)..(44)
<223> OTHER INFORMATION: X is R or K
<220> FEATURE:
<221> NAME/KEY: X
<222> LOCATION: (88)..(88)
<223> OTHER INFORMATION: X is L or V
<220> FEATURE:
<221> NAME/KEY: X
<222> LOCATION: (109)..(109)
<223> OTHER INFORMATION: X is V or L

<400> SEQUENCE: 24

Asp Ile Val Met Thr Gln Ser Pro Leu Ser Leu Pro Val Xaa Leu Gly
1               5                   10                  15

Xaa Xaa Ala Ser Ile Ser Cys Arg Ser Ser Gln Thr Ile Val His Ser
            20                  25                  30

Asn Gly Asn Thr Tyr Leu Glu Trp Tyr Leu Gln Xaa Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

-continued

```
Ser Arg Val Glu Ala Glu Asp Xaa Gly Val Tyr Tyr Cys Phe Gln Gly
                85                  90                  95

Ser His Val Pro Trp Thr Phe Gly Gly Gly Thr Lys Xaa Glu Ile Lys
            100                 105                 110

<210> SEQ ID NO 25
<211> LENGTH: 30
<212> TYPE: PRT
<213> ORGANISM: Artificial Sequence
<220> FEATURE:
<223> OTHER INFORMATION: VHV1 H-FR1

<400> SEQUENCE: 25

Gln Val Thr Leu Gln Glu Ser Gly Pro Thr Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 26
<211> LENGTH: 16
<212> TYPE: PRT
<213> ORGANISM: Artificial Sequence
<220> FEATURE:
<223> OTHER INFORMATION: VHV1 H-FR2

<400> SEQUENCE: 26

Trp Ile Arg Gln Pro Pro Gly Lys Gly Leu Glu Trp Leu Val Leu Ile
1               5                   10                  15

<210> SEQ ID NO 27
<211> LENGTH: 32
<212> TYPE: PRT
<213> ORGANISM: Artificial Sequence
<220> FEATURE:
<223> OTHER INFORMATION: VHV1 H-FR3VHV2 H-FR3VHV3 H-FR3

<400> SEQUENCE: 27

Leu Leu Thr Val Thr Lys Asp Thr Ser Lys Asn Gln Val Val Leu Thr
1               5                   10                  15

Ile Thr Asn Met Asp Pro Val Asp Thr Ala Thr Tyr Tyr Cys Ala Arg
            20                  25                  30

<210> SEQ ID NO 28
<211> LENGTH: 11
<212> TYPE: PRT
<213> ORGANISM: Artificial Sequence
<220> FEATURE:
<223> OTHER INFORMATION: VHV1 H-FR4VHV2 H-FR4

<400> SEQUENCE: 28

Trp Gly Gln Gly Thr Met Val Thr Val Ser Ser
1               5                   10

<210> SEQ ID NO 29
<211> LENGTH: 30
<212> TYPE: PRT
<213> ORGANISM: Artificial Sequence
<220> FEATURE:
<223> OTHER INFORMATION: VHV2 H-FR1VHV3 H-FR1

<400> SEQUENCE: 29

Gln Val Gln Leu Gln Glu Ser Gly Pro Thr Leu Val Lys Pro Thr Gln
1               5                   10                  15

Thr Leu Thr Leu Thr Cys Thr Phe Ser Gly Phe Ser Leu Ser
            20                  25                  30
```

```
<210> SEQ ID NO 30
<211> LENGTH: 23
<212> TYPE: PRT
<213> ORGANISM: Artificial Sequence
<220> FEATURE:
<223> OTHER INFORMATION: VLV2 L-FR1VLV3 L-FR1

<400> SEQUENCE: 30

Asp Ile Val Met Thr Gln Ser Pro Leu Ser Leu Pro Val Thr Leu Gly
1               5                   10                  15

Gln Pro Ala Ser Ile Ser Cys
            20

<210> SEQ ID NO 31
<211> LENGTH: 15
<212> TYPE: PRT
<213> ORGANISM: Artificial Sequence
<220> FEATURE:
<223> OTHER INFORMATION: VLV2 L-FR2

<400> SEQUENCE: 31

Trp Tyr Leu Gln Arg Pro Gly Gln Ser Pro Lys Leu Leu Ile Tyr
1               5                   10                  15

<210> SEQ ID NO 32
<211> LENGTH: 32
<212> TYPE: PRT
<213> ORGANISM: Artificial Sequence
<220> FEATURE:
<223> OTHER INFORMATION: VLV2 L-FR3VLV3 L-FR3VLV4 L-FR3

<400> SEQUENCE: 32

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
                20                  25                  30

<210> SEQ ID NO 33
<211> LENGTH: 10
<212> TYPE: PRT
<213> ORGANISM: Artificial Sequence
<220> FEATURE:
<223> OTHER INFORMATION: VLV2 L-FR4

<400> SEQUENCE: 33

Phe Gly Gly Gly Thr Lys Val Glu Ile Lys
1               5                   10

<210> SEQ ID NO 34
<211> LENGTH: 23
<212> TYPE: PRT
<213> ORGANISM: Artificial Sequence
<220> FEATURE:
<223> OTHER INFORMATION: VLV4 L-FR1

<400> SEQUENCE: 34

Asp Ile Val Met Thr Gln Ser Pro Leu Ser Leu Pro Val Thr Leu Gly
1               5                   10                  15

Asp Gln Ala Ser Ile Ser Cys
            20

<210> SEQ ID NO 35
<211> LENGTH: 30
<212> TYPE: PRT
```

```
<213> ORGANISM: Artificial Sequence
<220> FEATURE:
<223> OTHER INFORMATION: H-FR1general formula3E2 H-FR1VHV1~VHV3 H-FR1)
<220> FEATURE:
<221> NAME/KEY: X
<222> LOCATION: (3)..(3)
<223> OTHER INFORMATION: X is T or Q
<220> FEATURE:
<221> NAME/KEY: X
<222> LOCATION: (10)..(10)
<223> OTHER INFORMATION: X is G or T
<220> FEATURE:
<221> NAME/KEY: X
<222> LOCATION: (11)..(11)
<223> OTHER INFORMATION: X is I or L
<220> FEATURE:
<221> NAME/KEY: X
<222> LOCATION: (12)..(12)
<223> OTHER INFORMATION: X is L or V
<220> FEATURE:
<221> NAME/KEY: X
<222> LOCATION: (13)..(13)
<223> OTHER INFORMATION: X is Q or K
<220> FEATURE:
<221> NAME/KEY: X
<222> LOCATION: (15)..(15)
<223> OTHER INFORMATION: X is S or T
<220> FEATURE:
<221> NAME/KEY: X
<222> LOCATION: (19)..(19)
<223> OTHER INFORMATION: X is S or T
<220> FEATURE:
<221> NAME/KEY: X
<222> LOCATION: (23)..(23)
<223> OTHER INFORMATION: X is S or T

<400> SEQUENCE: 35

Gln Val Xaa Leu Gln Glu Ser Gly Pro Xaa Xaa Xaa Xaa Pro Xaa Gln
1               5                   10                  15

Thr Leu Xaa Leu Thr Cys Xaa Phe Ser Gly Phe Ser Leu Ser
            20                  25                  30

<210> SEQ ID NO 36
<211> LENGTH: 16
<212> TYPE: PRT
<213> ORGANISM: Artificial Sequence
<220> FEATURE:
<223> OTHER INFORMATION: H-FR2 general formula3E2 H-FR2VHV1~VHV3 H-FR2)
<220> FEATURE:
<221> NAME/KEY: X
<222> LOCATION: (6)..(6)
<223> OTHER INFORMATION: X is P or S

<400> SEQUENCE: 36

Trp Ile Arg Gln Pro Xaa Gly Lys Gly Leu Glu Trp Leu Val Leu Ile
1               5                   10                  15

<210> SEQ ID NO 37
<211> LENGTH: 32
<212> TYPE: PRT
<213> ORGANISM: Artificial Sequence
<220> FEATURE:
<223> OTHER INFORMATION: H-FR3 general formula3E2 H-FR3VHV1~VHV3 H-FR3)
<220> FEATURE:
<221> NAME/KEY: X
<222> LOCATION: (5)..(5)
<223> OTHER INFORMATION: X is S or T
<220> FEATURE:
<221> NAME/KEY: X
<222> LOCATION: (10)..(10)
<223> OTHER INFORMATION: X is N or K
<220> FEATURE:
<221> NAME/KEY: X
<222> LOCATION: (14)..(14)
```

```
<223> OTHER INFORMATION: X is F or V
<220> FEATURE:
<221> NAME/KEY: X
<222> LOCATION: (16)..(16)
<223> OTHER INFORMATION: X is K or T
<220> FEATURE:
<221> NAME/KEY: X
<222> LOCATION: (18)..(18)
<223> OTHER INFORMATION: X is A or T
<220> FEATURE:
<221> NAME/KEY: X
<222> LOCATION: (19)..(19)
<223> OTHER INFORMATION: X is S or N
<220> FEATURE:
<221> NAME/KEY: X
<222> LOCATION: (20)..(20)
<223> OTHER INFORMATION: X is V or M
<220> FEATURE:
<221> NAME/KEY: X
<222> LOCATION: (22)..(22)
<223> OTHER INFORMATION: X is T or P
<220> FEATURE:
<221> NAME/KEY: X
<222> LOCATION: (23)..(23)
<223> OTHER INFORMATION: X is A or V

<400> SEQUENCE: 37

Leu Leu Thr Val Xaa Lys Asp Thr Ser Xaa Asn Gln Val Xaa Leu Xaa
1               5                   10                  15

Ile Xaa Xaa Xaa Asp Xaa Xaa Asp Thr Ala Thr Tyr Tyr Cys Ala Arg
            20                  25                  30

<210> SEQ ID NO 38
<211> LENGTH: 11
<212> TYPE: PRT
<213> ORGANISM: Artificial Sequence
<220> FEATURE:
<223> OTHER INFORMATION: H-FR4 general formula3E2 H-FR4VHV1~VHV3 H-FR4)
<220> FEATURE:
<221> NAME/KEY: X
<222> LOCATION: (3)..(3)
<223> OTHER INFORMATION: X is Q or T
<220> FEATURE:
<221> NAME/KEY: X
<222> LOCATION: (6)..(6)
<223> OTHER INFORMATION: X is M or T

<400> SEQUENCE: 38

Trp Gly Xaa Gly Thr Xaa Val Thr Val Ser Ser
1               5                   10

<210> SEQ ID NO 39
<211> LENGTH: 23
<212> TYPE: PRT
<213> ORGANISM: Artificial Sequence
<220> FEATURE:
<223> OTHER INFORMATION: L-FR1general formula3E2 L-FR1VLV2~VLV4 L-FR1)
<220> FEATURE:
<221> NAME/KEY: X
<222> LOCATION: (14)..(14)
<223> OTHER INFORMATION: X is S or T
<220> FEATURE:
<221> NAME/KEY: X
<222> LOCATION: (17)..(17)
<223> OTHER INFORMATION: X is Q or D
<220> FEATURE:
<221> NAME/KEY: X
<222> LOCATION: (18)..(18)
<223> OTHER INFORMATION: X is P or Q

<400> SEQUENCE: 39

Asp Ile Val Met Thr Gln Ser Pro Leu Ser Leu Pro Val Xaa Leu Gly
1               5                   10                  15
```

```
Xaa Xaa Ala Ser Ile Ser Cys
         20
```

```
<210> SEQ ID NO 40
<211> LENGTH: 15
<212> TYPE: PRT
<213> ORGANISM: Artificial Sequence
<220> FEATURE:
<223> OTHER INFORMATION: L-FR2 general formula3E2 L-FR2VLV2~VLV4 L-FR2)
<220> FEATURE:
<221> NAME/KEY: X
<222> LOCATION: (5)..(5)
<223> OTHER INFORMATION: X is R or K
```

```
<400> SEQUENCE: 40
```

```
Trp Tyr Leu Gln Xaa Pro Gly Gln Ser Pro Lys Leu Leu Ile Tyr
1               5                   10                  15
```

```
<210> SEQ ID NO 41
<211> LENGTH: 32
<212> TYPE: PRT
<213> ORGANISM: Artificial Sequence
<220> FEATURE:
<223> OTHER INFORMATION: L-FR3 general formula3E2 L-FR3VLV2~VLV4 L-FR3)
<220> FEATURE:
<221> NAME/KEY: X
<222> LOCATION: (27)..(27)
<223> OTHER INFORMATION: X is L or V
```

```
<400> SEQUENCE: 41
```

```
Gly Val Pro Asp Arg Phe Ser Gly Ser Gly Ser Gly Thr Asp Phe Thr
1               5                   10                  15
```

```
Leu Lys Ile Ser Arg Val Glu Ala Glu Asp Xaa Gly Val Tyr Tyr Cys
            20                  25                  30
```

```
<210> SEQ ID NO 42
<211> LENGTH: 10
<212> TYPE: PRT
<213> ORGANISM: Artificial Sequence
<220> FEATURE:
<223> OTHER INFORMATION: L-FR4 general formula3E2 L-FR4VLV2~VLV4 L-FR4)
<220> FEATURE:
<221> NAME/KEY: X
<222> LOCATION: (7)..(7)
<223> OTHER INFORMATION: X is V or L
```

```
<400> SEQUENCE: 42
```

```
Phe Gly Gly Gly Thr Lys Xaa Glu Ile Lys
1               5                   10
```

```
<210> SEQ ID NO 43
<211> LENGTH: 450
<212> TYPE: PRT
<213> ORGANISM: Artificial Sequence
<220> FEATURE:
<223> OTHER INFORMATION: 3E2 1-2/1-3/1-4 HC
```

```
<400> SEQUENCE: 43
```

```
Gln Val Thr Leu Gln Glu Ser Gly Pro Thr Leu Val Lys Pro Thr Gln
1               5                   10                  15
```

```
Thr Leu Thr Leu Thr Cys Thr Phe Ser Gly Phe Ser Leu Ser Thr Phe
            20                  25                  30
```

```
Gly Met Gly Val Gly Trp Ile Arg Gln Pro Pro Gly Lys Gly Leu Glu
        35                  40                  45
```

```
Trp Leu Val Leu Ile Leu Trp Asn Asp Ile Lys Tyr Tyr Asn Pro Ala
    50                  55                  60
```

```
Leu Lys Ser Leu Leu Thr Val Thr Lys Asp Thr Ser Lys Asn Gln Val
65              70                  75                  80

Val Leu Thr Ile Thr Asn Met Asp Pro Val Asp Thr Ala Thr Tyr Tyr
                85                  90                  95

Cys Ala Arg Val Asp Gly Tyr Tyr Gly Tyr Phe Asp Val Trp Gly Gln
            100             105             110

Gly Thr Met Val Thr Val Ser Ser Ala Ser Thr Lys Gly Pro Ser Val
        115             120             125

Phe Pro Leu Ala Pro Ser Ser Lys Ser Thr Ser Gly Gly Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
        180             185             190

Ser Ser Ser Leu Gly Thr Gln Thr Tyr Ile Cys Asn Val Asn His Lys
        195             200             205

Pro Ser Asn Thr Lys Val Asp Lys Lys Val Glu Pro Lys Ser Cys Asp
    210             215             220

Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
        260             265             270

Asp Pro Glu Val Lys Phe Asn Trp Tyr Val Asp Gly Val Glu Val His
        275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Asp Glu Leu Thr Lys Asn Gln Val Ser Leu
        355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly Lys
    450
```

<210> SEQ ID NO 44
<211> LENGTH: 450

```
<212> TYPE: PRT
<213> ORGANISM: Artificial Sequence
<220> FEATURE:
<223> OTHER INFORMATION: 3E2 2-2/2-3/2-4 HC

<400> SEQUENCE: 44

Gln Val Gln Leu Gln Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Val Leu Ile Leu Trp Asn Asp Ile Lys Tyr Tyr Asn Pro Ala
    50                  55                  60

Leu Lys Ser Leu Leu Thr Val Thr Lys Asp Thr Ser Lys Asn Gln Val
65                  70                  75                  80

Val Leu Thr Ile Thr Asn Met Asp Pro Val Asp Thr Ala Thr Tyr Tyr
                85                  90                  95

Cys Ala Arg Val Asp Gly Tyr Tyr Gly Tyr Phe Asp Val Trp Gly Gln
                100                 105                 110

Gly Thr Met Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

-continued

```
Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly Lys
    450

<210> SEQ ID NO 45
<211> LENGTH: 450
<212> TYPE: PRT
<213> ORGANISM: Artificial Sequence
<220> FEATURE:
<223> OTHER INFORMATION: 3E2 3-2/3-3/3-4 HC

<400> SEQUENCE: 45

Gln Val Gln Leu Gln Glu Ser Gly Pro Thr Leu Val Lys Pro Thr Gln
1               5               10              15

Thr Leu Thr Leu Thr Cys Thr Phe Ser Gly Phe Ser Leu Ser Thr Phe
            20              25              30

Gly Met Gly Val Gly Trp Ile Arg Gln Pro Ser Gly Lys Gly Leu Glu
        35              40              45

Trp Leu Val Leu Ile Leu Trp Asn Asp Ile Lys Tyr Tyr Asn Pro Ala
        50              55              60

Leu Lys Ser Leu Leu Thr Val Thr Lys Asp Thr Ser Lys Asn Gln Val
65              70              75              80

Val Leu Thr Ile Thr Asn Met Asp Pro Val Asp Thr Ala Thr Tyr Tyr
            85              90              95

Cys Ala Arg Val Asp Gly Tyr Tyr Gly Tyr Phe Asp Val Trp Gly Thr
            100             105             110

Gly Thr Thr Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
        130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Lys Lys Val Glu Pro Lys Ser Cys Asp
        210             215             220

Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
            275             280             285
```

-continued

```
Asn Ala Lys Thr Lys Pro Arg Glu Glu Gln Tyr Asn Ser Thr Tyr Arg
    290             295                 300

Val Val Ser Val Leu Thr Val Leu His Gln Asp Trp Leu Asn Gly Lys
305             310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 46
<211> LENGTH: 219
<212> TYPE: PRT
<213> ORGANISM: Artificial Sequence
<220> FEATURE:
<223> OTHER INFORMATION: 3E2 1-2/2-2/3-2 LC

<400> SEQUENCE: 46

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Thr Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 47
<211> LENGTH: 219
<212> TYPE: PRT
<213> ORGANISM: Artificial Sequence
<220> FEATURE:
<223> OTHER INFORMATION: 3E2 1-3/2-3/3-3 LC

<400> SEQUENCE: 47

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 48
<211> LENGTH: 219
<212> TYPE: PRT
<213> ORGANISM: Artificial Sequence
<220> FEATURE:
<223> OTHER INFORMATION: 3E2 1-4/2-4/3-4 LC

<400> SEQUENCE: 48

Asp Ile Val Met Thr Gln Ser Pro Leu Ser Leu Pro Val Thr Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

-continued

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 49
<211> LENGTH: 241
<212> TYPE: PRT
<213> ORGANISM: Homo sapiens

<400> SEQUENCE: 49

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
            115                 120                 125

Lys Pro Trp Thr Asp Cys Thr Gln Phe Gly Phe Leu Thr Val Phe Pro
        130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205
```

```
Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val

<210> SEQ ID NO 50
<211> LENGTH: 161
<212> TYPE: PRT
<213> ORGANISM: Homo sapiens

<400> SEQUENCE: 50

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
                20                  25                  30

Gly Cys Gly Pro Gly Arg Leu Leu Leu Gly Thr Gly Thr Asp Ala Arg
            35                  40                  45

Cys Cys Arg Val His Thr Thr Arg Cys Cys Arg Asp Tyr Pro Gly Glu
        50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
                100                 105                 110

Ile Asp Cys Ala Ser Gly Thr Phe Ser Gly Gly His Glu Gly His Cys
            115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu

<210> SEQ ID NO 51
<211> LENGTH: 235
<212> TYPE: PRT
<213> ORGANISM: Macaca fascicularis

<400> SEQUENCE: 51

Met Cys Ala Cys Gly Thr Leu Cys Cys Leu Ala Leu Leu Cys Ala Ala
1               5                   10                  15

Ser Leu Gly Gln Arg Pro Thr Gly Gly Pro Gly Cys Gly Pro Gly Arg
                20                  25                  30

Leu Leu Leu Gly Thr Gly Lys Asp Ala Arg Cys Cys Arg Val His Pro
            35                  40                  45

Thr Arg Cys Cys Arg Asp Tyr Gln Ser Glu Glu Cys Cys Ser Glu Trp
        50                  55                  60

Asp Cys Val Cys Val Gln Pro Glu Phe His Cys Gly Asp Pro Cys Cys
65                  70                  75                  80

Thr Thr Cys Gln His His Pro Cys Pro Ser Gly Gln Gly Val Gln Pro
                85                  90                  95

Gln Gly Lys Phe Ser Phe Gly Phe Arg Cys Val Asp Cys Ala Leu Gly
                100                 105                 110
```

Thr Phe Ser Arg Gly His Asp Gly His Cys Lys Pro Trp Thr Asp Cys
        115                 120                 125

Thr Gln Phe Gly Phe Leu Thr Val Phe Pro Gly Asn Lys Thr His Asn
    130                 135                 140

Ala Val Cys Val Pro Gly Ser Pro Pro Ala Glu Pro Pro Gly Trp Leu
145                 150                 155                 160

Thr Ile Val Leu Leu Ala Val Ala Ala Cys Val Leu Leu Thr Ser
        165                 170                 175

Ala Gln Leu Gly Leu His Ile Trp Gln Leu Arg Ser Gln Pro Thr Gly
        180                 185                 190

Pro Arg Glu Thr Gln Leu Leu Leu Glu Val Pro Pro Ser Thr Glu Asp
        195                 200                 205

Ala Ser Ser Cys Gln Phe Pro Glu Glu Glu Arg Gly Glu Arg Leu Ala
    210                 215                 220

Glu Glu Lys Gly Arg Leu Gly Asp Leu Trp Val
225                 230                 235

<210> SEQ ID NO 52
<211> LENGTH: 155
<212> TYPE: PRT
<213> ORGANISM: Macaca fascicularis

<400> SEQUENCE: 52

Met Cys Ala Cys Gly Thr Leu Cys Cys Leu Ala Leu Leu Cys Ala Ala
1               5                   10                  15

Ser Leu Gly Gln Arg Pro Thr Gly Gly Pro Gly Cys Gly Pro Gly Arg
        20                  25                  30

Leu Leu Leu Gly Thr Gly Lys Asp Ala Arg Cys Cys Arg Val His Pro
        35                  40                  45

Thr Arg Cys Cys Arg Asp Tyr Gln Ser Glu Glu Cys Cys Ser Glu Trp
    50                  55                  60

Asp Cys Val Cys Val Gln Pro Glu Phe His Cys Gly Asp Pro Cys Cys
65                  70                  75                  80

Thr Thr Cys Gln His His Pro Cys Pro Ser Gly Gln Gly Val Gln Pro
        85                  90                  95

Gln Gly Lys Phe Ser Phe Gly Phe Arg Cys Val Asp Cys Ala Leu Gly
        100                 105                 110

Thr Phe Ser Arg Gly His Asp Gly His Cys Lys Pro Trp Thr Asp Cys
        115                 120                 125

Thr Gln Phe Gly Phe Leu Thr Val Phe Pro Gly Asn Lys Thr His Asn
    130                 135                 140

Ala Val Cys Val Pro Gly Ser Pro Pro Ala Glu
145                 150                 155

<210> SEQ ID NO 53
<211> LENGTH: 330
<212> TYPE: PRT
<213> ORGANISM: Homo sapiens

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
        20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 54
<211> LENGTH: 227
<212> TYPE: PRT
<213> ORGANISM: Homo sapiens

<400> SEQUENCE: 54

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

-continued

```
Arg Val Val Ser Val Leu Thr Val Leu His Gln Asp Trp Leu Asn Gly
                85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
        115             120             125

Tyr Thr Leu Pro Pro Ser Arg Asp Glu Leu Thr Lys Asn Gln Val Ser
    130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
            165             170             175

Val Leu Asp Ser Asp Gly Ser Phe Phe Leu Tyr Ser Lys Leu Thr Val
            180             185             190

Asp Lys Ser Arg Trp Gln Gln Gly Asn Val Phe Ser Cys Ser Val Met
        195             200             205

His Glu Ala Leu His Asn His Tyr Thr Gln Lys Ser Leu Ser Leu Ser
    210             215             220

Pro Gly Lys
225

<210> SEQ ID NO 55
<211> LENGTH: 107
<212> TYPE: PRT
<213> ORGANISM: Homo sapiens

<400> SEQUENCE: 55

Arg Thr Val Ala Ala Pro Ser Val Phe Ile Phe Pro Pro Ser Asp Glu
1               5               10              15

Gln Leu Lys Ser Gly Thr Ala Ser Val Val Cys Leu Leu Asn Asn Phe
            20              25              30

Tyr Pro Arg Glu Ala Lys Val Gln Trp Lys Val Asp Asn Ala Leu Gln
        35              40              45

Ser Gly Asn Ser Gln Glu Ser Val Thr Glu Gln Asp Ser Lys Asp Ser
    50              55              60

Thr Tyr Ser Leu Ser Ser Thr Leu Thr Leu Ser Lys Ala Asp Tyr Glu
65              70              75              80

Lys His Lys Val Tyr Ala Cys Glu Val Thr His Gln Gly Leu Ser Ser
            85              90              95

Pro Val Thr Lys Ser Phe Asn Arg Gly Glu Cys
            100             105

<210> SEQ ID NO 56
<211> LENGTH: 324
<212> TYPE: PRT
<213> ORGANISM: Mus musculus

<400> SEQUENCE: 56

Ala Lys Thr Thr Pro Pro Ser Val Tyr Pro Leu Ala Pro Gly Ser Ala
1               5               10              15

Ala Gln Thr Asn Ser Met Val Thr Leu Gly Cys Leu Val Lys Gly Tyr
            20              25              30

Phe Pro Glu Pro Val Thr Val Thr Trp Asn Ser Gly Ser Leu Ser Ser
        35              40              45

Gly Val His Thr Phe Pro Ala Val Leu Gln Ser Asp Leu Tyr Thr Leu
    50              55              60
```

-continued

Ser Ser Ser Val Thr Val Pro Ser Ser Pro Arg Pro Ser Glu Thr Val
65              70              75              80

Thr Cys Asn Val Ala His Pro Ala Ser Ser Thr Lys Val Asp Lys Lys
                85              90              95

Ile Val Pro Arg Asp Cys Gly Cys Lys Pro Cys Ile Cys Thr Val Pro
            100             105             110

Glu Val Ser Ser Val Phe Ile Phe Pro Pro Lys Pro Lys Asp Val Leu
            115             120             125

Thr Ile Thr Leu Thr Pro Lys Val Thr Cys Val Val Val Asp Ile Ser
        130             135             140

Lys Asp Asp Pro Glu Val Gln Phe Ser Trp Phe Val Asp Asp Val Glu
145             150             155             160

Val His Thr Ala Gln Thr Gln Pro Arg Glu Glu Gln Phe Asn Ser Thr
                165             170             175

Phe Arg Ser Val Ser Glu Leu Pro Ile Met His Gln Asp Trp Leu Asn
            180             185             190

Gly Lys Glu Phe Lys Cys Arg Val Asn Ser Ala Ala Phe Pro Ala Pro
            195             200             205

Ile Glu Lys Thr Ile Ser Lys Thr Lys Gly Arg Pro Lys Ala Pro Gln
        210             215             220

Val Tyr Thr Ile Pro Pro Pro Lys Glu Gln Met Ala Lys Asp Lys Val
225             230             235             240

Ser Leu Thr Cys Met Ile Thr Asp Phe Phe Pro Glu Asp Ile Thr Val
            245             250             255

Glu Trp Gln Trp Asn Gly Gln Pro Ala Glu Asn Tyr Lys Asn Thr Gln
            260             265             270

Pro Ile Met Asn Thr Asn Gly Ser Tyr Phe Val Tyr Ser Lys Leu Asn
            275             280             285

Val Gln Lys Ser Asn Trp Glu Ala Gly Asn Thr Phe Thr Cys Ser Val
        290             295             300

Leu His Glu Gly Leu His Asn His His Thr Glu Lys Ser Leu Ser His
305             310             315             320

Ser Pro Gly Lys

<210> SEQ ID NO 57
<211> LENGTH: 227
<212> TYPE: PRT
<213> ORGANISM: Mus musculus

<400> SEQUENCE: 57

Val Pro Arg Asp Cys Gly Cys Lys Pro Cys Ile Cys Thr Val Pro Glu
1               5               10              15

Val Ser Ser Val Phe Ile Phe Pro Pro Lys Pro Lys Asp Val Leu Thr
            20              25              30

Ile Thr Leu Thr Pro Lys Val Thr Cys Val Val Val Asp Ile Ser Lys
        35              40              45

Asp Asp Pro Glu Val Gln Phe Ser Trp Phe Val Asp Asp Val Glu Val
        50              55              60

His Thr Ala Gln Thr Gln Pro Arg Glu Glu Gln Phe Asn Ser Thr Phe
65              70              75              80

Arg Ser Val Ser Glu Leu Pro Ile Met His Gln Asp Trp Leu Asn Gly
                85              90              95

Lys Glu Phe Lys Cys Arg Val Asn Ser Ala Ala Phe Pro Ala Pro Ile
            100             105             110

-continued

```
Glu Lys Thr Ile Ser Lys Thr Lys Gly Arg Pro Lys Ala Pro Gln Val
    115                 120                 125

Tyr Thr Ile Pro Pro Pro Lys Glu Gln Met Ala Lys Asp Lys Val Ser
    130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asn Thr Asn Gly Ser Tyr Phe Val Tyr Ser Lys Leu Asn Val
                180                 185                 190

Gln Lys Ser Asn Trp Glu Ala Gly Asn Thr Phe Thr Cys Ser Val Leu
                195                 200                 205

His Glu Gly Leu His Asn His His Thr Glu Lys Ser Leu Ser His Ser
    210                 215                 220

Pro Gly Lys
225

<210> SEQ ID NO 58
<211> LENGTH: 388
<212> TYPE: PRT
<213> ORGANISM: Artificial Sequence
<220> FEATURE:
<223> OTHER INFORMATION: hGITR-Fc

<400> SEQUENCE: 58

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
                20                  25                  30

Gly Cys Gly Pro Gly Arg Leu Leu Leu Gly Thr Gly Thr Asp Ala Arg
                35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
                100                 105                 110

Ile Asp Cys Ala Ser Gly Thr Phe Ser Gly Gly His Glu Gly His Cys
                115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Asp Lys Thr His Thr Cys Pro Pro Cys Pro Ala Pro Glu Leu Leu
                165                 170                 175

Gly Gly Pro Ser Val Phe Leu Phe Pro Pro Lys Pro Lys Asp Thr Leu
                180                 185                 190

Met Ile Ser Arg Thr Pro Glu Val Thr Cys Val Val Val Asp Val Ser
                195                 200                 205

His Glu Asp Pro Glu Val Lys Phe Asn Trp Tyr Val Asp Gly Val Glu
    210                 215                 220

Val His Asn Ala Lys Thr Lys Pro Arg Glu Glu Gln Tyr Asn Ser Thr
225                 230                 235                 240
```

-continued

```
Tyr Arg Val Val Ser Val Leu Thr Val Leu His Gln Asp Trp Leu Asn
            245             250             255

Gly Lys Glu Tyr Lys Cys Lys Val Ser Asn Lys Ala Leu Pro Ala Pro
            260             265             270

Ile Glu Lys Thr Ile Ser Lys Ala Lys Gly Gln Pro Arg Glu Pro Gln
            275             280             285

Val Tyr Thr Leu Pro Pro Ser Arg Asp Glu Leu Thr Lys Asn Gln Val
        290             295             300

Ser Leu Thr Cys Leu Val Lys Gly Phe Tyr Pro Ser Asp Ile Ala Val
    305             310             315             320

Glu Trp Glu Ser Asn Gly Gln Pro Glu Asn Asn Tyr Lys Thr Thr Pro
                325             330             335

Pro Val Leu Asp Ser Asp Gly Ser Phe Phe Leu Tyr Ser Lys Leu Thr
                340             345             350

Val Asp Lys Ser Arg Trp Gln Gln Gly Asn Val Phe Ser Cys Ser Val
            355             360             365

Met His Glu Ala Leu His Asn His Tyr Thr Gln Lys Ser Leu Ser Leu
        370             375             380

Ser Pro Gly Lys
385
```

```
<210> SEQ ID NO 59
<211> LENGTH: 388
<212> TYPE: PRT
<213> ORGANISM: Artificial Sequence
<220> FEATURE:
<223> OTHER INFORMATION: hGITR-muFc

<400> SEQUENCE: 59
```

```
Met Ala Gln His Gly Ala Met Gly Ala Phe Arg Ala Leu Cys Gly Leu
1               5               10              15

Ala Leu Leu Cys Ala Leu Ser Leu Gly Gln Arg Pro Thr Gly Gly Pro
            20              25              30

Gly Cys Gly Pro Gly Arg Leu Leu Leu Gly Thr Gly Thr Asp Ala Arg
            35              40              45

Cys Cys Arg Val His Thr Thr Arg Cys Cys Arg Asp Tyr Pro Gly Glu
    50              55              60

Glu Cys Cys Ser Glu Trp Asp Cys Met Cys Val Gln Pro Glu Phe His
65              70              75              80

Cys Gly Asp Pro Cys Cys Thr Thr Cys Arg His His Pro Cys Pro Pro
                85              90              95

Gly Gln Gly Val Gln Ser Gln Gly Lys Phe Ser Phe Gly Phe Gln Cys
            100             105             110

Ile Asp Cys Ala Ser Gly Thr Phe Ser Gly Gly His Glu Gly His Cys
            115             120             125

Lys Pro Trp Thr Asp Cys Thr Gln Phe Gly Phe Leu Thr Val Phe Pro
        130             135             140

Gly Asn Lys Thr His Asn Ala Val Cys Val Pro Gly Ser Pro Pro Ala
145             150             155             160

Glu Val Pro Arg Asp Cys Gly Cys Lys Pro Cys Ile Cys Thr Val Pro
                165             170             175

Glu Val Ser Ser Val Phe Ile Phe Pro Pro Lys Pro Lys Asp Val Leu
            180             185             190

Thr Ile Thr Leu Thr Pro Lys Val Thr Cys Val Val Val Asp Ile Ser
        195             200             205
```

-continued

```
Lys Asp Asp Pro Glu Val Gln Phe Ser Trp Phe Val Asp Asp Val Glu
    210             215                 220

Val His Thr Ala Gln Thr Gln Pro Arg Glu Glu Gln Phe Asn Ser Thr
225             230                 235                 240

Phe Arg Ser Val Ser Glu Leu Pro Ile Met His Gln Asp Trp Leu Asn
            245                 250                 255

Gly Lys Glu Phe Lys Cys Arg Val Asn Ser Ala Ala Phe Pro Ala Pro
            260                 265                 270

Ile Glu Lys Thr Ile Ser Lys Thr Lys Gly Arg Pro Lys Ala Pro Gln
            275                 280                 285

Val Tyr Thr Ile Pro Pro Pro Lys Glu Gln Met Ala Lys Asp Lys Val
    290                 295                 300

Ser Leu Thr Cys Met Ile Thr Asp Phe Phe Pro Glu Asp Ile Thr Val
305                 310                 315                 320

Glu Trp Gln Trp Asn Gly Gln Pro Ala Glu Asn Tyr Lys Asn Thr Gln
                325                 330                 335

Pro Ile Met Asn Thr Asn Gly Ser Tyr Phe Val Tyr Ser Lys Leu Asn
            340                 345                 350

Val Gln Lys Ser Asn Trp Glu Ala Gly Asn Thr Phe Thr Cys Ser Val
            355                 360                 365

Leu His Glu Gly Leu His Asn His His Thr Glu Lys Ser Leu Ser His
    370                 375                 380

Ser Pro Gly Lys
385

<210> SEQ ID NO 60
<211> LENGTH: 382
<212> TYPE: PRT
<213> ORGANISM: Artificial Sequence
<220> FEATURE:
<223> OTHER INFORMATION: cynoGITR-muFc

<400> SEQUENCE: 60

Met Cys Ala Cys Gly Thr Leu Cys Cys Leu Ala Leu Leu Cys Ala Ala
1               5                   10                  15

Ser Leu Gly Gln Arg Pro Thr Gly Gly Pro Gly Cys Gly Pro Gly Arg
            20                  25                  30

Leu Leu Leu Gly Thr Gly Lys Asp Ala Arg Cys Cys Arg Val His Pro
        35                  40                  45

Thr Arg Cys Cys Arg Asp Tyr Gln Ser Glu Glu Cys Cys Ser Glu Trp
    50                  55                  60

Asp Cys Val Cys Val Gln Pro Glu Phe His Cys Gly Asp Pro Cys Cys
65                  70                  75                  80

Thr Thr Cys Gln His His Pro Cys Pro Ser Gly Gln Gly Val Gln Pro
                85                  90                  95

Gln Gly Lys Phe Ser Phe Gly Phe Arg Cys Val Asp Cys Ala Leu Gly
            100                 105                 110

Thr Phe Ser Arg Gly His Asp Gly His Cys Lys Pro Trp Thr Asp Cys
            115                 120                 125

Thr Gln Phe Gly Phe Leu Thr Val Phe Pro Gly Asn Lys Thr His Asn
            130                 135                 140

Ala Val Cys Val Pro Gly Ser Pro Pro Ala Glu Val Pro Arg Asp Cys
145                 150                 155                 160

Gly Cys Lys Pro Cys Ile Cys Thr Val Pro Glu Val Ser Ser Val Phe
                165                 170                 175
```

-continued

```
Ile Phe Pro Pro Lys Pro Lys Asp Val Leu Thr Ile Thr Leu Thr Pro
            180             185                 190

Lys Val Thr Cys Val Val Val Asp Ile Ser Lys Asp Asp Pro Glu Val
            195             200             205

Gln Phe Ser Trp Phe Val Asp Asp Val Glu Val His Thr Ala Gln Thr
        210             215             220

Gln Pro Arg Glu Glu Gln Phe Asn Ser Thr Phe Arg Ser Val Ser Glu
225             230             235             240

Leu Pro Ile Met His Gln Asp Trp Leu Asn Gly Lys Glu Phe Lys Cys
            245             250             255

Arg Val Asn Ser Ala Ala Phe Pro Ala Pro Ile Glu Lys Thr Ile Ser
            260             265             270

Lys Thr Lys Gly Arg Pro Lys Ala Pro Gln Val Tyr Thr Ile Pro Pro
            275             280             285

Pro Lys Glu Gln Met Ala Lys Asp Lys Val Ser Leu Thr Cys Met Ile
            290             295             300

Thr Asp Phe Phe Pro Glu Asp Ile Thr Val Glu Trp Gln Trp Asn Gly
305             310             315             320

Gln Pro Ala Glu Asn Tyr Lys Asn Thr Gln Pro Ile Met Asn Thr Asn
            325             330             335

Gly Ser Tyr Phe Val Tyr Ser Lys Leu Asn Val Gln Lys Ser Asn Trp
            340             345             350

Glu Ala Gly Asn Thr Phe Thr Cys Ser Val Leu His Glu Gly Leu His
            355             360             365

Asn His His Thr Glu Lys Ser Leu Ser His Ser Pro Gly Lys
            370             375             380
```

```
<210> SEQ ID NO 61
<211> LENGTH: 400
<212> TYPE: PRT
<213> ORGANISM: Artificial Sequence
<220> FEATURE:
<223> OTHER INFORMATION: hGITR-EGFP

<400> SEQUENCE: 61
```

```
Met Ala Gln His Gly Ala Met Gly Ala Phe Arg Ala Leu Cys Gly Leu
1               5               10              15

Ala Leu Leu Cys Ala Leu Ser Leu Gly Gln Arg Pro Thr Gly Gly Pro
            20              25              30

Gly Cys Gly Pro Gly Arg Leu Leu Leu Gly Thr Gly Thr Asp Ala Arg
            35              40              45

Cys Cys Arg Val His Thr Thr Arg Cys Cys Arg Asp Tyr Pro Gly Glu
        50              55              60

Glu Cys Cys Ser Glu Trp Asp Cys Met Cys Val Gln Pro Glu Phe His
65              70              75              80

Cys Gly Asp Pro Cys Cys Thr Thr Cys Arg His His Pro Cys Pro Pro
            85              90              95

Gly Gln Gly Val Gln Ser Gln Gly Lys Phe Ser Phe Gly Phe Gln Cys
            100             105             110

Ile Asp Cys Ala Ser Gly Thr Phe Ser Gly Gly His Glu Gly His Cys
            115             120             125

Lys Pro Trp Thr Asp Cys Thr Gln Phe Gly Phe Leu Thr Val Phe Pro
            130             135             140

Gly Asn Lys Thr His Asn Ala Val Cys Val Pro Gly Ser Pro Pro Ala
145             150             155             160
```

```
Glu Met Val Ser Lys Gly Glu Glu Leu Phe Thr Gly Val Val Pro Ile
            165             170             175

Leu Val Glu Leu Asp Gly Asp Val Asn Gly His Lys Phe Ser Val Ser
            180             185             190

Gly Glu Gly Glu Gly Asp Ala Thr Tyr Gly Lys Leu Thr Leu Lys Phe
            195             200             205

Ile Cys Thr Thr Gly Lys Leu Pro Val Pro Trp Pro Thr Leu Val Thr
    210             215             220

Thr Leu Thr Tyr Gly Val Gln Cys Phe Ser Arg Tyr Pro Asp His Met
225             230             235             240

Lys Gln His Asp Phe Phe Lys Ser Ala Met Pro Glu Gly Tyr Val Gln
            245             250             255

Glu Arg Thr Ile Phe Phe Lys Asp Asp Gly Asn Tyr Lys Thr Arg Ala
            260             265             270

Glu Val Lys Phe Glu Gly Asp Thr Leu Val Asn Arg Ile Glu Leu Lys
            275             280             285

Gly Ile Asp Phe Lys Glu Asp Gly Asn Ile Leu Gly His Lys Leu Glu
    290             295             300

Tyr Asn Tyr Asn Ser His Asn Val Tyr Ile Met Ala Asp Lys Gln Lys
305             310             315             320

Asn Gly Ile Lys Val Asn Phe Lys Ile Arg His Asn Ile Glu Asp Gly
            325             330             335

Ser Val Gln Leu Ala Asp His Tyr Gln Gln Asn Thr Pro Ile Gly Asp
            340             345             350

Gly Pro Val Leu Leu Pro Asp Asn His Tyr Leu Ser Thr Gln Ser Ala
            355             360             365

Leu Ser Lys Asp Pro Asn Glu Lys Arg Asp His Met Val Leu Leu Glu
    370             375             380

Phe Val Thr Ala Ala Gly Ile Thr Leu Gly Met Asp Glu Leu Tyr Lys
385             390             395             400

<210> SEQ ID NO 62
<211> LENGTH: 394
<212> TYPE: PRT
<213> ORGANISM: Artificial Sequence
<220> FEATURE:
<223> OTHER INFORMATION: cynoGITR-EGFP

<400> SEQUENCE: 62

Met Cys Ala Cys Gly Thr Leu Cys Cys Leu Ala Leu Leu Cys Ala Ala
1               5               10              15

Ser Leu Gly Gln Arg Pro Thr Gly Gly Pro Gly Cys Gly Pro Gly Arg
            20              25              30

Leu Leu Leu Gly Thr Gly Lys Asp Ala Arg Cys Cys Arg Val His Pro
            35              40              45

Thr Arg Cys Cys Arg Asp Tyr Gln Ser Glu Glu Cys Cys Ser Glu Trp
    50              55              60

Asp Cys Val Cys Val Gln Pro Glu Phe His Cys Gly Asp Pro Cys Cys
65              70              75              80

Thr Thr Cys Gln His His Pro Cys Pro Ser Gly Gln Gly Val Gln Pro
            85              90              95

Gln Gly Lys Phe Ser Phe Gly Phe Arg Cys Val Asp Cys Ala Leu Gly
            100             105             110

Thr Phe Ser Arg Gly His Asp Gly His Cys Lys Pro Trp Thr Asp Cys
            115             120             125
```

```
Thr Gln Phe Gly Phe Leu Thr Val Phe Pro Gly Asn Lys Thr His Asn
    130                 135                 140

Ala Val Cys Val Pro Gly Ser Pro Pro Ala Glu Met Val Ser Lys Gly
145                 150                 155                 160

Glu Glu Leu Phe Thr Gly Val Val Pro Ile Leu Val Glu Leu Asp Gly
                165                 170                 175

Asp Val Asn Gly His Lys Phe Ser Val Ser Gly Glu Gly Glu Gly Asp
                180                 185                 190

Ala Thr Tyr Gly Lys Leu Thr Leu Lys Phe Ile Cys Thr Thr Gly Lys
                195                 200                 205

Leu Pro Val Pro Trp Pro Thr Leu Val Thr Thr Leu Thr Tyr Gly Val
    210                 215                 220

Gln Cys Phe Ser Arg Tyr Pro Asp His Met Lys Gln His Asp Phe Phe
225                 230                 235                 240

Lys Ser Ala Met Pro Glu Gly Tyr Val Gln Glu Arg Thr Ile Phe Phe
                245                 250                 255

Lys Asp Asp Gly Asn Tyr Lys Thr Arg Ala Glu Val Lys Phe Glu Gly
                260                 265                 270

Asp Thr Leu Val Asn Arg Ile Glu Leu Lys Gly Ile Asp Phe Lys Glu
                275                 280                 285

Asp Gly Asn Ile Leu Gly His Lys Leu Glu Tyr Asn Tyr Asn Ser His
    290                 295                 300

Asn Val Tyr Ile Met Ala Asp Lys Gln Lys Asn Gly Ile Lys Val Asn
305                 310                 315                 320

Phe Lys Ile Arg His Asn Ile Glu Asp Gly Ser Val Gln Leu Ala Asp
                325                 330                 335

His Tyr Gln Gln Asn Thr Pro Ile Gly Asp Gly Pro Val Leu Leu Pro
                340                 345                 350

Asp Asn His Tyr Leu Ser Thr Gln Ser Ala Leu Ser Lys Asp Pro Asn
                355                 360                 365

Glu Lys Arg Asp His Met Val Leu Leu Glu Phe Val Thr Ala Ala Gly
    370                 375                 380

Ile Thr Leu Gly Met Asp Glu Leu Tyr Lys
385                 390
```

```
<210> SEQ ID NO 63
<211> LENGTH: 450
<212> TYPE: PRT
<213> ORGANISM: Artificial Sequence
<220> FEATURE:
<223> OTHER INFORMATION: C3E2 heavy chain

<400> SEQUENCE: 63
```

```
Gln Val Gln Leu Gln Glu Ser Gly Pro Gly Ile Leu Gln Pro Ser Gln
1                   5                   10                  15

Thr Leu Ser Leu Thr Cys Ser Phe Ser Gly Phe Ser Leu Ser Thr Phe
                20                  25                  30

Gly Met Gly Val Gly Trp Ile Arg Gln Pro Ser Gly Lys Gly Leu Glu
                35                  40                  45

Trp Leu Val Leu Ile Leu Trp Asn Asp Ile Lys Tyr Tyr Asn Pro Ala
    50                  55                  60

Leu Lys Ser Leu Leu Thr Val Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95
```

-continued

```
Cys Ala Arg Val Asp Gly Tyr Tyr Gly Tyr Phe Asp Val Trp Gly Thr
        100             105             110

Gly Thr Thr Val Thr Val Ser Ser Ala Ser Thr Lys Gly Pro Ser Val
        115             120             125

Phe Pro Leu Ala Pro Ser Ser Lys Ser Thr Ser Gly Gly Thr Ala Ala
130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Lys Lys Val Glu Pro Lys Ser Cys Asp
        210             215             220

Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
        275             280             285

Asn Ala Lys Thr Lys Pro Arg Glu Glu Gln Tyr Asn Ser Thr Tyr Arg
        290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Asp Glu Leu Thr Lys Asn Gln Val Ser Leu
            355             360             365

Thr Cys Leu Val Lys Gly Phe Tyr Pro Ser Asp Ile Ala Val Glu Trp
        370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
    450
```

```
<210> SEQ ID NO 64
<211> LENGTH: 219
<212> TYPE: PRT
<213> ORGANISM: Artificial Sequence
<220> FEATURE:
<223> OTHER INFORMATION: C3E2 light chain
```

<400> SEQUENCE: 64

```
Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 65
<211> LENGTH: 1164
<212> TYPE: DNA
<213> ORGANISM: Artificial Sequence
<220> FEATURE:
<223> OTHER INFORMATION: Nucleotide encoding hGITR-Fc

<400> SEQUENCE: 65

```
atggcacagc acggggcgat gggcgcgttt cgggccctgt gcggcctggc gctgctgtgc      60
gcgctcagcc tgggtcagcg ccccaccggg ggtcccgggt gcggccctgg cgcctcctg     120 cttgggacgg gaacggacgc gcgctgctgc cgggttcaca cgacgcgctg ctgccgcgat     180
tacccgggcg aggagtgctg ttccgagtgg gactgcatgt gtgtccagcc tgaattccac     240
tgcggagacc cttgctgcac gacctgccgg caccacccctt gtcccccagg ccagggggta     300
cagtcccagg ggaaattcag ttttggcttc agtgtatcg actgtgcctc ggggaccttc     360
tccgggggcc acgaaggcca ctgcaaacct tggacagact gcacccagtt cgggtttctc     420
actgtgttcc ctgggaacaa gacccacaac gctgtgtgcg tcccagggtc cccgccggca     480
gaggataaga cacacacctg ccctccatgc cccgcacctg aactcctggg cgggccttcc     540 gtttttcctgt ttcctcccaa gcccaaggat acactgatga ttagccgcac ccccgaagtc     600
acttgcgtgg tggtggatgt gagccatgaa gatccagaag ttaagtttaa ctggtatgtg     660
gacggggtcg aggtgcacaa tgctaaaaca aagcccaggg aggagcaata taactccaca     720
```

-continued

```
tacagagtgg tgtccgttct gacagtcctg caccaggact ggctgaacgg gaaggaatac      780
aagtgcaagg tgtctaataa ggcactgcca gcccccatag agaagacaat ctctaaagct      840
aaaggccaac cacgcgagcc tcaggtctac acactgccac catccaggga cgaactgacc      900
aagaatcagg tgagcctgac ttgtctcgtc aaaggattct acccaagcga catcgccgtg      960
gagtgggaat ccaacggcca accagagaac aactacaaga ccacccccacc agtcctggac     1020 tctgatggga gctttttcct gtattccaag ctgacagtgg acaagtctcg gtggcaacag     1080
ggcaacgtgt tcagctgctc cgtgatgcat gaagccctgc ataaccacta tacccagaaa     1140
agcctcagcc tgtcccccgg gaaa                                            1164
```

<210> SEQ ID NO 66
<211> LENGTH: 1164
<212> TYPE: DNA
<213> ORGANISM: Artificial Sequence
<220> FEATURE:
<223> OTHER INFORMATION: Nucleotide encoding hGITR-muFc

<400> SEQUENCE: 66

```
atggcacagc acggggcgat gggcgcgttt cgggccctgt gcggcctggc gctgctgtgc       60
gcgctcagcc tgggtcagcg ccccaccggg ggtcccgggt gcggccctgg cgcgcctcctg      120 cttgggacgg gaacggacgc gcgctgctgc cgggttcaca cgacgcgctg ctgccgcgat      180
tacccgggcg aggagtgctg ttccgagtgg gactgcatgt gtgtccagcc tgaattccac      240
tgcggagacc cttgctgcac gacctgccgg caccacccctt gtccccccagg ccagggggta      300 cagtcccagg ggaaattcag ttttggcttc cagtgtatcg actgtgcctc ggggaccttc      360
tccgggggcc acgaaggcca ctgcaaacct tggacagact gcacccagtt cgggtttctc      420
actgtgttcc ctgggaacaa gacccacaac gctgtgtgcg tcccagggtc cccgccggca      480
gaggtgccca gggattgtgg ttgtaagcct tgcatatgta cagtcccaga agtatcatct      540
gtcttcatct tcccccccaaa gcccaaggat gtgctcacca ttactctgac tcctaaggtc      600
acgtgtgttg tggtagacat cagcaaggat gatcccgagg tccagttcag ctggtttgta      660
gatgatgtgg aggtgcacac agctcagacg caaccccggg aggagcagtt caacagcact      720
ttccgctcag tcagtgaact tcccatcatg caccaggact ggctcaatgg caaggagttc      780
aaatgcaggg tcaacagtgc agctttccct gcccccatcg agaaaaccat ctccaaaacc      840
aaaggcagac cgaaggctcc acaggtgtac accattccac ctcccaagga gcagatggcc      900
aaggataaag tcagtctgac ctgcatgata acagacttct ccctgaaga cattactgtg      960 gagtggcagt ggaatgggca gccagcggag aactacaaga cacctcagcc catcatgaac     1020
acgaatggct cttacttcgt ctacagcaag ctcaatgtgc agaagagcaa ctgggaggca     1080
ggaaatactt tcacctgctc tgtgttacat gagggcctgc acaaccacca tactgagaag     1140
agcctctccc actctcctgg gaaa                                            1164
```

<210> SEQ ID NO 67
<211> LENGTH: 1146
<212> TYPE: DNA
<213> ORGANISM: Artificial Sequence
<220> FEATURE:
<223> OTHER INFORMATION: Nucleotide encoding cynoGITR-muFc

<400> SEQUENCE: 67

```
atgtgtgcgt gcgggaccct gtgctgcctg gcgctgctgt gtgcggccag cctgggtcag       60
cgccccaccg ggggtcccgg gtgcggccct gggcgcctcc tgctcgggac gggaaaggac      120
```

-continued

```
gcacgctgct gccgcgttca cccgacgcgc tgctgccgcg attaccagag cgaggagtgc        180
tgctccgagt gggactgcgt gtgtgtccag cctgaattcc actgcggaga cccttgctgc        240
acgacctgcc agcaccaccc ttgcccctca ggccaggggg tgcagcccca ggggaaattc        300
agttttggct tcaggtgtgt cgactgtgcc ttggggacct tctccagggg ccacgacggc        360
cactgcaaac cttggacaga ctgcacccag tttgggtttc tcaccgtgtt ccctggaaac        420
aagacccaca acgccgtgtg cgtcccaggg tccccgccgg cagaggtgcc cagggattgt        480
ggttgtaagc cttgcatatg tacagtccca gaagtatcat ctgtcttcat cttcccccca        540
aagcccaagg atgtgctcac cattactctg actcctaagg tcacgtgtgt tgtggtagac        600
atcagcaagg atgatcccga ggtccagttc agctggtttg tagatgatgt ggaggtgcac        660
acagctcaga cgcaaccccg ggaggagcag ttcaacagca ctttccgctc agtcagtgaa        720
cttcccatca tgcaccagga ctggctcaat ggcaaggagt tcaaatgcag ggtcaacagt        780
gcagctttcc ctgcccccat cgagaaaacc atctccaaaa ccaaaggcag accgaaggct        840
ccacaggtgt acaccattcc acctcccaag gagcagatgg ccaaggataa agtcagtctg        900
acctgcatga taacagactt cttccctgaa gacattactg tggagtggca gtggaatggg        960
cagccagcgg agaactacaa gaacactcag cccatcatga cacgaatgg ctcttacttc       1020 gtctacagca agctcaatgt gcagaagagc aactgggagg caggaaatac tttcacctgc       1080
tctgtgttac atgagggcct gcacaaccac catactgaga agagcctctc ccactctcct       1140
gggaaa                                                                   1146
```

<210> SEQ ID NO 68
<211> LENGTH: 1200
<212> TYPE: DNA
<213> ORGANISM: Artificial Sequence
<220> FEATURE:
<223> OTHER INFORMATION: Nucleotide encoding hGITR-EGFP

<400> SEQUENCE: 68

```
atggcacagc acggggcgat gggcgcgttt cgggccctgt gcggcctggc gctgctgtgc         60
gcgctcagcc tgggtcagcg ccccaccggg ggtcccgggt gcggccctgg gcgcctcctg        120
cttgggacgg gaacggacgc gcgctgctgc cgggttcaca cgacgcgctg ctgccgcgat        180
tacccgggcg aggagtgctg ttccgagtgg gactgcatgt gtgtccagcc tgaattccac        240
tgcggagacc cttgctgcac gacctgccgg caccacctt gtcccccagg ccaggggta        300 cagtcccagg ggaaattcag ttttggcttc agtgtatcg actgtgcctc ggggaccttc        360
tccgggggcc acgaaggcca ctgcaaacct tggacagact gcacccagtt cgggtttctc        420
actgtgttcc ctgggaacaa gacccacaac gctgtgtgcg tcccagggtc cccgccggca        480
gagatggtga gcaagggcga ggagctgttc accggggtgg tgcccatcct ggtcgagctg        540
gacggcgacg taaacggcca caagttcagc gtgtccggcg agggcgaggg cgatgccacc        600
tacggcaagc tgaccctgaa gttcatctgc accaccggca agctgcccgt gccctggccc        660
accctcgtga ccaccctgac ctacggcgtg cagtgcttca gccgctaccc cgaccacatg        720
aagcagcacg acttcttcaa gtccgccatg cccgaaggct acgtccagga gcgcaccatc        780
ttcttcaagg acgacggcaa ctacaagacc cgcgccgagg tgaagttcga gggcgacacc        840
ctggtgaacc gcatcgagct gaagggcatc gacttcaagg aggacggcaa catcctgggg        900
cacaagctgg agtacaacta caacagccac aacgtctata tcatggccga caagcagaag        960
```

```
aacggcatca aggtgaactt caagatccgc cacaacatcg aggacggcag cgtgcagctc      1020
gccgaccact accagcagaa caccccatc ggcgacggcc ccgtgctgct gcccgacaac      1080
cactacctga gcacccagtc cgccctgagc aaagacccca acgagaagcg cgatcacatg      1140
gtcctgctgg agttcgtgac cgccgccggg atcactctcg gcatggacga gctgtacaag      1200

<210> SEQ ID NO 69
<211> LENGTH: 1182
<212> TYPE: DNA
<213> ORGANISM: Artificial Sequence
<220> FEATURE:
<223> OTHER INFORMATION: Nucleotide encoding cynoGITR-EGFP

<400> SEQUENCE: 69
atgtgtgcgt gcgggaccct gtgctgcctg gcgctgctgt gtgcggccag cctgggtcag        60
cgccccaccg ggggtcccgg gtgcggccct gggcgcctcc tgctcgggac gggaaaggac       120
gcacgctgct gccgcgttca cccgacgcgc tgctgccgcg attaccagag cgaggagtgc       180
tgctccgagt gggactgcgt gtgtgtccag cctgaattcc actgcggaga cccttgctgc       240
acgacctgcc agcaccaccc ttgcccctca ggccaggggg tgcagcccca ggggaaattc       300
agttttggct tcaggtgtgt cgactgtgcc ttggggacct tctccagggg ccacgacggc       360
cactgcaaac cttggacaga ctgcacccag tttgggtttc tcaccgtgtt ccctggaaac       420
aagacccaca cgccgtgtg cgtcccaggg tccccgccgg cagagatggt gagcaagggc       480
gaggagctgt tcaccggggt ggtgcccatc ctggtcgagc tggacggcga cgtaaacggc       540
cacaagttca gcgtgtccgg cgagggcgag ggcgatgcca cctacggcaa gctgaccctg       600
aagttcatct gcaccaccgg caagctgccc gtgccctggc ccaccctcgt gaccaccctg       660
acctacggcg tgcagtgctt cagccgctac cccgaccaca tgaagcagca cgacttcttc       720
aagtccgcca tgcccgaagg ctacgtccag gagcgcacca tcttcttcaa ggacgacggc       780
aactacaaga cccgcgccga ggtgaagttc gagggcgaca ccctggtgaa ccgcatcgag       840
ctgaagggca tcgacttcaa ggaggacggc aacatcctgg ggcacaagct ggagtacaac       900
tacaacagcc acaacgtcta tatcatggcc gacaagcaga gaaacggcat caaggtgaac       960
ttcaagatcc gccacaacat cgaggacggc agcgtgcagc tcgccgacca ctaccagcag      1020 aacacccca tcggcgacgg ccccgtgctg ctgcccgaca accactacct gagcacccag      1080
tccgccctga gcaaagaccc caacgagaag cgcgatcaca tggtcctgct ggagttcgtg      1140
accgccgccg ggatcactct cggcatggac gagctgtaca ag                        1182

<210> SEQ ID NO 70
<211> LENGTH: 360
<212> TYPE: DNA
<213> ORGANISM: Artificial Sequence
<220> FEATURE:
<223> OTHER INFORMATION: Nucleotide encoding 3E2 VH

<400> SEQUENCE: 70
caggtccaac tgcaggagtc aggccctggg atactgcagc cctcccagac cctcagtctg        60
acttgttctt tctctgggtt ttcactgagc acttttggta tgggtgtagg ctggattcgt       120
cagccttcag ggaagggtct ggaatggctg gtactcattt tatggaatga tattaagtac       180
tataacccag ccctgaagag cctgctcaca gtctccaagg atacctccaa caaccaggtt       240
ttcctcaaga tcgccagtgt ggacaccgca gatactgcca catactactg tgctcgcgta       300
gatggttact acgggtactt cgatgtctgg ggcacaggga ccacggtcac cgtctcctca       360
```

```
<210> SEQ ID NO 71
<211> LENGTH: 336
<212> TYPE: DNA
<213> ORGANISM: Artificial Sequence
<220> FEATURE:
<223> OTHER INFORMATION: Nucleotide encoding 3E2 VL

<400> SEQUENCE: 71
gatatcgtga tgacccaatc tccactctcc ctgcctgtca gtcttggaga tcaagcctcc        60
atctcttgca gatctagtca gaccattgta catagtaatg gaaacaccta tttagaatgg       120
tatctgcaga aaccaggcca gtctccaaag ctcctaatct acaaagtttc caaccgattt       180
tctggggtcc cagacaggtt cagtggcagt ggatcaggga cagatttcac actcaagatc       240
agcagagtgg aggctgagga tctgggagtt tattactgct ttcaaggttc acatgttccg       300
tggacgttcg gtggaggcac caagctggaa atcaaa                                  336

<210> SEQ ID NO 72
<211> LENGTH: 360
<212> TYPE: DNA
<213> ORGANISM: Artificial Sequence
<220> FEATURE:
<223> OTHER INFORMATION: Nucleotide encoding VHV1

<400> SEQUENCE: 72
caagttactt tacaagaaag cggccctact ttagtgaagc ccacccagac tttaacttta        60
acttgtacct tcagcggctt ctctttaagc accttcggca tgggcgtggg ctggatcaga       120
cagcctcccg gtaagggttt agagtggctg gtgctgattt tatggaacga catcaagtac       180
tacaaccccg ctttaaagtc tttactgacc gtgaccaagg acaccagcaa gaaccaagtt       240
gtgctgacca tcaccaacat ggaccccgtg gacaccgcca catactactg cgctcgtgtg       300
gacggctact acggctactt cgacgtgtgg ggccaaggca ctatggtgac agtgagcagc       360

<210> SEQ ID NO 73
<211> LENGTH: 360
<212> TYPE: DNA
<213> ORGANISM: Artificial Sequence
<220> FEATURE:
<223> OTHER INFORMATION: Nucleotide encoding VHV2

<400> SEQUENCE: 73
caagttcagc tgcaagaaag cggccccaca ctggtgaagc ccacccagac tttaacttta        60
acttgtacct tcagcggctt ctctttaagc accttcggca tgggcgtggg ctggattcgt       120
cagcctagcg gcaagggttt agagtggctg gtgctgattt tatggaacga catcaagtac       180
tacaaccccg ctttaaagtc tttactgacc gtgaccaagg acaccagcaa gaaccaagtt       240
gtgctgacca tcaccaacat ggaccccgtg gacaccgcca cctactattg cgctcgtgtg       300
gacggctact acggctactt cgacgtgtgg ggccaaggta caatggtgac cgtgagcagc       360

<210> SEQ ID NO 74
<211> LENGTH: 360
<212> TYPE: DNA
<213> ORGANISM: Artificial Sequence
<220> FEATURE:
<223> OTHER INFORMATION: Nucleotide encoding VHV3
```

-continued

<400> SEQUENCE: 74

```
caagttcagc tgcaagaaag cggccccaca ctggtgaagc ccacccagac tttaacttta     60
acttgtacct tcagcggctt ctctttaagc accttcggca tgggcgtggg ctggattcgt    120
cagcctagcg gcaagggttt agagtggctg gtgctgattt tatggaacga catcaagtac    180
tacaaccccg ctttaaagtc tttactgacc gtgaccaagg acaccagcaa gaaccaagtt    240
gtgctgacca tcaccaacat ggaccccgtg dacaccgcca cctactattg cgctcgtgtg    300
gacggctact acggctactt cgacgtgtgg ggcaccggta caaccgtgac cgtgagcagc    360
```

```
<210> SEQ ID NO 75
<211> LENGTH: 336
<212> TYPE: DNA
<213> ORGANISM: Artificial Sequence
<220> FEATURE:
<223> OTHER INFORMATION: Nucleotide encoding VLV2
```

<400> SEQUENCE: 75

```
gacatcgtga tgacccagag ccctctgtct ttacccgtta ctttaggaca gcccgctagc     60
atcagctgtc gtagcagcca gaccatcgtg cacagcaacg gcaacaccta tttagagtgg    120
tacttacaga gacccggcca gagccccaag ctgctcatct acaaggtgag caatcgtttc    180
tccggcgtgc ccgatagatt tagcggcagc ggtagcggca ccgactttac tttaaagatc    240
agcagagtgg aggccgagga cgtgggcgtg tactactgct tccaaggtag ccatgtgcct    300
tggaccttcg gcggcggcac caaggtggag atcaag                             336
```

```
<210> SEQ ID NO 76
<211> LENGTH: 336
<212> TYPE: DNA
<213> ORGANISM: Artificial Sequence
<220> FEATURE:
<223> OTHER INFORMATION: Nucleotide encoding VLV3
```

<400> SEQUENCE: 76

```
gacatcgtga tgacccagag cccttttatct ttacccgtta cactgggaca gcccgccagc     60
atcagctgtc gtagcagcca gaccatcgtg cacagcaacg gcaacaccta tttagagtgg    120
tatttacaga gcccggcca gagccccaag ctgctgatct acaaggtgag caatcgtttc    180
agcggcgtgc ccgacagatt cagcggaagc ggcagcggca ccgacttcac tttaaagatc    240
agcagagtgg aggccgagga cgtgggcgtg tactactgct tccaaggtag ccatgtgcct    300
tggaccttcg gaggcggcac caagctggag atcaag                             336
```

```
<210> SEQ ID NO 77
<211> LENGTH: 336
<212> TYPE: DNA
<213> ORGANISM: Artificial Sequence
<220> FEATURE:
<223> OTHER INFORMATION: Nucleotide encoding VLV4
```

<400> SEQUENCE: 77

```
gacatcgtga tgacccagag cccttttatct ttacccgtta cactgggaga ccaggccagc     60
atcagctgtc gtagcagcca gaccatcgtg cacagcaacg gcaacaccta tttagagtgg    120
tatttacaga gcccggcca gagccccaag ctgctgatct acaaggtgag caatcgtttc    180
```

-continued

```
agcggcgtgc ccgacagatt cagcggaagc ggcagcggca ccgacttcac tttaaagatc      240
agcagagtgg aggccgagga cgtgggcgtg tactactgct tccaaggtag ccatgtgcct      300
tggaccttcg gaggcggcac caagctggag atcaag                               336
```

ISOLATED ANTIGEN-BINDING PROTEIN AND APPLICATION THEREOF

CROSS-REFERENCE TO RELATED APPLICATIONS

This application is a National Stage Application and claims priority under 35 U.S.C. § 371 to Patent Cooperation Treaty application PCT/CN2020/102472, filed Jul. 16, 2020, which claims the benefit of Chinese application CN 201910646093.8 filed Jul. 17, 2019. Priority is claimed to these applications and the disclosure of these prior applications is considered part of the disclosure of this application and to the extent allowed the entire contents of the aforementioned applications are incorporated herein.

SEQUENCE LISTING

This application incorporates by reference in its entirety the Sequence Listing entitled "2022 Jan. 13_262790-502844_ST25.txt", is 95,099 bytes in size and was created on Jan. 13, 2022, and filed electronically herewith.

FIELD OF THE INVENTION

The present application relates to the field of biomedicine, and particularly to an isolated antigen-binding protein and an application thereof.

BACKGROUND OF THE INVENTION

GITR is a member of the TNF receptor family. GITR is a type I transmembrane protein with a molecular weight of about 26 kDa, which has 14-28% homology with other molecules in the TNF receptor family (Gurney A L, et al, 1999). GITR is constitutively expressed on Treg at a high level, but expressed on unactivated CD4+ T cells, CD8+ T cells, NK and NKT cells at lower levels. When T cells are activated, GITR is highly expressed in CD4+ T, CD8+ T and NK cells (S. Ronchetti, et al., 2004). The natural ligand of GITR, GITRL, is expressed on APC. After GITRL binds to GITR, it provides costimulatory signals, regulates antigen-specific T cell responses, and strengthens cellular and humoral immunity (Selvakumar Sukumar, et al., 2017).

SUMMARY OF THE INVENTION

The present application provides an isolated antigen-binding protein, having one or more of the following properties: 1) capable of binding to human and monkey-derived GITR proteins at a $K_D$ value of $7\times10^{-12}$ M or below, wherein the $K_D$ value is measured by BLI method; 2) capable of stimulating immune cell proliferation; 3) capable of stimulating immune cells to secrete IFN-7, wherein the secretion is measured in T cell viability assay; 4) capable of inhibiting tumor growth and/or tumor cell proliferation; 5) capable of activating GITR signaling pathway; 6) capable of inhibiting the binding of GITR to GITRL.

In some embodiments, the isolated antigen-binding protein of the present application comprises at least one CDR in VH whose amino acid sequence is shown in SEQ ID NO: 23.

In some embodiments, the isolated antigen-binding protein of the present application comprises HCDR3 in VH whose amino acid sequence is shown in SEQ ID NO: 23.

In some embodiments, the isolated antigen-binding protein of the present application comprises HCDR2 in VH whose amino acid sequence is shown in SEQ ID NO: 23.

In some embodiments, the isolated antigen-binding protein of the present application comprises HCDR1 in VH whose amino acid sequence is shown in SEQ ID NO: 23.

In some embodiments, the isolated antigen-binding protein of the present application comprises at least one CDR in VL whose amino acid sequence is shown in SEQ ID NO: 24.

In some embodiments, the isolated antigen-binding protein of the present application comprises LCDR1 in VL whose amino acid sequence is shown in SEQ ID NO: 24.

In some embodiments, the isolated antigen-binding protein of the present application comprises LCDR2 in VL whose amino acid sequence is shown in SEQ ID NO: 24.

In some embodiments, the isolated antigen-binding protein of the present application comprises LCDR3 in VL whose amino acid sequence is shown in SEQ ID NO: 24.

In some embodiments, the HCDR3 comprises an amino acid sequence as shown in SEQ ID NO: 4.

In some embodiments, the HCDR1 comprises an amino acid sequence as shown in SEQ ID NO: 2.

In some embodiments, the HCDR2 comprises an amino acid sequence as shown in SEQ ID NO: 3.

In some embodiments, the LCDR1 comprises an amino acid sequence as shown in SEQ ID NO: 10.

In some embodiments, the LCDR2 comprises an amino acid sequence as shown in SEQ ID NO: 11.

In some embodiments, the LCDR3 comprises an amino acid sequence as shown in SEQ ID NO: 12.

In some embodiments, the isolated antigen-binding protein of the present application comprises an antibody or an antigen-binding fragment thereof.

In some embodiments, the antigen-binding fragment comprises Fab, Fab', F(ab)$_2$, Fv fragment, F(ab')$_2$, scFv, di-scFv and/or dAb.

In some embodiments, the antibody is a humanized antibody.

In some embodiments, the isolated antigen-binding protein of the present application competes with a reference antibody for binding to GITR proteins, wherein the reference antibody comprises HCDR1-3 in VH whose amino acid sequence is shown in SEQ ID NO: 23 as well as LCDR1-3 in VL whose amino acid sequence is shown in SEQ ID NO: 24.

In some embodiments, the HCDR1-3 of the reference antibody include amino acid sequences as shown in SEQ ID NO: 2, SEQ ID NO: 3 and SEQ ID NO: 4, respectively, and the LCDR1-3 of the reference antibody include amino acid sequences as shown in SEQ ID NO: 10, SEQ ID NO: 11 and SEQ ID NO: 12, respectively.

In some embodiments, a light chain variable region of the reference antibody comprises an amino acid sequence as shown in SEQ ID NO: 24; and a heavy chain variable region of the reference antibody comprises an amino acid sequence as shown in SEQ ID NO: 23.

In some embodiments, a light chain of the reference antibody comprises an amino acid sequence as shown in any one of SEQ ID NOs: 64, 46-48; and a heavy chain of the reference antibody comprises an amino acid sequence as shown in any one of SEQ ID NOs: 63, 43-45.

In some embodiments, the VL comprises framework regions L-FR1, L-FR2, L-FR3, and L-FR4.

In some embodiments, a C-terminus of the L-FR1 is directly or indirectly linked to an N-terminus of the LCDR1, and the L-FR1 comprises an amino acid sequence as shown in SEQ ID NO: 39.

In some embodiments, the L-FR1 comprises an amino acid sequence as shown in any one of SEQ ID NOs: 13, 30, 34.

In some embodiments, the L-FR2 is located between the LCDR1 and the LCDR2, and the L-FR2 comprises an amino acid sequence as shown in SEQ ID NO: 40.

In some embodiments, the L-FR2 comprises an amino acid sequence as shown in any one of SEQ ID NOs: 14, 31.

In some embodiments, the L-FR3 is located between the LCDR2 and the LCDR3, and the L-FR3 comprises an amino acid sequence as shown in SEQ ID NO:41.

In some embodiments, the L-FR3 comprises an amino acid sequence as shown in any one of SEQ ID NOs: 15, 32.

In some embodiments, an N-terminus of the L-FR4 is linked to a C-terminus of the LCDR3, and the L-FR4 comprises an amino acid sequence as shown in SEQ ID NO: 42.

In some embodiments, the L-FR4 comprises an amino acid sequence as shown in any one of SEQ ID NOs: 16, 33.

In some embodiments, the VL comprises an amino acid sequence as shown in SEQ ID NO: 24.

In some embodiments, the VL comprises an amino acid sequence as shown in any one of SEQ ID NOs: 9, 20-22.

In some embodiments, the isolated antigen-binding protein of the present application comprises an antibody light chain constant region, and the antibody light chain constant region comprises a human Igκ constant region.

In some embodiments, the antibody light chain constant region comprises an amino acid sequence as shown in SEQ ID NO: 55.

In some embodiments, the isolated antigen-binding protein of the present application comprises an antibody light chain LC, and the LC comprises an amino acid sequence as shown in any one of SEQ ID NOs: 64, 46-48.

In some embodiments, the VH comprises framework regions H-FR1, H-FR2, H-FR3, and H-FR4.

In some embodiments, a C-terminus of the H-FR1 is directly or indirectly linked to an N-terminus of the HCDR1, and the H-FR1 comprises an amino acid sequence as shown in SEQ ID NO: 35.

In some embodiments, the H-FR1 comprises an amino acid sequence as shown in any one of SEQ ID NOs: 5, 25, 29.

In some embodiments, the H-FR2 is located between the HCDR1 and the HCDR2, and the H-FR2 comprises an amino acid sequence as shown in SEQ ID NO: 36.

In some embodiments, the H-FR2 comprises an amino acid sequence as shown in any one of SEQ ID NOs: 6, 26.

In some embodiments, the H-FR3 is located between the HCDR2 and the HCDR3, and the H-FR3 comprises an amino acid sequence as shown in SEQ ID NO: 37.

In some embodiments, the H-FR3 comprises an amino acid sequence as shown in any one of SEQ ID NOs: 7, 27.

In some embodiments, an N-terminus of the H-FR4 is linked to a C-terminus of the HCDR3, and the H-FR4 comprises an amino acid sequence as shown in SEQ ID NO: 38.

In some embodiments, the H-FR4 comprises an amino acid sequence as shown in any one of SEQ ID NOs: 8, 28.

In some embodiments, the VH comprises an amino acid sequence as shown in SEQ ID NO: 23.

In some embodiments, the VH comprises an amino acid sequence as shown in any one of SEQ ID NOs: 1, 17-19.

In some embodiments, the isolated antigen-binding protein of the present application comprises an antibody heavy chain constant region, and the antibody heavy chain constant region is derived from a human IgG heavy chain constant region.

In some embodiments, the antibody heavy chain constant region is derived from a human IgG1 heavy chain constant region.

In some embodiments, the antibody heavy chain constant region comprises an amino acid sequence as shown in SEQ ID NO: 53.

In some embodiments, the isolated antigen-binding protein of the present application comprises an antibody heavy chain HC, and the HC comprises an amino acid sequence as shown in any one of SEQ ID NOs: 63, 43-45.

In another aspect, the present application also provides one or more isolated nucleic acid molecules, which encode the isolated antigen-binding protein of the present application.

In another aspect, the present application also provides a vector, which comprises the nucleic acid molecule of the present application.

In another aspect, the present application also provides a cell, which comprises the nucleic acid molecule of the present application or the vector of the present application.

In another aspect, the present application also provides a method for preparing the isolated antigen-binding protein of the present application, which comprises culturing the cell of the present application under conditions allowing the expression of the isolated antigen-binding protein of the present application.

In another aspect, the present application also provides a pharmaceutical composition, which comprises the isolated antigen-binding protein of the present application, the nucleic acid molecule of the present application, the vector of the present application and/or the cell of the present application, as well as optionally a pharmaceutically acceptable adjuvant.

In another aspect, the present application also provides a use of the isolated antigen-binding protein of the present application, the nucleic acid molecule of the present application, the vector of the present application, the cell of the present application and/or the pharmaceutical composition of the present application in the preparation of a medicament, which is used for preventing, alleviating and/or treating a tumor.

In another aspect, the present application also provides a method for inhibiting the binding of GITR to a GITR ligand GITRL, which comprises administering the isolated antigen-binding protein of the present application.

In another aspect, the present application also provides a method for preventing, alleviating or treating a tumor, which comprises administering to a subject in need thereof the isolated antigen-binding protein of the present application.

In another aspect, the present application also provides a method for activating GITR, which comprises administering the isolated antigen-binding protein of the present application.

Those skilled in the art can easily perceive other aspects and advantages of the present application from the detailed description below. In the following detailed description, only exemplary embodiments of the present application are shown and described. As those skilled in the art will recognize, the content of the present application enables those skilled in the art to make changes to the disclosed specific embodiments without departing from the spirit and scope of the invention involved in the present application. Correspondingly, the drawings and descriptions in the specification of the present application are merely exemplary, rather than restrictive.

BRIEF DESCRIPTION OF THE DRAWINGS

The specific features of the invention involved in the present application are shown in the appended claims. The

5

Figures 1, 2:
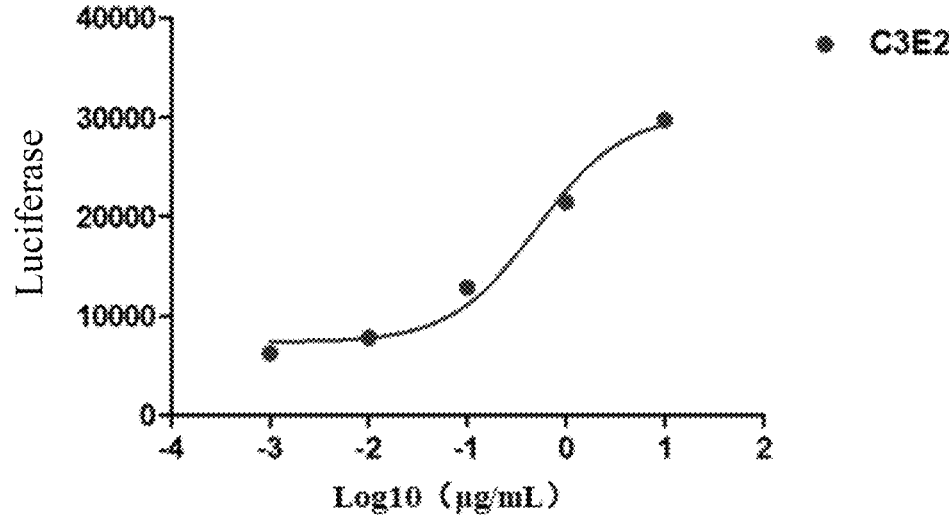
Figure 3:
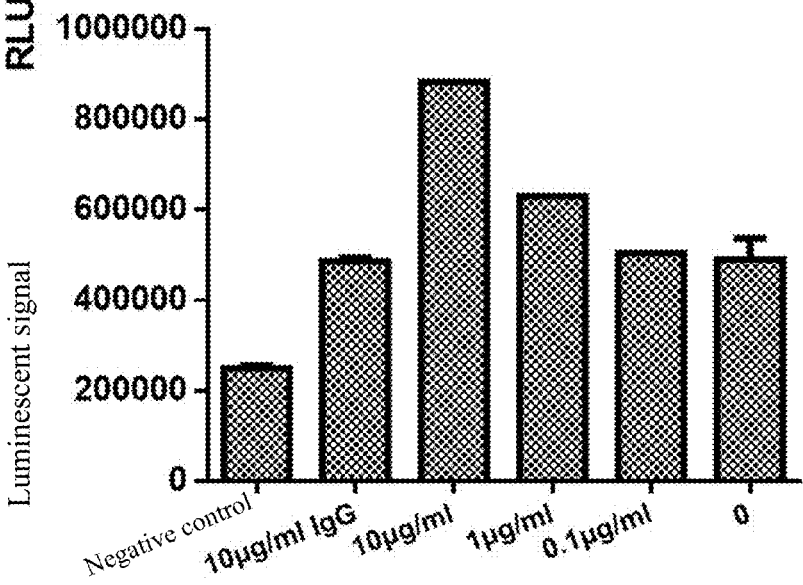
Figure 4:
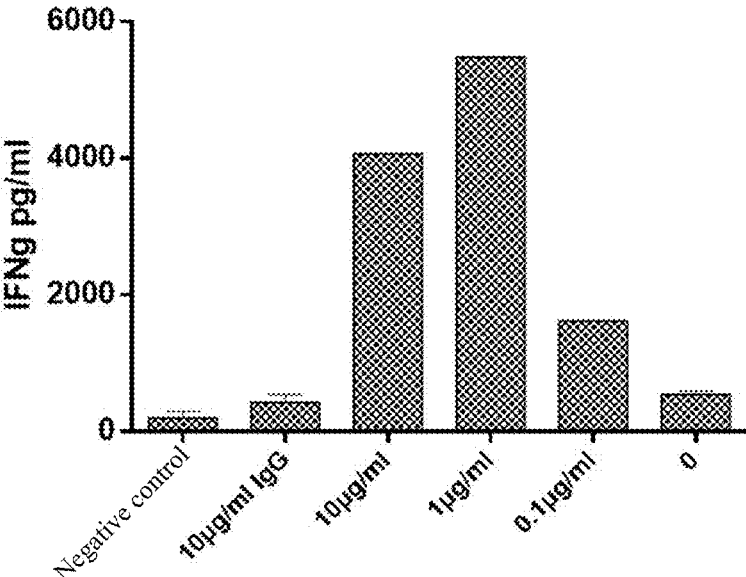
Figure 5:
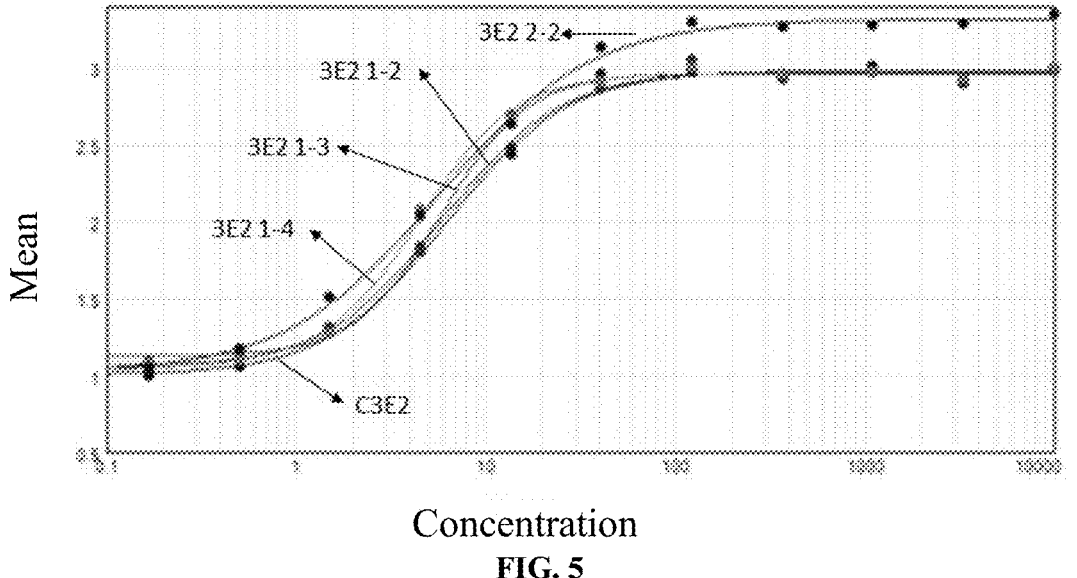
Figure 6:
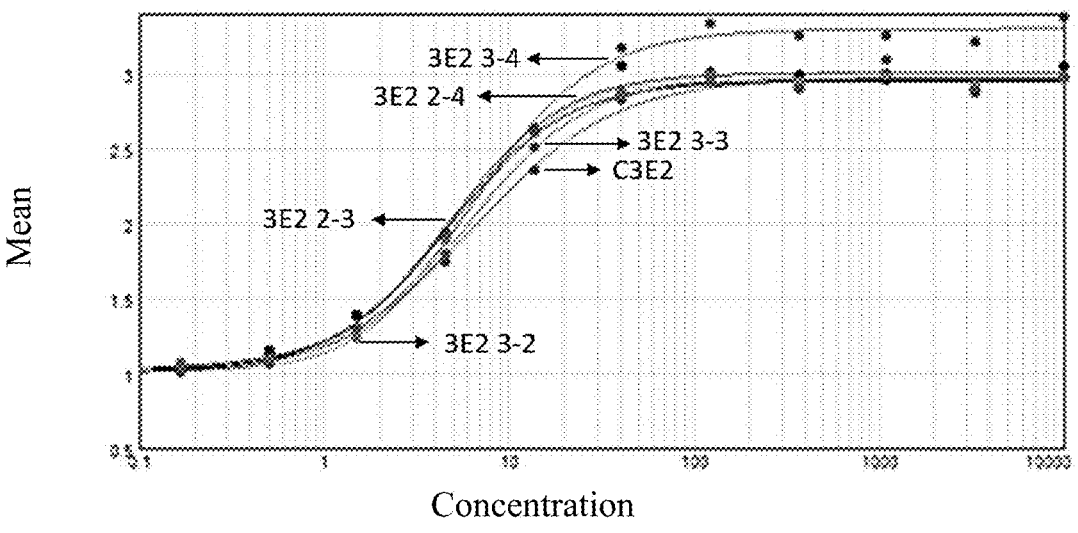
Figure 7:
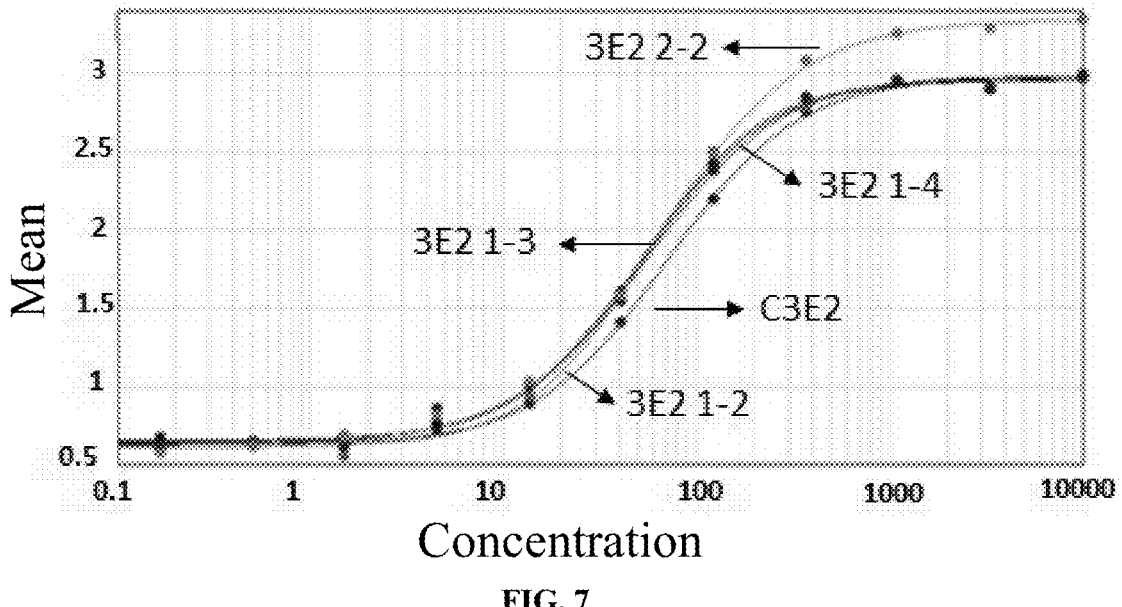
Figure 8:
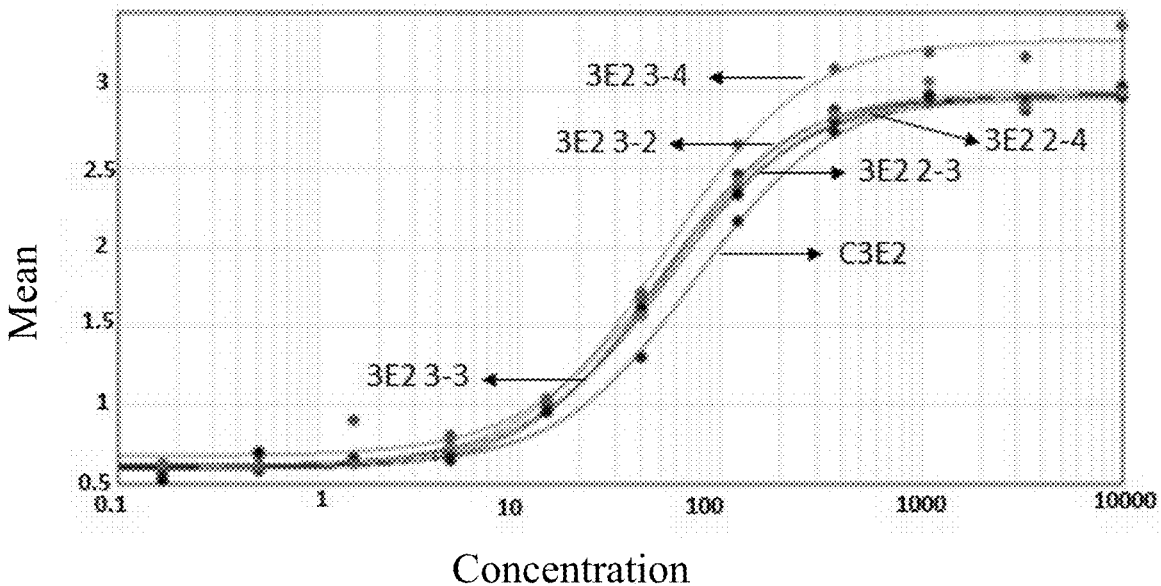
Figure 9:
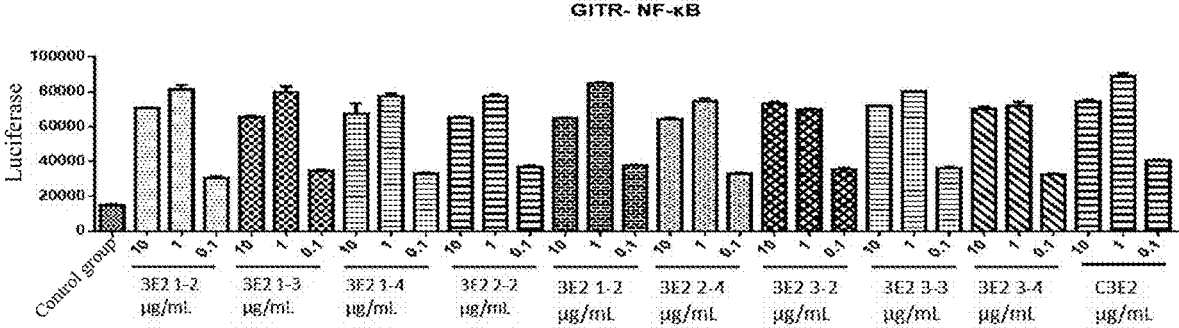
Figure 10:
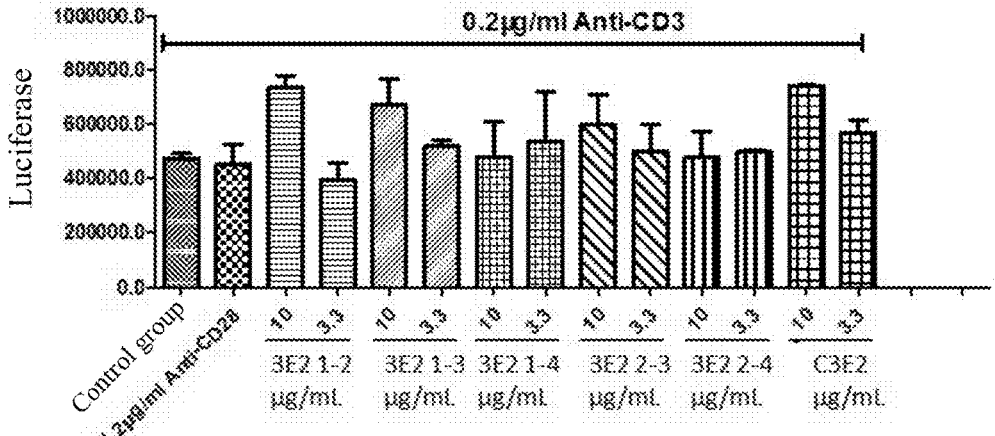
Figure 11:
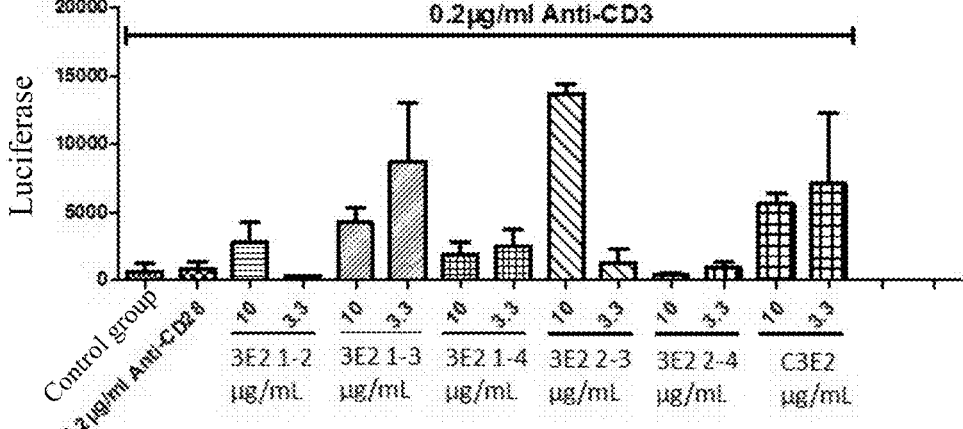
Figure 12:
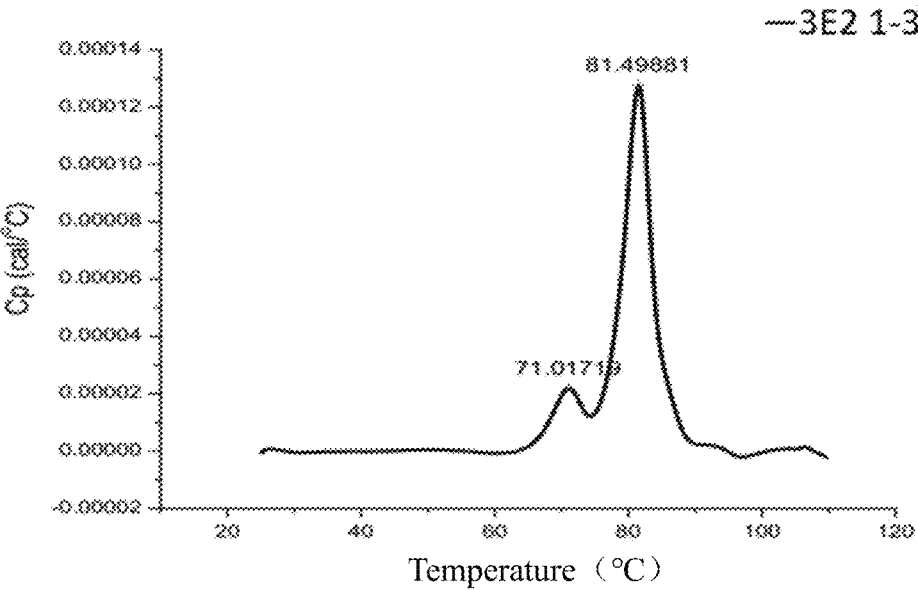
Figure 13:
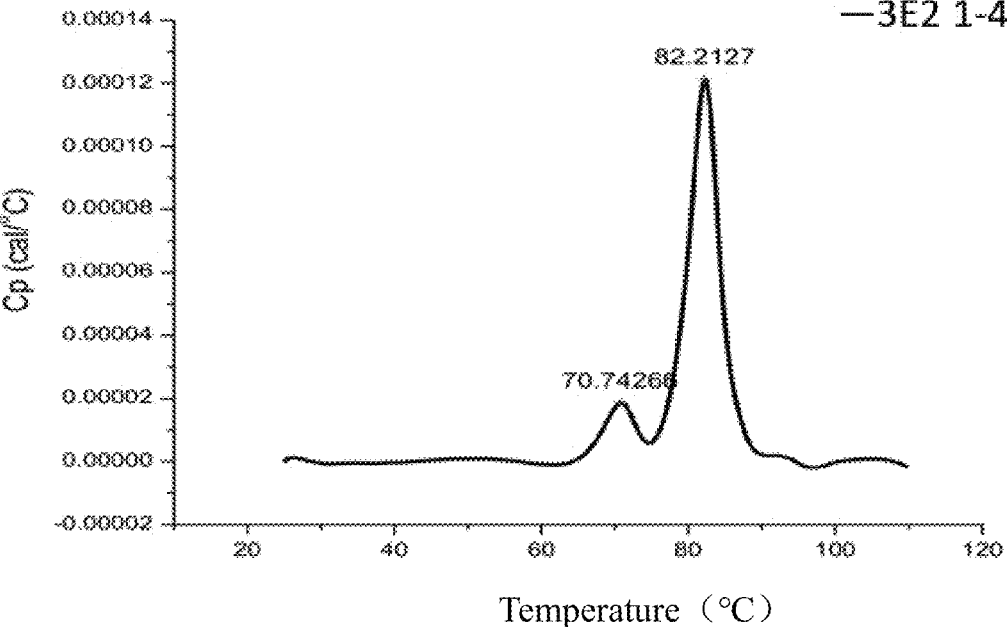
Figure 14:
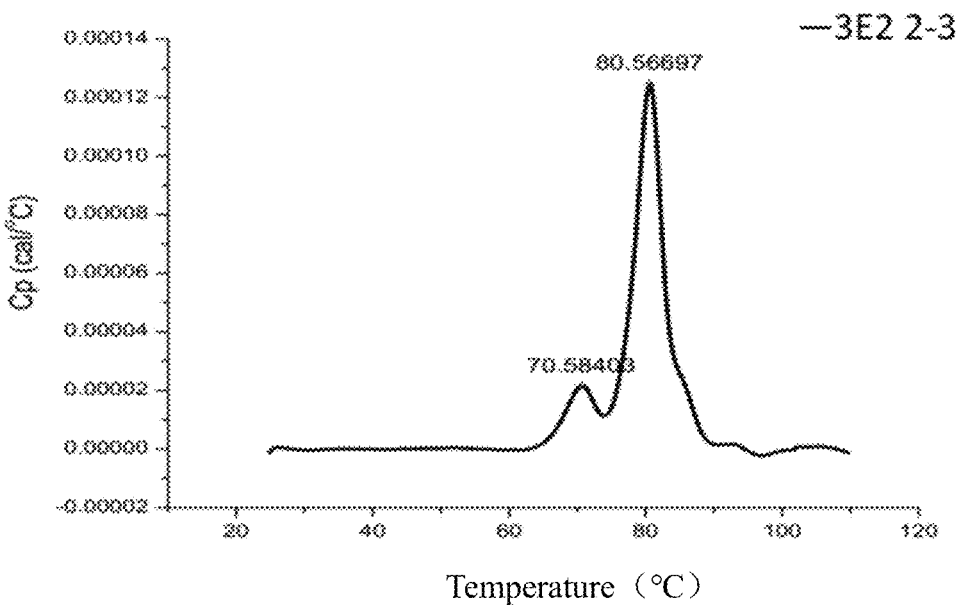
Figure 15:
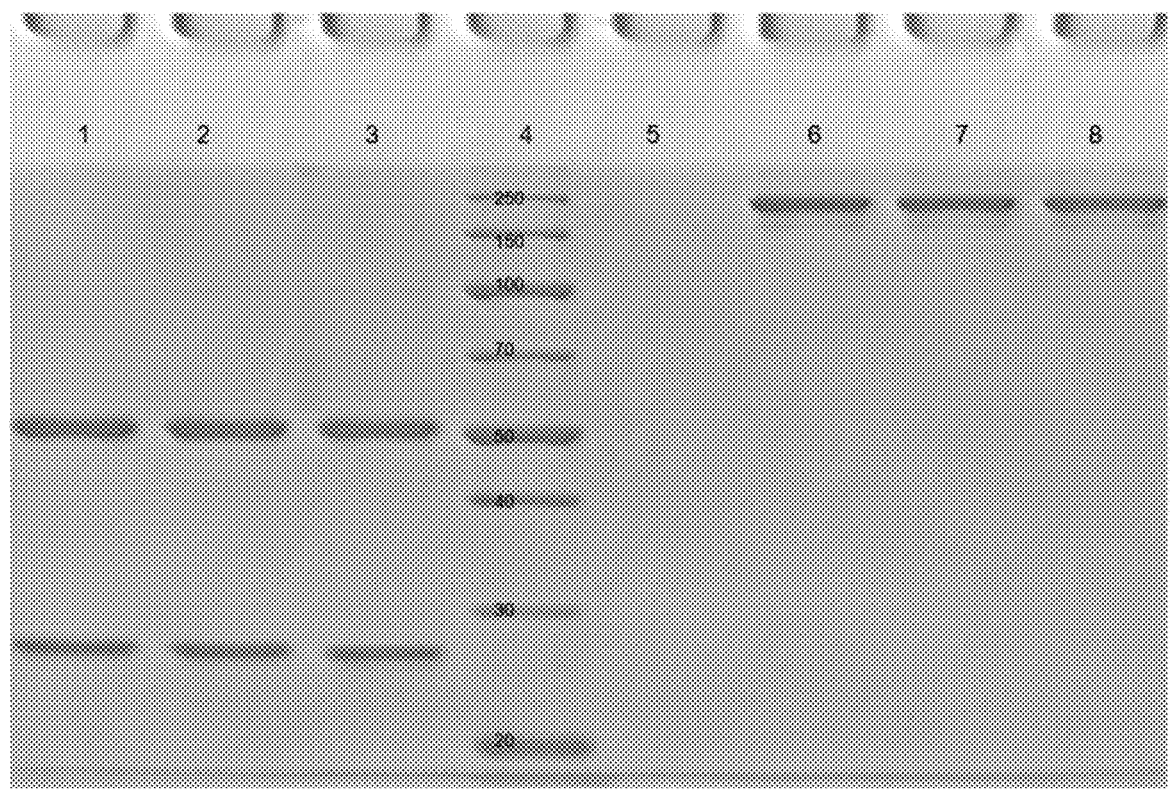
Figure 16:
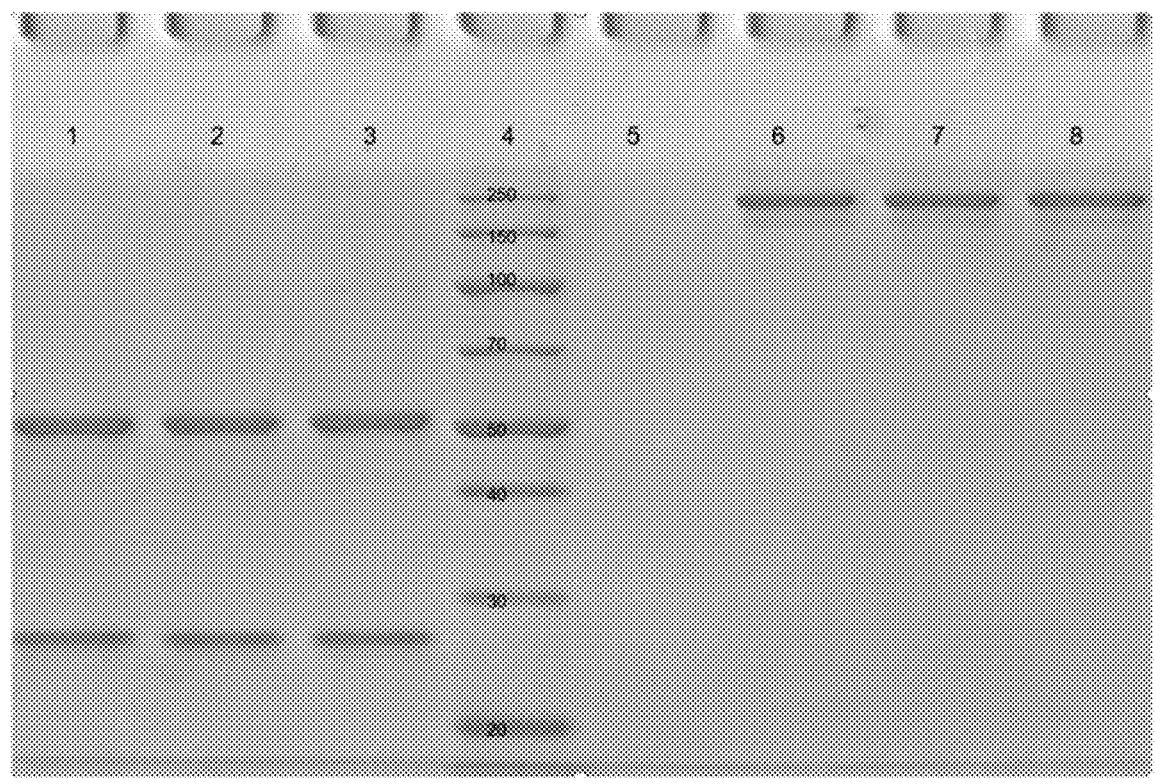
Figure 17:
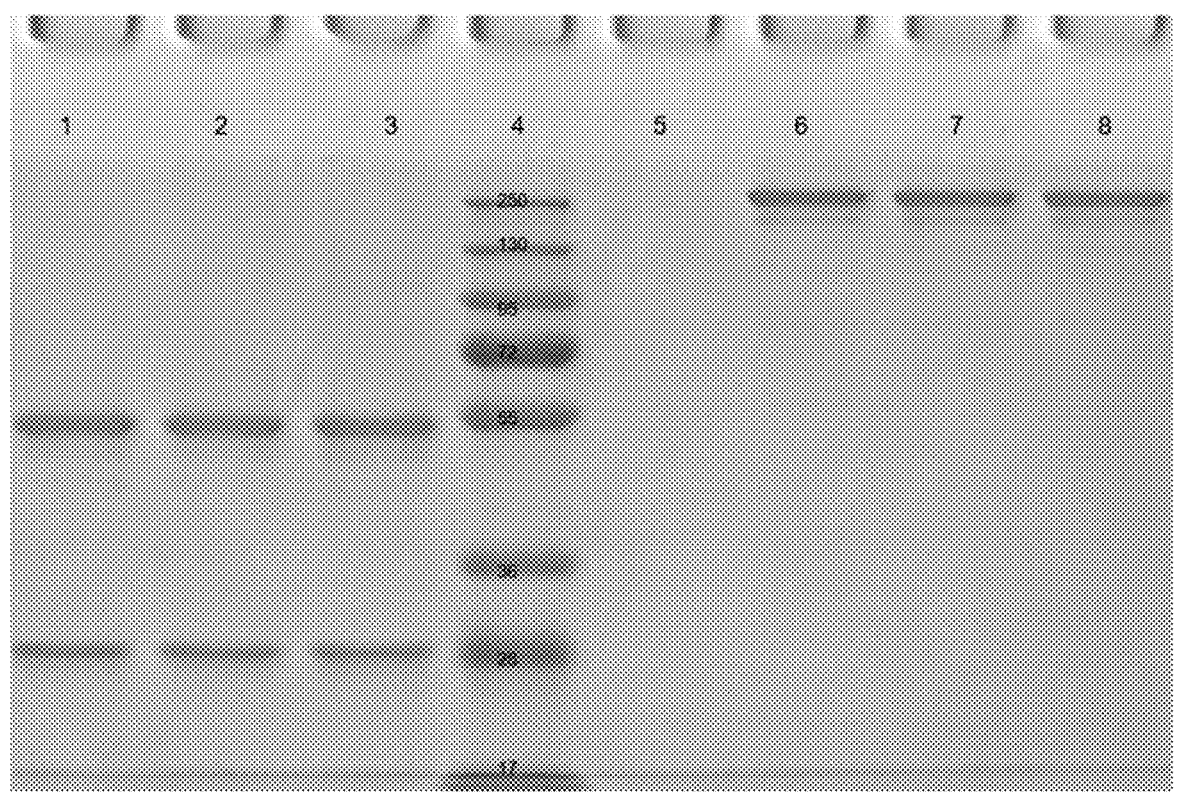
Figure 18:
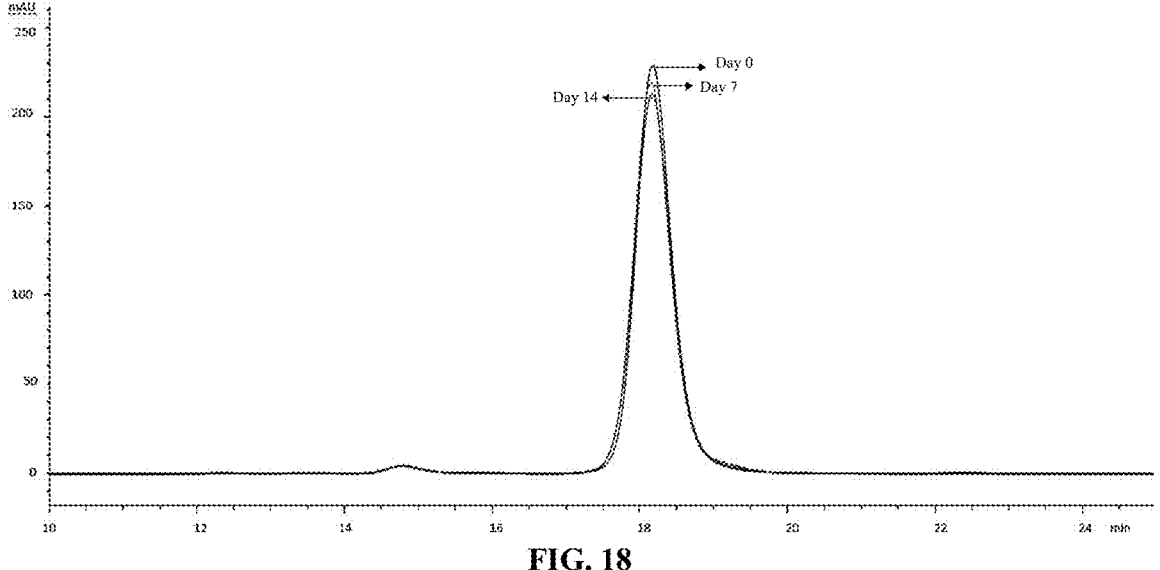
Figure 19:
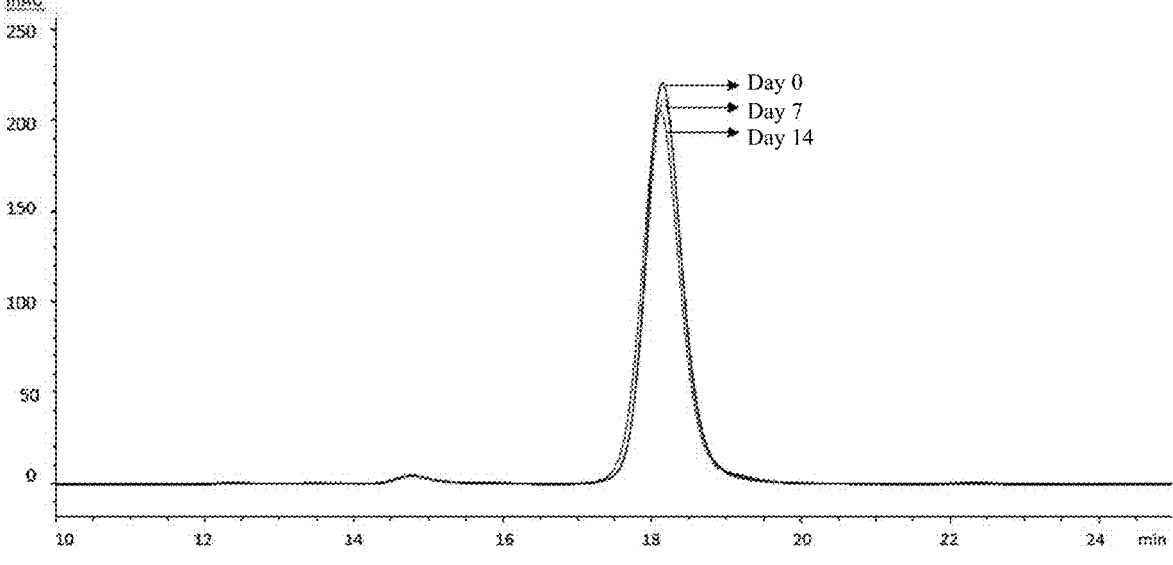
Figure 20:
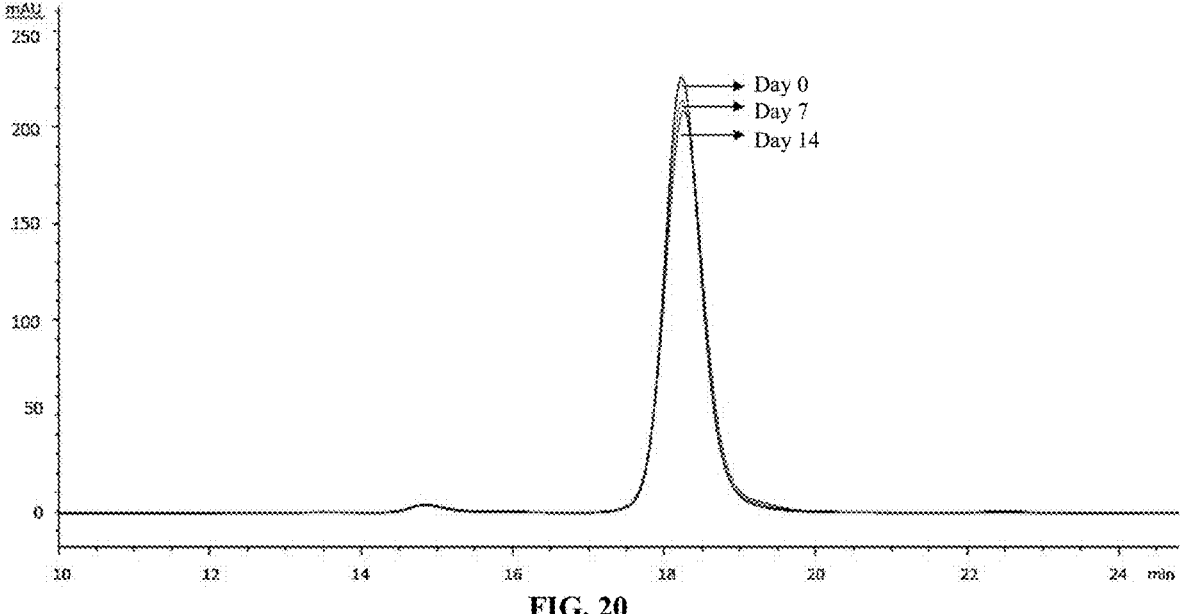

6 characteristics and advantages of the invention involved in the present application can be better understood by referring to the exemplary embodiments and the accompanying drawings described in detail below. A brief description of the drawings is as follows:

FIGS. 1A-1D show the detection results of the ability of the isolated antigen-binding protein of the present application binding to GITR on the cell surface;

FIG. 2 shows the detection results of the activating activity of the isolated antigen-binding protein of the present application;

FIG. 3 shows the T cell proliferation stimulated by the isolated antigen-binding protein of the present application;

FIG. 4 shows the results of the isolated antigen-binding protein of the present application that stimulates immune cells to secrete IFN-γ;

FIG. 5 shows the detection results of the ability of the isolated antigen-binding protein of the present application binding to human-derived GITR proteins;

FIG. 6 shows the detection results of the ability of the isolated antigen-binding protein of the present application binding to human-derived GITR proteins;

FIG. 7 shows the detection results of the ability of the isolated antigen-binding protein of the present application binding to monkey GITR proteins;

FIG. 8 shows the detection results of the ability of the isolated antigen-binding protein of the present application binding to monkey GITR proteins;

FIG. 9 shows the results of downstream signaling pathway activated by the isolated antigen-binding protein of the present application;

FIG. 10 shows T cell proliferation stimulated by the isolated antigen-binding protein of the present application;

FIG. 11 shows the results of the isolated antigen-binding protein of the present application that stimulates immune cells to secrete IFN-γ;

FIG. 12 shows the detection results of the stability of the isolated antigen-binding protein 3E2 1-3 of the present application;

FIG. 13 shows the detection results of the stability of the isolated antigen-binding protein 3E2 1-4 of the present application;

FIG. 14 shows the detection results of the stability of the isolated antigen-binding protein 3E2 2-3 of the present application;

FIG. 15 shows the detection results of polyacrylamide gel electrophoresis (SDS-PAGE) of the isolated antigen-binding protein 3E2 1-3 of the present application;

FIG. 16 shows the detection results of polyacrylamide gel electrophoresis (SDS-PAGE) of the isolated antigen-binding protein 3E2 1-4 of the present application;

FIG. 17 shows the detection results of polyacrylamide gel electrophoresis (SDS-PAGE) of the isolated antigen-binding protein 3E2 2-3 of the present application;

FIG. 18 shows the analysis results of size exclusion chromatography-high performance liquid chromatography (SEC-HPLC) of the isolated antigen-binding protein 3E2 1-3 of the present application;

FIG. 19 shows the analysis results of size exclusion chromatography-high performance liquid chromatography (SEC-HPLC) of the isolated antigen-binding protein 3E2 1-4 of the present application;

FIG. 20 shows the analysis results of size exclusion chromatography-high performance liquid chromatography (SEC-HPLC) of the isolated antigen-binding protein 3E2 2-3 of the present application.

DETAILED DESCRIPTION OF THE EMBODIMENTS

The implementation of the present application will be illustrated in the following specific examples, and other advantages and effects of the present application will be easily known by those familiar with this technology from the content disclosed in the specification.

The following is a further description of the present application: In the present invention, unless otherwise specified, the scientific and technical terms used herein have the meanings commonly understood by those skilled in the art. In addition, protein and nucleic acid chemistry, molecular biology, cell and tissue culture, microbiology, immunology related terms and laboratory procedures used herein are all terms and routine procedures widely used in the corresponding fields. At the same time, in order to better understand the present invention, definitions and explanations of related terms are provided below.

In the present application, the term "isolated" generally refers to being obtained artificially from the native state. If a certain "isolated" substance or ingredient appears in nature, it could be that its natural environment has changed, or the substance has been isolated from the natural environment, or both. For example, there may be a certain nonisolated polynucleotide or polypeptide naturally occurring in a living animal, then the same polynucleotide or polypeptide of a high purity isolated from this natural state is called isolated. The term "isolated" does not exclude being mixed with artificial or synthetic substances, nor excluding the presence of other impure substances with no influences on the activity of the substance.

In the present application, the term "isolated antigen-binding protein" generally refers to a protein with antigen binding ability obtained artificially from the native state. The "isolated antigen-binding protein" may comprise an antigen-binding portion and optionally, a scaffold or framework portion that allows the antigen-binding portion to adopt a conformation that facilitates the antigen-binding portion to bind to the antigen. The antigen-binding protein may comprise, for example, an antibody-derived protein scaffold or alternative protein scaffolds or artificial scaffolds with grafted CDRs or CDR derivatives. Such scaffolds include, but are not limited to, antibody-derived scaffolds containing mutations introduced, for example, to stabilize the three-dimensional structure of the antigen binding protein, and fully synthetic scaffolds containing, for example, biocompatible polymers. See, for example, Korndorfer et al, 2003, Proteins: Structure, Function, and Bioinformatics, 53(1): 121-129 (2003); Roque et al, Biotechnol. Prog. 20:639-654 (2004). In addition, peptide antibody mimics ("PAMs") and scaffolds based on antibody mimics using fibronectin components can be used as the scaffolds. For example, the isolated antigen-binding protein of the present application may be capable of binding to human and monkey-derived GITR proteins at a $K_D$ value of $7\times10^{12}$ or lower, in which the $K_D$ value is measured by BLI method.

In the present application, the term "$K_D$" (similarly, "$K_d$" or "KD") generally refers to the "equilibrium dissociation constant", and refers to the value obtained at equilibrium in a titration measurement, or by dividing the dissociation rate constant ($k_{off}$) by the association rate constant ($k_{on}$). The association rate constant ($k_{on}$), dissociation rate constant ($k_{off}$) and equilibrium dissociation constant ($K_D$) are used to represent the binding affinity of the binding protein (e.g., the isolated antigen-binding protein of the present application) to the antigen. Methods for determining the rate constants of association and dissociation are well known in the art. The use of a fluorescence-based technology provides high sensitivity and the ability to detect samples at equilibrium in physiological buffers. Other experimental approaches and instruments, such as BIAcore (Biomolecular Interaction Analysis), may be used for determination (e.g., instruments available from BIAcore International AB, a GE Healthcare company, Uppsala, Sweden). In addition, the KinExA (Kinetic Exclusion Assay) available from Sapidyne Instruments (Boise, Idaho) can also be used for determination. For example, the $K_D$ value of the isolated antigen-binding protein of the present application binding to human and monkey GITR proteins may be determined by BLI (i.e., Bio-Layer Interferometry) method.

In the present application, the term "immune cells" generally refers to cells that have hematopoietic origin and play a role in immune responses. For example, the immune cells may be selected from one or more of the following group: lymphocytes, natural killer cells and myeloid cells. The lymphocytes may be B cells and/or T cells. The myeloid cells may be selected from one or more of the following groups: monocytes, macrophages, eosinophils, mast cells and basophils.

In the present application, the term "IFN-γ" generally refers to Interferon-γ (IFN-γ), which is a water-soluble dimeric cytokine. For example, the isolated antigen-binding protein of the present application may be capable of stimulating immune cells to secrete IFN-γ, and the secretion can be measured in T cell viability assay.

In the present application, the term "GITR" generally refers to "glucocorticoid-induced TNF-related gene", which is referred as TNF receptor superfamily 18 (TNFRSF18) in the art. The amino acid and nucleic acid sequences of GITR in human and murine forms are described in WO98/06842, which is incorporated herein by reference. Also see GenBank Accession number Q9Y5U5 (amino acid sequence of human) and AF109216 (nucleic acid and amino acid sequences of murine). The amino acid sequence of a particular example of mature human GITR polypeptide is set forth in SEQ ID NO: 49. An exemplary mature GITR protein from Cynomolgus monkey has an amino acid sequence as shown in SEQ ID NO: 51. In addition, the term "GITR" also comprises naturally occurring alleles.

In the present application, the term "GITRL" generally refers to the whole GITR ligand, the soluble GITR ligand and the functionally active portion of the GITR ligand. Also included in the definition of GITRL are naturally occurring allelic variants of GITRL, and GITR ligand variants that differ from the naturally occurring GITR ligand molecules in the amino acid sequences, as well as combinations of such variants, wherein these variants retain the ability of specifically binding to the GITR receptors.

In the present application, the term "activating" generally refers to enabling the target molecule transform from an inactive state to an active state, or from a low-active state to a high-active state. For example, in the present application, the isolated antigen-binding protein of the present application may be capable of activating the GITR signaling pathway, so that the GITR may be transformed from an inactive state to an active state, or from a low-active state to a high-active state.

In the present application, the term "inhibiting" generally refers to reducing the binding activity between a molecule and its specific binding partner (e.g., between a ligand and its specific receptor). For example, the isolated antigen-binding protein of the present application may be capable of inhibiting the binding of GITR to GITR ligand GITRL, that is, blocking the interaction between GITRL and its receptor GITR so as to restore the functional response of T cells from a dysfunctional state to an antigen-stimulated state.

In the present application, the term "variable domain" generally refers to the amino-terminal domain of an antibody heavy chain or light chain. The heavy chain and light chain variable domains may be referred as "VH" and "VL", respectively. These domains are usually the most variable part of the antibody (relative to other antibodies of the same type), and contain antigen-binding sites.

In the present application, the term "variable" generally refers to the fact that there is a great difference in the sequences of some segments of the variable domains between antibodies. V domain mediates the binding of antigen and determines the specificity of a specific antibody to its specific antigen. However, variability is not evenly distributed throughout the variable domain. Instead, it is concentrated in three segments called hypervariable regions (CDRs or HVRs) in the light chain and heavy chain variable domains. The more highly conserved part of the variable domain is referred as framework region (FR). The variable domains of natural heavy chains and light chains each comprises four FR regions, most of which are in β-folded configuration in which they are connected by three CDRs to form a circular connection and in some cases form a part of a β-folded structure. The CDRs in each chain are held together closely by the FR region, and promote the formation of the antigen-binding site of the antibody together with the CDRs from another chain (see Kabat et al, Sequences of Immunological Interest, Fifth Edition, National Institute of Health, Bethesda, Md. (1991)). The constant domains are not directly involved in the binding of antibodies to antigens, but exhibit various effector functions, for example, antibodies are involved in the antibody-dependent cytotoxicity.

In the present application, the term "antibody" generally refers to an immunoglobulin or a fragment or derivative thereof, encompassing any polypeptides that include an antigen binding site, no matter whether it is produced in vitro or in vivo. The term comprises, but is not limited to, polyclonal, monoclonal, mono-specific, multi-specific, non-specific, humanized, single-chain, chimeric, synthetic, recombinant, hybrid, mutated and grafted antibodies. Unless otherwise modified by a term "complete", as in "complete antibody", for the purposes of the present invention, the term "antibody" also comprises antibody fragments, such as Fab, $F(ab')_2$, Fv, scFv, Fd, dAb and other antibody fragments that retain the antigen binding functions (e.g., specifically binding to GITR). In general, such fragments should include antigen-binding domains. The basic 4-chain antibody unit is a heterotetrameric glycoprotein composed of two identical light (L) chains and two identical heavy (H) chains. The IgM antibody is composed of 5 basic heterotetrameric units and another polypeptide called J chain, and contains 10 antigen-binding sites; while the IgA antibody comprises 2-5 basic 4-chain units that can be polymerized with the J chain to form a multivalent combination. In terms of IgG, the 4-chain unit is generally about 150,000 Daltons. Each L chain is linked to the H chain through a covalent disulfide bond, while two H chains are linked to each other through one or more disulfide bonds depending on the isotype of the H chain. Each H and L chain also has regularly spaced intra-chain disulfide bridges. Each H chain has a variable domain (VH) at the N-terminus, which is followed by three constant domains (CH) for each of α and γ chains, and followed by four CH domains for and F isotypes. Each L chain has a variable domain (VL) at the N-terminus, and has a constant domain at the other terminus. VL corresponds to VH, and CL corresponds to the first constant domain (CH1) of the heavy chain. Specific amino acid residues are considered to form an interface between the light chain and heavy chain variable domains. VH is paired with VL to form a single antigen-binding site. For the structures and properties of different kinds of antibodies, see for example Basic and Clinical Immunology, 8th Edition, Daniel P. Sties, Abba I. Terr and Tristram G. Parsolw (eds), Appleton & Lange, Norwalk, Conn., 1994, Page 71 and Chapter 6. L chains from any vertebrate species can be classified into one of two distinct types based on the amino acid sequence of their constant domains, called kappa and lambda. Depending on the amino acid sequence of its heavy chain (CH) constant domain, immunoglobulin can be classified into different types or isotypes. There are five types of immunoglobulin: IgA, IgD, IgE, IgG and IgM, which have heavy chains named α, δ, ε, γ and μ, respectively. Based on the relatively small differences in terms of CH sequence and function, the γ and α types are further divided into sub-types. For example, human expresses the following subtypes: IgG1, IgG2A, IgG2B, IgG3, IgG4, IgA1 and IgK1.

In the present application, the term "CDR" generally refers to an area of an antibody variable domain, of which the sequence is highly variable and/or forms a structure-defining ring. In general, an antibody comprises six CDRs; three in VH (HCDR1, HCDR2, HCDR3), and three in VL (LCDR1, LCDR2, LCDR3). In native antibodies, HCDR3 and LCDR3 exhibit the most diversity of the six CDRs, and in particular, HCDR3 is considered to play a special role in conferring a fine specificity to the antibody. See, for example, Xu et al, Immunity 13:37-45 (2000); Johnson and Wu, in Methods in Molecular Biology 248:1-25 (Lo, ed., Human Press, Totowa, N.J., 2003). In fact, naturally occurring camel antibodies only composed of heavy chains function normally and are stable in the absence of light chains. See, for example, Hamers-Casterman et al., Nature 363:446-448 (1993); Sheriff et al, Nature Struct. Biol. 3:733-736 (1996).

In the present application, the term "FR" generally refers to the more highly conserved portion of the variable domain of an antibody, which is referred to as the framework region. Generally, the variable domains of natural heavy chains and light chains each comprises four FR regions, i.e., four in VH (H-FR1, H-FR2, H-FR3, and H-FR4), and four in VL (L-FR1, L-FR2, L-FR3, and L-FR4). For example, the VL of the isolated antigen-binding protein of the present application may comprise framework regions L-FR1, L-FR2, L-FR3, and L-FR4. The VH of the isolated antigen-binding protein of the present application may comprise framework regions H-FR1, H-FR2, H-FR3, and H-FR4.

In the present application, the term "antigen-binding fragment" generally refers to a fragment having antigen binding activity. In the present application, the antigen-binding fragment may comprise Fab, Fab', F(ab)2, Fv fragment, F(ab')2, scFv, di-scFv and/or dAb.

In the present application, the term "competitive binding" generally refers to that an antibody or a fragment thereof interferes with the ability of another antibody (e.g., reference antibody) to directly or indirectly bind to a target/antigen (e.g., GITR) through allosterically modulating the another antibody. For example, in the present application, the isolated antigen-binding protein may compete with the reference antibody for binding to GITR protein. In addition, an antibody or a fragment thereof can interfere with the extent to which another antibody or fragment thereof binds to a target. Therefore, no matter whether it may be regarded as the blocking or competition according to the present invention, it can be determined by using a competitive binding assay. A particularly suitable quantitative competition assay uses a FACS-based or AlphaScreen-based method to measure the competition between a labeled (for example, His-labeled, biotinylated, or radiolabeled) antibody or a fragment thereof and another antibody or a fragment thereof in terms of binding to a target. Generally, a competitive antibody or a fragment thereof is, for example, one of the following: binding to a target in a competition test, so that during the test and in the presence of a second antibody or a fragment thereof, the recorded substitution of the isolated antigen-binding protein of the present invention reaches up to 100% of the maximum theoretical substitution obtained from the detected potential blocking antibody or fragment thereof present in a given amount (e.g., being substituted by a cold (e.g., unlabeled) antibody or fragment thereof that needs to be blocked)(for example, in the FACS-based competition test). For example, the competitive antibody or the fragment thereof may have 10% to 100%, for example, 50% to 100% of the recorded substitution.

In the present application, the term "direct linking" is opposite to the term "indirect linking". The term "direct linking" generally refers to direct connection. For example, the direct linking may be a case that the substances are directly linked without spacers. The spacers may be linkers. For example, the linkers may be peptide linkers. The term "indirect linking" generally refers to a case that the substances are not directly linked. For example, the indirect linking may be linking through spacers. For example, in the isolated antigen-binding protein of the present application, the C-terminus of the L-FR1 may be directly or indirectly linked to the N-terminus of the LCDR1.

In the present application, the term "isolated nucleic acid molecules" generally refer to isolated nucleotides, deoxyribonucleotides or ribonucleotides of any length, or analogues thereof isolated from its natural environment or synthesized artificially.

In the present application, the term "vector" generally refers to a nucleic acid delivery vehicle into which a polynucleotide encoding a certain protein can be inserted so as to enable the expression of the protein. The vector may make the genetic elements it carries be expressed in a host cell by transforming, transducing or transfecting the host cell. For example, the vectors include: plasmid; phagemid; Cosmid; artificial chromosomes, such as yeast artificial chromosomes (YAC), bacterial artificial chromosomes (BAC) or P1-derived artificial chromosomes (PAC); phages, such as lambda phages or M13 phages and animal viruses, and the like. The species of animal viruses used as the vector are retrovirus (including lentivirus), adenovirus, adeno-associated virus, herpes virus (e.g., herpes simplex virus), poxvirus, baculovirus, papilloma virus, papovavirus (e.g., SV40). A vector may contain various elements for controlling the expression, including promoter sequences, transcription initiation sequences, enhancer sequences, selective elements and reporter genes. In addition, the vectors may also contain replication initiation sites. The vectors may also probably include ingredients that help its entry into cells, such as virion, lipidosome or protein coat, but not only these substances.

In the present application, the term "cells" generally refers to a single cell, cell line, or cell culture that can be or has been a recipient of a subject's plasmid or vectors, which comprises the nucleic acid molecules of the present invention or the vectors of the present invention. The cells may comprise the offspring of a single cell. Due to natural, accidental or intentional mutations, the offspring may not necessarily be exactly the same as the original parent cells (in the form of the total DNA complement or in the genome). The cells may comprise cells transfected with the vectors of the present invention in vitro. The cells may be bacterial cells (e.g., *E. coli*), yeast cells, or other eukaryotic cells, such as COS cells, Chinese Hamster Ovary (CHO) cells, HeLa cells, HEK293 cells, COS-1 cells, NS0 cells, or myeloma cells. In some embodiments, the cells are mammal cells. In some embodiments, the mammal cells are HEK293 cells.

In the present application, the term "pharmaceutical composition" generally refers to the composition suitable for administering to patients, e.g., human patients. For example, the pharmaceutical composition of the present application may comprise the isolated antigen-binding protein of the present application, the nucleic acid molecules of the present application, the vectors of the present application and/or the cells of the present application, as well as optionally a pharmaceutically acceptable adjuvant. In addition, the pharmaceutical composition may also include one or more (pharmaceutically effective) carriers, stabilizers, excipients, diluents, solubilizers, surfactants, emulsifiers and/or preservatives and other suitable preparations. The acceptable ingredients of the composition may be non-toxic to the recipient at the dosage and concentration used. The pharmaceutical composition of the present application comprises, but not limited to, liquid, frozen and freeze-dried compositions.

In the present application, the term "pharmaceutically acceptable adjuvant" generally refers to any and all solvents, dispersion media, coatings, isotonic agents and absorption delaying agents that are compatible with the medication, which are generally safe, non-toxic and neither biologically nor otherwise undesirable.

In the present application, the term "tumor" generally refers to neoplasms or solid lesions formed by abnormal cell growth. In the present application, the tumor may be a solid tumor or a hematologic tumor.

In the present application, the term "subject" generally refers to human or non-human animals, including but not limited to cat, dog, horse, pig, cow, sheep, rabbit, mouse, rat, or monkey.

In the present application, the term "include" generally refers to the inclusion of explicitly specified features, but not excluding other elements.

In the present application, the term "about" generally refers to varying in a range of 0.5%-10% above or below a specified value, for example, varying in a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% above or below a specified value.

Isolated Antigen-Binding Protein

In one aspect, the present application provides an isolated antigen-binding protein, which may have one or more of the following properties: 1) capable of binding to human and monkey-derived GITR proteins at a $K_D$ value of $7 \times 10^{-12}$ or lower, wherein the $K_D$ value is measured by BLI method; 2) capable of stimulating immune cell proliferation; 3) capable of stimulating immune cells to secrete IFN-7, wherein the secretion is measured in T cell viability assay; 4) capable of inhibiting tumor growth and/or tumor cell proliferation; 5) capable of activating GITR signaling pathway; 6) capable of inhibiting the binding of GITR to GITRL.

In the present application, the isolated antigen-binding protein of the present application may be capable of binding to human and monkey-derived GITR proteins at a $K_D$ value of $7 \times 10^{-12}$ M or below, wherein the $K_D$ value may be measured by BLI method. For example, the $K_D$ value of the isolated antigen-binding protein of the present application binding to human-derived GITR proteins may be $\leq 7 \times 10^{-12}$ M, $\leq 6 \times 10^{-12}$ M, $5 \times 10^{-12}$ M, $\leq 4 \times 10^{-12}$ M, $\leq 3 \times 10^{-12}$ M, $\leq 2 \times 10^{-12}$ M, $\leq 1 \times 10^{-12}$ M $\leq 0.5 \times 10^{-12}$ M $\leq 0.1 \times 10^{-12}$ M $\leq 0.01 \times 10^{-12}$ M $\leq 0.05 \times 10^{-12}$ M, or $\leq 0.001 \times 10^{-12}$ M. For another example, the $K_D$ value of the isolated antigen-binding protein of the present application binding to monkey-derived GITR proteins may be $\leq 7 \times 10^{-12}$ M, $\leq 6 \times 10^{-12}$ M, $\leq 5 \times 10^{-12}$ M, $\leq 4 \times 10^{-12}$ M, $\leq 3 \times 10^{-12}$ M, $\leq 2 \times 10^{-12}$ M, $\leq 1 \times 10^{-12}$ M, $\leq 0.5 \times 10^{-12}$ M, $\leq 0.1 \times 10^{-12}$ M, $\leq 0.01 \times 10^{-12}$ M, $\leq 0.05 \times 10^{-12}$ M, or $\leq 0.001 \times 10^{-12}$ M. In addition, the $K_D$ value of the isolated antigen-binding protein of the present application binding to murine-derived GITR proteins may be $\leq 7 \times 10^{-12}$ M, $\leq 6 \times 10^{-12}$ M, $\leq 5 \times 10^{-12}$ M, $\leq 4 \times 10^{-12}$ M, $\leq 3 \times 10^{-12}$ M, $\leq 2 \times 10^{-12}$ M, $\leq 1 \times 10^{-12}$ M $\leq 0.5 \times 10^{-12}$ M $\leq 0.1 \times 10^{-12}$ M $\leq 0.01 \times 10^{-12}$ M, $\leq 0.05 \times 10^{-12}$ M, or $0.001 \times 10^{-12}$ M.

In the present application, the $K_D$ value can also be measured by ELISA, competitive ELISA or BIACORE or KINEXA.

In the present application, the isolated antigen-binding protein of the present application is capable of stimulating immune cell proliferation. For example, the isolated antigen-binding protein of the present application may maintain, improve, accelerate or prolong the proliferation, growth and/or survival of immune cells in vivo or in vitro. Any method that can detect cell proliferation, growth and/or survival, such as a cell proliferation test or an epithelial barrier integrity assay, may be used to determine whether the isolated antigen-binding protein of the present application can stimulate immune cell proliferation.

In the present application, the immune cells may be selected from one or more of the following group: lymphocytes, natural killer cells and myeloid cells. The lymphocytes may be B cells and/or T cells. The myeloid cells may be selected from one or more of the following group: monocytes, macrophages, eosinophils, mast cells, basophils and granulocytes.

In the present application, the isolated antigen-binding protein of the present application may be capable of stimulating immune cells to secrete IFN-7, and the secretion may be measured in T cell viability assay. For example, the content of IFN-7 secreted by immune cells may be measured by ELISA, CBA or MSD method.

In the present application, the isolated antigen-binding protein of the present application is capable of inhibiting tumor growth and/or tumor cell proliferation. For example, it may reduce tumor volume by at least about 10%, at least about 20%, at least about 30%, at least about 40%, at least about 50%, at least about 60%, at least about 70%, at least about 80%, at least about 90%, at least about 99% or 100%. For another example, it may reduce the number of tumor cells by at least about 10%, at least about 20%, at least about 30%, at least about 40%, at least about 50%, at least about 60%, at least about 70%, at least about 80%, at least about 90%, at least about 99% or 100%.

In the present application, the isolated antigen-binding protein of the present application is capable of activating GITR signaling pathway, so that the isolated antigen-binding protein of the present application can block the interaction between GITRL and its receptor GITR, thereby restoring the functional response of T cells from a dysfunctional state to an antigen-stimulated state.

In the present application, the isolated antigen-binding protein of the present application is capable of inhibiting the binding of GITR to GITRL, so as to block the interaction between GITRL and its receptor GITR, thereby restoring the functional response of T cells from a dysfunctional state to an antigen-stimulated state.

In the present application, the isolated antigen-binding protein of the present application may comprise at least one CDR in VH whose amino acid sequence is shown in SEQ ID NO: 23. For example, the isolated antigen-binding protein of the present application may comprise HCDR3 in VH whose amino acid sequence is shown in SEQ ID NO: 23. For example, the isolated antigen-binding protein of the present application may comprise HCDR2 in VH whose amino acid sequence is shown in SEQ ID NO: 23. For another example, the isolated antigen-binding protein of the present application may comprise HCDR1 in VH whose amino acid sequence is shown in SEQ ID NO: 23.

It should be noted that, in the present application, CDRs in VL and/or VH of the isolated antigen-binding protein of the present application can be defined according to Kabat.

In the present application, the isolated antigen-binding protein of the present application may comprise at least one CDR in VL whose amino acid sequence is shown in SEQ ID NO: 24. For example, the isolated antigen-binding protein of the present application may comprise LCDR1 in VL whose amino acid sequence is shown in SEQ ID NO: 24. For example, the isolated antigen-binding protein of the present application may comprise LCDR2 in VL whose amino acid sequence is shown in SEQ ID NO: 24. For another example, the isolated antigen-binding protein of the present application may comprise LCDR3 in VL whose amino acid sequence is shown in SEQ ID NO: 24.

In the isolated antigen-binding protein of the present application, the HCDR3 may comprise an amino acid sequence as shown in SEQ ID NO: 4.

In the isolated antigen-binding protein of the present application, the HCDR1 may comprise an amino acid sequence as shown in SEQ ID NO: 2.

In the isolated antigen-binding protein of the present application, the HCDR2 may comprise an amino acid sequence as shown in SEQ ID NO: 3.

In the isolated antigen-binding protein of the present application, the LCDR1 may comprise an amino acid sequence as shown in SEQ ID NO: 10.

In the isolated antigen-binding protein of the present application, the LCDR2 may comprise an amino acid sequence as shown in SEQ ID NO: 11.

In the isolated antigen-binding protein of the present application, the LCDR3 may comprise an amino acid sequence as shown in SEQ ID NO: 12.

In the present application, the isolated antigen-binding protein of the present application may comprise an antibody or an antigen-binding fragment thereof. For example, the isolated antigen-binding protein of the present application may comprise, but not limited to, a recombinant antibody, a monoclonal antibody, a human antibody, a humanized antibody, a chimeric antibody, a bispecific antibody, a single-chain antibody, a diabody, a triabody, a tetrabody, a Fv fragment, a scFv fragment, a Fab fragment, a Fab' fragment, a F(ab')2 fragment and a camelid single-domain antibody.

In the present application, the antibody may be a humanized antibody. In other words, the isolated antigen-binding protein of the present application may be an antibody or a variant, derivative, analog or fragment thereof that immunospecifically binds to a related antigen (e.g., human GITR) and comprises a framework region (FR) that substantially has an amino acid sequence of a human antibody and a complementary determining region (CDR) that substantially has an amino acid sequence of a non-human antibody. In the case of CDR, "substantially" herein means that the amino acid sequence of the CDR is at least 80%, at least 85%, at least 90%, at least 95%, at least 98% or at least 99% identical to the amino acid sequence of the CDR of a non-human antibody. The humanized antibody substantially may comprise at least one and usually two variable domains (Fab, Fab', F(ab')2, FabC, Fv), wherein all of or substantially all of the CDR regions correspond to the CDR regions of non-human immunoglobulin (i.e., antibody), and all of or substantially all of the framework regions are framework regions with consensus sequences of human immunoglobulin. For example, the humanized antibody also comprises at least a portion of an immunoglobulin constant region (e.g., Fc), which is usually a constant region of human immunoglobulin. In some embodiments, the humanized antibody contains at least variable domains of a light chain as well as a heavy chain. The antibody may also include CH1, hinge, CH2, CH3 and CH4 regions of a heavy chain. In some embodiments, the humanized antibody only comprises a humanized light chain. In some embodiments, the humanized antibody only comprises a humanized heavy chain. In specific embodiments, the humanized antibody only comprises a humanized variable domain of a light chain and/or a humanized heavy chain.

In the present application, the antigen-binding fragment may comprise Fab, Fab', F(ab)2, Fv fragment, F(ab')2, scFv, di-scFv and/or dAb.

In the present application, the isolated antigen-binding protein of the present application may compete with a reference antibody for binding to GITR protein, in which the reference antibody may comprise HCDR1-3 in VH whose amino acid sequence is shown in SEQ ID NO: 23 as well as LCDR1-3 in VL whose amino acid sequence is shown in SEQ ID NO: 24.

In the present application, the HCDR1-3 of the reference antibody may comprise amino acid sequences as shown in SEQ ID NO: 2, SEQ ID NO: 3 and SEQ ID NO: 4, respectively, and the LCDR1-3 of the reference antibody may comprise amino acid sequences as shown in SEQ ID NO: 10, SEQ ID NO: 11 and SEQ ID NO: 12, respectively.

In the present application, the light chain variable region of the reference antibody may comprise an amino acid sequence as shown in SEQ ID NO: 24; and the heavy chain variable region of the reference antibody may comprise an amino acid sequence as shown in SEQ ID NO: 23.

In the present application, the light chain of the reference antibody may comprise an amino acid sequence as shown in any one of SEQ ID NOs: 64, 46-48; and the heavy chain of the reference antibody may comprise an amino acid sequence as shown in any one of SEQ ID NOs: 63, 43-45.

In the present application, the VL of the isolated antigen-binding protein of the present application may comprise framework regions L-FR1, L-FR2, L-FR3, and L-FR4.

For example, a C-terminus of the L-FR1 of the isolated antigen-binding protein of the present application may be directly or indirectly linked to an N-terminus of the LCDR1, and the L-FR1 may comprise an amino acid sequence as shown in SEQ ID NO: 39.

DIVMTQSPLSLPVX$_1$LGX$_2$X$_3$ASISC (SEQ ID NO: 39), in which, X$_1$ may be S or T, X$_2$ may be Q or D, X$_3$ may be P or Q.

For example, the L-FR1 of the isolated antigen-binding protein of the present application may comprise an amino acid sequence as shown in any one of SEQ ID NOs: 13, 30, 34.

For example, the L-FR2 of the isolated antigen-binding protein of the present application may be located between the LCDR1 and the LCDR2, and the L-FR2 may comprise an amino acid sequence as shown in SEQ ID NO: 40.

WYLQX$_1$PGQSPKLLIY (SEQ ID NO: 40), in which, X$_1$ may be R or K.

For example, the L-FR2 of the isolated antigen-binding protein of the present application may comprise an amino acid sequence as shown in any one of SEQ ID NOs: 14, 31.

For example, the L-FR3 of the isolated antigen-binding protein of the present application may be located between the LCDR2 and the LCDR3, and the L-FR3 may comprise an amino acid sequence as shown in SEQ ID NO: 41.

GVPDRFSGSGSGTDFTLKISRVEAEDX$_1$GVYYC (SEQ ID NO: 41), in which, X$_1$ may be L or V.

For example, the L-FR3 of the isolated antigen-binding protein of the present application may comprise an amino acid sequence as shown in any one of SEQ ID NOs: 15, 32.

For example, an N-terminus of the L-FR4 of the isolated antigen-binding protein of the present application may be linked to a C-terminus of the LCDR3, and the L-FR4 may comprise an amino acid sequence as shown in SEQ ID NO: 42.

FGGGTKXiEIK (SEQ ID NO: 42), in which, X$_1$ may be V or L.

For example, the L-FR4 of the isolated antigen-binding protein of the present application may comprise an amino acid sequence as shown in any one of SEQ ID NOs: 16, 33.

In the present application, the VL of the isolated antigen-binding protein of the present application may comprise an amino acid sequence as shown in SEQ ID NO: 24.

DIVMTQSPLSLPVX$_1$LGX$_2$X$_3$ASISCRSSQTIVHSN-GNTYLEWYLQX$_4$PGQ
SPKLLIYKVSNRFSGVPDRFSGSGSGTDFTLKISRVE-AEDXsGVYYCFQGSHVPWTFGGG TKX$_6$EIK (SEQ ID NO: 24), in which, X$_1$ may be S or T, X$_2$ may be Q or D, X$_3$ may be P or Q, X$_4$ may be R or K, X$_5$ may be L or V, X$_6$ may be V or L.

For example, the VL of the isolated antigen-binding protein of the present application may comprise an amino acid sequence as shown in any one of SEQ ID NOs: 9, 20-22.

In the present application, the isolated antigen-binding protein of the present application may comprise an antibody light chain constant region, and the antibody light chain constant region may comprise a human Igκ constant region.

In the present application, the antibody light chain constant region of the isolated antigen-binding protein of the present application may comprise an amino acid sequence as shown in SEQ ID NO: 55.

In the present application, the isolated antigen-binding protein of the present application may comprise an antibody light chain LC, and the LC may comprise an amino acid sequence as shown in any one of SEQ ID NOs: 64, 46-48.

In the present application, the VH of the isolated antigen-binding protein of the present application may comprise framework regions H-FR1, H-FR2, H-FR3, and H-FR4.

For example, a C-terminus of the H-FR1 of the isolated antigen-binding protein of the present application is directly or indirectly linked to an N-terminus of the HCDR1, and the H-FR1 may comprise an amino acid sequence as shown in SEQ ID NO: 35.

QVXiLQESGPX$_2$X$_3$X$_4$X$_5$PX$_6$QTLX$_7$LTCX$_8$FSGFSLS (SEQ ID NO: 35), in which, X$_1$ may be T or Q, X$_2$ may be G or T, X$_3$ may be I or L, X$_4$ may be L or V, X$_5$ may be Q or K, X$_6$ may be S or T, X$_7$ may be S or T, X$_8$ may be S or T.

For example, the H-FR1 of the isolated antigen-binding protein of the present application may comprise an amino acid sequence as shown in any one of SEQ ID NOs: 5, 25, 29.

For example, the H-FR2 of the isolated antigen-binding protein of the present application may be located between the HCDR1 and the HCDR2, and the H-FR2 may comprise an amino acid sequence as shown in SEQ ID NO: 36.

WIRQPX$_1$GKGLEWLVLI (SEQ ID NO: 36), wherein, X$_1$ may be P or S.

For example, the H-FR2 of the isolated antigen-binding protein of the present application may comprise an amino acid sequence as shown in any one of SEQ ID NOs: 6, 26.

For example, the H-FR3 of the isolated antigen-binding protein of the present application may be located between the HCDR2 and the HCDR3, and the H-FR3 may comprise an amino acid sequence as shown in SEQ ID NO: 37.

LLTVX$_1$KDTSX$_2$ $_n$QVX$_3$LX$_4$IX$_5$X$_6$X$_7$DX$_8$X$_9$DTATYY-CAR (SEQ ID NO: 37), in which, X$_1$ may be S or T, X$_2$ may be N or K, X$_3$ may be F or V, X$_4$ may be K or T, X$_5$ may be A or T, X$_6$ may be S or N, X$_7$ may be V or M, X$_8$ may be T or P, X$_9$ may be A or V.

For example, the H-FR3 of the isolated antigen-binding protein of the present application may comprise an amino acid sequence as shown in any one of SEQ ID NOs: 7, 27.

For example, an N-terminus of the H-FR4 of the isolated antigen-binding protein of the present application may be linked to a C-terminus of the HCDR3, and the H-FR4 may comprise an amino acid sequence as shown in SEQ ID NO: 38.

WGX$_1$GTX$_2$VTVSS (SEQ ID NO: 38), in which, X$_1$ may be Q or T, X$_2$ may be M or T.

For example, the H-FR4 of the isolated antigen-binding protein of the present application may comprise an amino acid sequence as shown in any one of SEQ ID NOs: 8, 28.

In the present application, the VH of the isolated antigen-binding protein of the present application may comprise an amino acid sequence as shown in SEQ ID NO: 23.

QVX$_1$LQESGPX$_2$X$_3$X$_4$X$_5$PX$_6$QTLX$_7$LTCX$_g$FSGFSL-STFGMGVGWIRQPX$_9$G
KGLEWLVLILWNDIKYYNPALKSLLTVX10KDTSX$_{11}$
NQVX$_{12}$LX$_{13}$IX$_{14}$X$_{15}$X$_{16}$DX$_{17}$X$_{18}$DT
ATYYCARVDGYYGYFDVWGX$_{19}$GTX$_{20}$VTVSS (SEQ ID NO: 23), in which, X$_1$ may be T or Q, X$_2$ may be G or T, X$_3$ may be I or L, X$_4$ may be L or V, X$_5$ may be Q or K, X$_6$ may be S or T, X$_7$ may be S or T, X$_8$ may be S or T, X$_9$ may be P or S, X$_{10}$ may be S or T, X$_{11}$ may be N or K, X$_{12}$ may be F or V, X$_{13}$ may be K or T, X$_{14}$ may be A or T, X$_{15}$ may be S or N, X$_{11}$ may be V or M, X$_{17}$ may be T or P, X$_{18}$ may be A or V, X$_{19}$ may be Q or T, X$_{20}$ may be M or T.

For example, the VH of the isolated antigen-binding protein of the present application may comprise an amino acid sequence as shown in any one of SEQ ID NOs: 1, 17-19.

In the present application, the isolated antigen-binding protein of the present application may comprise an antibody heavy chain constant region, and the antibody heavy chain constant region may be derived from a human IgG heavy chain constant region. In some other embodiments, the isolated antigen-binding protein of the present application may comprise an antibody heavy chain constant region, and the antibody heavy chain constant region may be derived from a human IgG1 heavy chain constant region.

In the present application, the antibody heavy chain constant region of the isolated antigen-binding protein of the present application may comprise an amino acid sequence as shown in SEQ ID NO: 53.

In the present application, the isolated antigen-binding protein of the present application may comprise an antibody heavy chain HC, and the HC may comprise an amino acid sequence as shown in any one of SEQ ID NOs: 63, 43-45.

For example, the L-FR1 of the isolated antigen-binding protein of the present application may comprise an amino acid sequence as shown in SEQ ID NO: 13, L-FR2 may comprise an amino acid sequence as shown in SEQ ID NO: 14, L-FR3 may comprise an amino acid sequence as shown in SEQ ID NO: 15, L-FR4 may comprise an amino acid sequence as shown in SEQ ID NO: 16, and H-FR1 may comprise an amino acid sequence as shown in SEQ ID NO: 5. H-FR2 may comprise an amino acid sequence as shown in SEQ ID NO: 6. H-FR3 may comprise an amino acid sequence as shown in SEQ ID NO: 7. H-FR4 may comprise an amino acid sequence as shown in SEQ ID NO: 8.

For example, the L-FR1 of the isolated antigen-binding protein of the present application may comprise an amino acid sequence as shown in SEQ ID NO: 30, L-FR2 may comprise an amino acid sequence as shown in SEQ ID NO: 31, L-FR3 may comprise an amino acid sequence as shown in SEQ ID NO: 32, L-FR4 may comprise an amino acid sequence as shown in SEQ ID NO: 33, and H-FR1 may comprise an amino acid sequence as shown in SEQ ID NO: 25. H-FR2 may comprise an amino acid sequence as shown in SEQ ID NO: 26. H-FR3 may comprise an amino acid sequence as shown in SEQ ID NO: 27. H-FR4 may comprise an amino acid sequence as shown in SEQ ID NO: 28.

For example, the L-FR1 of the isolated antigen-binding protein of the present application may comprise an amino acid sequence as shown in SEQ ID NO: 30, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 25. H-FR2 may comprise an amino acid sequence as shown in SEQ ID NO: 26. H-FR3 may comprise an amino acid sequence as shown in SEQ ID NO: 27. H-FR4 may comprise an amino acid sequence as shown in SEQ ID NO: 28.

For example, the L-FR1 of the isolated antigen-binding protein of the present application may comprise an amino acid sequence as shown in SEQ ID NO: 34, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 25. H-FR2 may comprise an amino acid sequence as shown in SEQ ID NO: 26. H-FR3 may comprise an amino acid sequence as shown in SEQ ID NO: 27. H-FR4 may comprise an amino acid sequence as shown in SEQ ID NO: 28.

For example, the L-FR1 of the isolated antigen-binding protein of the present application may comprise an amino acid sequence as shown in SEQ ID NO: 30, L-FR2 may comprise an amino acid sequence as shown in SEQ ID NO: 31, L-FR3 may comprise an amino acid sequence as shown in SEQ ID NO: 32, L-FR4 may comprise an amino acid sequence as shown in SEQ ID NO: 33, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28.

For example, the L-FR1 of the isolated antigen-binding protein of the present application may comprise an amino acid sequence as shown in SEQ ID NO: 30, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28.

For example, the L-FR1 of the isolated antigen-binding protein of the present application may comprise an amino acid sequence as shown in SEQ ID NO: 34, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28.

For example, the L-FR1 of the isolated antigen-binding protein of the present application may comprise an amino acid sequence as shown in SEQ ID NO: 30, L-FR2 may comprise an amino acid sequence as shown in SEQ ID NO: 31, L-FR3 may comprise an amino acid sequence as shown in SEQ ID NO: 32, L-FR4 may comprise an amino acid sequence as shown in SEQ ID NO: 33, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28.

For example, the L-FR1 of the isolated antigen-binding protein of the present application may comprise an amino acid sequence as shown in SEQ ID NO: 30, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28.

For example, the L-FR1 of the isolated antigen-binding protein of the present application may comprise an amino acid sequence as shown in SEQ ID NO: 34, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28.

The isolated antigen-binding protein of the present application may comprise an antibody light chain variable region VL and an antibody heavy chain variable region VH. For example, the VL may comprise an amino acid sequence as shown in SEQ ID NO: 9, the VH may comprise an amino acid sequence as shown in SEQ ID NO: 1.

For example, the VL may comprise an amino acid sequence as shown in SEQ ID NO: 20, the VH may comprise an amino acid sequence as shown in SEQ ID NO: 17.

For example, the VL may comprise an amino acid sequence as shown in SEQ ID NO: 21, the VH may comprise an amino acid sequence as shown in SEQ ID NO: 17.

For example, the VL may comprise an amino acid sequence as shown in SEQ ID NO: 22, the VH may comprise an amino acid sequence as shown in SEQ ID NO: 17.

For example, the VL may comprise an amino acid sequence as shown in SEQ ID NO: 20, the VH may comprise an amino acid sequence as shown in SEQ ID NO: 18.

For example, the VL may comprise an amino acid sequence as shown in SEQ ID NO: 21, the VH may comprise an amino acid sequence as shown in SEQ ID NO: 18.

For example, the VL may comprise an amino acid sequence as shown in SEQ ID NO: 22, the VH may comprise an amino acid sequence as shown in SEQ ID NO: 18.

For example, the VL may comprise an amino acid sequence as shown in SEQ ID NO: 20, the VH may comprise an amino acid sequence as shown in SEQ ID NO: 19.

For example, the VL may comprise an amino acid sequence as shown in SEQ ID NO: 21, the VH may comprise an amino acid sequence as shown in SEQ ID NO: 19.

For example, the VL may comprise an amino acid sequence as shown in SEQ ID NO: 22, the VH may comprise an amino acid sequence as shown in SEQ ID NO: 19.

The isolated antigen-binding protein of the present application may comprise an antibody light chain and an antibody heavy chain.

For example, the light chain may comprise an amino acid sequence as shown in SEQ ID NO: 64, the heavy chain may comprise an amino acid sequence as shown in SEQ ID NO: 63.

For example, the light chain may comprise an amino acid sequence as shown in SEQ ID NO: 46, the heavy chain may comprise an amino acid sequence as shown in SEQ ID NO: 43.

For example, the light chain may comprise an amino acid sequence as shown in SEQ ID NO: 47, the heavy chain may comprise an amino acid sequence as shown in SEQ ID NO: 43.

For example, the light chain may comprise an amino acid sequence as shown in SEQ ID NO: 48, the heavy chain may comprise an amino acid sequence as shown in SEQ ID NO: 43.

For example, the light chain may comprise an amino acid sequence as shown in SEQ ID NO: 46, the heavy chain may comprise an amino acid sequence as shown in SEQ ID NO: 44.

For example, the light chain may comprise an amino acid sequence as shown in SEQ ID NO: 47, the heavy chain may comprise an amino acid sequence as shown in SEQ ID NO: 44.

For example, the light chain may comprise an amino acid sequence as shown in SEQ ID NO: 48, the heavy chain may comprise an amino acid sequence as shown in SEQ ID NO: 44.

For example, the light chain may comprise an amino acid sequence as shown in SEQ ID NO: 46, the heavy chain may comprise an amino acid sequence as shown in SEQ ID NO: 45.

For example, the light chain may comprise an amino acid sequence as shown in SEQ ID NO: 47, the heavy chain may comprise an amino acid sequence as shown in SEQ ID NO: 45.

For example, the light chain may comprise an amino acid sequence as shown in SEQ ID NO: 48, the heavy chain may comprise an amino acid sequence as shown in SEQ ID NO: 45.

In the present application, HCDR1-3 of the isolated antigen-binding protein may comprise amino acid sequences as shown in SEQ ID NO: 2, SEQ ID NO: 3 and SEQ ID NO: 4, respectively, and LCDR1-3 may comprise amino acid sequences as shown in SEQ ID NO: 10, SEQ ID NO: 11 and SEQ ID NO: 12, respectively. Where, the L-FR1 of the isolated antigen-binding protein may comprise an amino acid sequence as shown in SEQ ID NO: 13, L-FR2 may comprise an amino acid sequence as shown in SEQ ID NO: 14, L-FR3 may comprise an amino acid sequence as shown in SEQ ID NO: 15, L-FR4 may comprise an amino acid sequence as shown in SEQ ID NO: 16, and H-FR1 may comprise an amino acid sequence as shown in SEQ ID NO: 5. H-FR2 may comprise an amino acid sequence as shown in SEQ ID NO: 6. H-FR3 may comprise an amino acid sequence as shown in SEQ ID NO: 7. H-FR4 may comprise an amino acid sequence as shown in SEQ ID NO: 8. The VL may comprise an amino acid sequence as shown in SEQ ID NO: 9, the VH may comprise an amino acid sequence as shown in SEQ ID NO: 1. The light chain may comprise an amino acid sequence as shown in SEQ ID NO: 64, the heavy chain may comprise an amino acid sequence as shown in SEQ ID NO: 63. For example, the isolated antigen-binding protein may be C3E2.

In the present application, HCDR1-3 of the isolated antigen-binding protein may comprise amino acid sequences as shown in SEQ ID NO: 2, SEQ ID NO: 3 and SEQ ID NO: 4, respectively, and LCDR1-3 may comprise amino acid sequences as shown in SEQ ID NO: 10, SEQ ID NO: 11 and SEQ ID NO: 12, respectively. Where, the L-FR1 of the isolated antigen-binding protein of the present application may comprise an amino acid sequence as shown in SEQ ID NO: 30, L-FR2 may comprise an amino acid sequence as shown in SEQ ID NO: 31, L-FR3 may comprise an amino acid sequence as shown in SEQ ID NO: 32, L-FR4 may comprise an amino acid sequence as shown in SEQ ID NO: 33, and H-FR1 may comprise an amino acid sequence as shown in SEQ ID NO: 25. H-FR2 may comprise an amino acid sequence as shown in SEQ ID NO: 26. H-FR3 may comprise an amino acid sequence as shown in SEQ ID NO: 27. H-FR4 may comprise an amino acid sequence as shown in SEQ ID NO: 28. The VL may comprise an amino acid sequence as shown in SEQ ID NO: 20, the VH may comprise an amino acid sequence as shown in SEQ ID NO: 17. The light chain may comprise an amino acid sequence as shown in SEQ ID NO: 46, the heavy chain may comprise an amino acid sequence as shown in SEQ ID NO: 43. For example, the isolated antigen-binding protein may be 3E2 1-2.

In the present application, HCDR1-3 of the isolated antigen-binding protein may comprise amino acid sequences as shown in SEQ ID NO: 2, SEQ ID NO: 3 and SEQ ID NO: 4, respectively, and LCDR1-3 may comprise amino acid sequences as shown in SEQ ID NO: 10, SEQ ID NO: 11 and SEQ ID NO: 12, respectively. Where, the L-FR1 of the isolated antigen-binding protein of the present application may comprise an amino acid sequence as shown in SEQ ID NO: 30, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 25. H-FR2 may comprise an amino acid sequence as shown in SEQ ID NO: 26. H-FR3 may comprise an amino acid sequence as shown in SEQ ID NO: 27. H-FR4 may comprise an amino acid sequence as shown in SEQ ID NO: 28. The VL may comprise an amino acid sequence as shown in SEQ ID NO: 21, the VH may comprise an amino acid sequence as shown in SEQ ID NO: 17. The light chain may comprise an amino acid sequence as shown in SEQ ID NO: 47, the heavy chain may comprise an amino acid sequence as shown in SEQ ID NO: 43. For example, the isolated antigen-binding protein may be 3E2 1-3.

In the present application, HCDR1-3 of the isolated antigen-binding protein may comprise amino acid sequences as shown in SEQ ID NO: 2, SEQ ID NO: 3 and SEQ ID NO: 4, respectively, and LCDR1-3 may comprise amino acid sequences as shown in SEQ ID NO: 10, SEQ ID NO: 11 and SEQ ID NO: 12, respectively. Where, the L-FR1 of the isolated antigen-binding protein of the present application may comprise an amino acid sequence as shown in SEQ ID NO: 34, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 25. H-FR2 may comprise an amino acid sequence as shown in SEQ ID NO: 26. H-FR3 may comprise an amino acid sequence as shown in SEQ ID NO: 27. H-FR4 may comprise an amino acid sequence as shown in SEQ ID NO: 28. The VL may comprise an amino acid sequence as shown in SEQ ID NO: 22, the VH may comprise an amino acid sequence as shown in SEQ ID NO: 17. The light chain may comprise an amino acid sequence as shown in SEQ ID NO: 48, the heavy chain may comprise an amino acid sequence as shown in SEQ ID NO: 43. For example, the isolated antigen-binding protein may be 3E2 1-4.

In the present application, HCDR1-3 of the isolated antigen-binding protein may comprise amino acid sequences as shown in SEQ ID NO: 2, SEQ ID NO: 3 and SEQ ID NO: 4, respectively, and LCDR1-3 may comprise amino acid sequences as shown in SEQ ID NO: 10, SEQ ID NO: 11 and SEQ ID NO: 12, respectively. Where, the L-FR1 of the isolated antigen-binding protein of the present application may comprise an amino acid sequence as shown in SEQ ID NO: 30, L-FR2 may comprise an amino acid sequence as shown in SEQ ID NO: 31, L-FR3 may comprise an amino acid sequence as shown in SEQ ID NO: 32, L-FR4 may comprise an amino acid sequence as shown in SEQ ID NO: 33, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28. The VL may comprise an amino acid sequence as shown in SEQ ID NO: 20, the VH may comprise an amino acid sequence as shown in SEQ ID NO: 18. The light chain may comprise an amino acid sequence as shown in SEQ ID NO: 46, the heavy chain may comprise an amino acid sequence as shown in SEQ ID NO: 44. For example, the isolated antigen-binding protein may be 3E2 2-2.

In the present application, HCDR1-3 of the isolated antigen-binding protein may comprise amino acid sequences as shown in SEQ ID NO: 2, SEQ ID NO: 3 and SEQ ID NO: 4, respectively, and LCDR1-3 may comprise amino acid sequences as shown in SEQ ID NO: 10, SEQ ID NO: 11 and SEQ ID NO: 12, respectively. Where, the L-FR1 of the isolated antigen-binding protein of the present application may comprise an amino acid sequence as shown in SEQ ID NO: 30, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28. The VL may comprise an amino acid sequence as shown in SEQ ID NO: 21, the VH may comprise an amino acid sequence as shown in SEQ ID NO: 18. The light chain may comprise an amino acid sequence as shown in SEQ ID NO: 47, the heavy chain may comprise an amino acid sequence as shown in SEQ ID NO: 44. For example, the isolated antigen-binding protein may be 3E2 2-3.

In the present application, HCDR1-3 of the isolated antigen-binding protein may comprise amino acid sequences as shown in SEQ ID NO: 2, SEQ ID NO: 3 and SEQ ID NO: 4, respectively, and LCDR1-3 may comprise amino acid sequences as shown in SEQ ID NO: 10, SEQ ID NO: 11 and SEQ ID NO: 12, respectively. Where, the L-FR1 of the isolated antigen-binding protein of the present application may comprise an amino acid sequence as shown in SEQ ID NO: 34, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28. The VL may comprise an amino acid sequence as shown in SEQ ID NO: 22, the VH may comprise an amino acid sequence as shown in SEQ ID NO: 18. The light chain may comprise an amino acid sequence as shown in SEQ ID NO: 48, the heavy chain may comprise an amino acid sequence as shown in SEQ ID NO: 44. For example, the isolated antigen-binding protein may be 3E2 2-4.

In the present application, HCDR1-3 of the isolated antigen-binding protein may comprise amino acid sequences as shown in SEQ ID NO: 2, SEQ ID NO: 3 and SEQ ID NO: 4, respectively, and LCDR1-3 may comprise amino acid sequences as shown in SEQ ID NO: 10, SEQ ID NO: 11 and SEQ ID NO: 12, respectively. Where, the L-FR1 of the isolated antigen-binding protein of the present application may comprise an amino acid sequence as shown in SEQ ID NO: 30, L-FR2 may comprise an amino acid sequence as shown in SEQ ID NO: 31, L-FR3 may comprise an amino acid sequence as shown in SEQ ID NO: 32, L-FR4 may comprise an amino acid sequence as shown in SEQ ID NO: 33, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28. The VL may comprise an amino acid sequence as shown in SEQ ID NO: 20, the VH may comprise an amino acid sequence as shown in SEQ ID NO: 19. The light chain may comprise an amino acid sequence as shown in SEQ ID NO: 46, the heavy chain may comprise an amino acid sequence as shown in SEQ ID NO: 45. For example, the isolated antigen-binding protein may be 3E2 3-2.

In the present application, HCDR1-3 of the isolated antigen-binding protein may comprise amino acid sequences as shown in SEQ ID NO: 2, SEQ ID NO: 3 and SEQ ID NO: 4, respectively, and LCDR1-3 may comprise amino acid sequences as shown in SEQ ID NO: 10, SEQ ID NO: 11 and SEQ ID NO: 12, respectively. Where, the L-FR1 of the isolated antigen-binding protein of the present application may comprise an amino acid sequence as shown in SEQ ID NO: 30, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28. The VL may comprise an amino acid sequence as shown in SEQ ID NO: 21, the VH may comprise an amino acid sequence as shown in SEQ ID NO: 19. The light chain may comprise an amino acid sequence as shown in SEQ ID NO: 47, the heavy chain may comprise an amino acid sequence as shown in SEQ ID NO: 45. For example, the isolated antigen-binding protein may be 3E2 3-3.

In the present application, HCDR1-3 of the isolated antigen-binding protein may comprise amino acid sequences as shown in SEQ ID NO: 2, SEQ ID NO: 3 and SEQ ID NO: 4, respectively, and LCDR1-3 may comprise amino acid sequences as shown in SEQ ID NO: 10, SEQ ID NO: 11 and SEQ ID NO: 12, respectively. Where, the L-FR1 of the isolated antigen-binding protein of the present application may comprise an amino acid sequence as shown in SEQ ID NO: 34, L-FR2 may comprise an amino acid sequence as shown in SEQ ID NO: 14, L-FR3 may comprise an amino acid sequence as shown in SEQ ID NO: 32, L-FR4 may comprise an amino acid sequence as shown in SEQ ID NO: 16, and H-FR1 may comprise an amino acid sequence as shown in SEQ ID NO: 29. H-FR2 may comprise an amino acid sequence as shown in SEQ ID NO: 6. H-FR3 may comprise an amino acid sequence as shown in SEQ ID NO: 27. H-FR4 may comprise an amino acid sequence as shown in SEQ ID NO: 28. The VL may comprise an amino acid sequence as shown in SEQ ID NO: 22, the VH may comprise an amino acid sequence as shown in SEQ ID NO: 19. The light chain may comprise an amino acid sequence as shown in SEQ ID NO: 48, the heavy chain may comprise an amino acid sequence as shown in SEQ ID NO: 45. For example, the isolated antigen-binding protein may be 3E2 3-4.

Nucleic Acid Molecules, Vectors, Cells, Preparation Method and Pharmaceutical Composition In another aspect, the present application also provides one or more isolated nucleic acid molecules, which may encode the isolated antigen-binding protein of the present application. The one or more isolated nucleic acid molecules of the present application may be isolated nucleotides, deoxyribonucleotides or ribonucleotides of any length, or analogues thereof isolated from its natural environment or synthesized artificially, which may encode the isolated antigen-binding protein of the present application.

In another aspect, the present application also provides vectors, which may comprise the nucleic acid molecules of the present application. The vector may make the genetic elements it carries be expressed in a host cell by transforming, transducing or transfecting the host cell. For example, the vector may comprise: plasmid; phagemid; Cosmid; artificial chromosomes, such as yeast artificial chromosomes (YAC), bacterial artificial chromosomes (BAC) or P1-derived artificial chromosomes (PAC); phages, such as lambda phages or M13 phages and animal viruses, and the like. The species of animal viruses used as the vector are retrovirus (including lentivirus), adenovirus, adeno-associated virus, herpes virus (e.g., herpes simplex virus), poxvirus, baculovirus, papilloma virus, papovavirus (e.g., SV40). For another example, the vector may contain various elements for controlling the expression, including promoter sequences, transcription initiation sequences, enhancer sequences, selective elements and reporter genes. In addition, the vector may also contain replication initiation sites. Moreover, the vector may also probably include ingredients that help its entry into cells, such as virion, lipidosome or protein coat, but not only these substances.

In another aspect, the present application also provides cells, which may comprise the nucleic acid molecules of the present application or the vectors of the present application. The cells may comprise the offspring of a single cell. Due to natural, accidental or intentional mutations, the offspring may not necessarily be exactly the same as the original parent cells (in the form of the total DNA complement or in the genome). In some embodiments, the cells may comprise cells transfected with the vectors of the present invention in vitro. In some embodiments, the cells may be bacterial cells (e.g., *E. coli*), yeast cells, or other eukaryotic cells, such as COS cells, Chinese Hamster Ovary (CHO) cells, HeLa cells, HEK293 cells, COS-1 cells, NS0 cells, or myeloma cells. In some embodiments, the cells may be mammal cells. In some embodiments, the mammal cells may be HEK293 cells.

In another aspect, the present application also provides a method for preparing the isolated antigen-binding protein of the present application. The method may comprise culturing the cells of the present application under conditions allowing the expression of the isolated antigen-binding protein of the present application.

In another aspect, the present application also provides a pharmaceutical composition, which may comprise the isolated antigen-binding protein of the present application, the nucleic acid molecules of the present application, the vectors of the present application and/or the cells of the present application, as well as optionally a pharmaceutically acceptable adjuvant.

In some embodiments, the pharmaceutical composition may also include one or more (pharmaceutically effective) carriers, stabilizer, excipients, diluents, solubilizers, surfactants, emulsifiers and/or preservatives and other suitable preparations. The acceptable ingredients of the composition may be non-toxic to the recipient at the dosage and concentration used. The pharmaceutical composition of the present invention comprises, but not limited to, liquid, frozen and freeze-dried compositions.

In some embodiments, the pharmaceutically acceptable adjuvant may comprise any and all solvents, dispersion media, coatings, isotonic agents and absorption delaying agents that are compatible with the medication, which are generally safe, non-toxic and neither biologically nor otherwise undesirable.

In some embodiments, the pharmaceutical composition may be administered parenterally, transdermally, intraperitoneally, intra-arterially, intrathecally and/or intranasally or directly injected into tissues. For example, the pharmaceutical composition may be administered to patients or subjects by means of infusion or injection. In some embodiments, the administration of the pharmaceutical composition may be carried out in different ways, such as intravenous, intraperitoneal, subcutaneous, intramuscular, topical or intradermal administration. In some embodiments, the pharmaceutical composition may be administered incessantly. The incessant (or continuous) administration may be achieved by a small pump system worn by the patient to measure the therapeutic agent flowing into the patient, as described in WO2015/036583.

Use and Application

In another aspect, the present application also provides a use of the isolated antigen-binding protein of the present application, the nucleic acid molecules of the present application, the vectors of the present application, the cells of the present application and/or the pharmaceutical composition of the present application in the preparation of a medicament, which can be used for preventing, alleviating and/or treating a tumor.

In another aspect, the present application also provides a method for preventing, alleviating or treating a tumor, which may comprise administering to a subject in need thereof the isolated antigen-binding protein of the present application.

In another aspect, the isolated antigen-binding protein of the present application, the nucleic acid molecules of the present application, the vectors of the present application, the cells of the present application and/or the pharmaceutical composition of the present application may be used for preventing, alleviating or treating a tumor.

In the present application, the tumor may be solid tumor or hematologic tumor.

In the present application, the subject may comprise human and non-human animals. For example, the subject may comprise, but not limited to, cat, dog, horse, pig, cow, sheep, rabbit, mouse, rat, or monkey.

In another aspect, the present application also provides a method for inhibiting the binding of GITR to a GITR ligand GITRL, which may comprise administering the isolated antigen-binding protein of the present application. For example, after administering the isolated antigen-binding protein of the present application, the interaction between GITRL and its receptor GITR in the subject may be inhibited, thus restoring the functional response of T cells from a dysfunctional state to an antigen-stimulated state.

In another aspect, the present application also provides a method for activating GITR, which may comprise administering the isolated antigen-binding protein of the present application. For example, after administering the isolated antigen-binding protein of the present application, the interaction between GITRL and its receptor GITR in the subject may be blocked, thus restoring the functional response of T cells from a dysfunctional state to an antigen-stimulated state.

Without intending to be limited by any theory, the following examples are only to illustrate the isolated antigen-binding protein and the use of the present application, and are not used to limit the inventive scope of the present application.

EXAMPLES

Example 1. Preparation of Antigen Protein

According to the amino acid sequence (Q9Y5U5) of human GITR on the protein database Uniprot, whose amino acid sequence is shown in SEQ ID NO: 49, the amino acid sequence (i.e., residues 1 to 161 in Q9Y5U5) of the extracellular domain of human GITR is obtained, whose amino acid sequence is shown in SEQ ID NO: 50. According to the amino acid sequence (XP_005545180.1) of Cynomolgus monkey GITR (i.e., cynoGITR) on the database NCBI, whose amino acid sequence is shown in SEQ ID NO: 51, the amino acid sequence (i.e., residues 1 to 155 in XP_005545180.1) of the extracellular domain of Cynomolgus monkey GITR is obtained, whose amino acid sequence is shown in SEQ ID NO: 52. According to the amino acid sequence (P01857) of the heavy chain constant region of the human immunoglobulin gamma1 (IgG1) on the protein database Uniprot, whose amino acid sequence is shown in SEQ ID NO: 53, the amino acid sequence (i.e., residues 104 to 330 in P01857) of human IgG1-Fc domain is obtained, whose amino acid sequence is shown in SEQ ID NO: 54. According to the amino acid sequence (P01868) of the heavy chain constant region of the mouse immunoglobulin gamma1 (IgG1) on the protein database Uniprot, whose amino acid sequence is shown in SEQ ID NO: 56, the amino acid sequence (i.e., residues 98 to 324 in P01868) of the mouse IgG1-Fc (muFc) domain is obtained, whose amino acid sequence is shown in SEQ ID NO: 57. A DNAworks online tool (helixweb.nih.gov/dnaworks/) was utilized to design the corresponding coding DNA sequences to obtain the genes of the following three fusion proteins: a fusion protein in which the extracellular domain of human GITR is fused with the domain of human IgG1-Fc (represented with hGITR-Fc, whose amino acid sequence is shown in SEQ ID NO: 58), a fusion protein in which the extracellular domain of human GITR is fused with the domain of mouse IgG1-Fc (represented with hGITR-muFc, whose amino acid sequence is shown in SEQ ID NO: 59) as well as a fusion protein in which the extracellular domain of Cynomolgus monkey GITR is fused with the domain of mouse IgG1-Fc (represented with cynoGITR-muFc, whose amino acid sequence is shown in SEQ ID NO: 60). The nucleotide sequence encoding hGITR-Fc is shown in SEQ ID NO: 65, the nucleotide sequence encoding hGITR-muFc is shown in SEQ ID NO: 66, and the nucleotide sequence encoding cynoGITR-muFc is shown in SEQ ID NO: 67.

The amino acid sequence (C5 MKY7) of enhanced green fluorescent protein (EGFP) was obtained according to the information on the protein database Uniprot. The DNAworks online tool (helixweb.nih.gov/dnaworks/) was utilized to design the corresponding coding DNA sequences to obtain the genes of the following two fusion proteins fused with EGFP, that is, the gene of a fusion protein (represented with hGITR-EGFP, whose amino acid sequence is shown in SEQ ID NO: 61) in which the extracellular domain of human GITR is fused with EGFP and the gene of a fusion protein (represented with cynoGITR-EGFP, whose amino acid sequence is shown in SEQ ID NO:62) in which the extracellular domain of Cynomolgus monkey GITR is fused with EGFP. The nucleotide sequence encoding hGITR-EGFP is shown in SEQ ID NO: 68, and the nucleotide sequence encoding cynoGITR-EGFP is shown in SEQ ID NO: 69.

The above DNA fragments were obtained by artificial synthesis. The synthesized gene sequence was subcloned into a commercial vector pcDNA4/myc-HisA (Invitrogen, V863-20) by double digestion with HindIII and PmeI of Fermentas Co., respectively. The accuracy of the constructed plasmid was verified by sequencing, and the recombinant plasmid DNAs were obtained, that were: pcDNA4-hGITR-Fc, pcDNA4-hGITR-muFc, pcDNA4-cynoGITR-muFc, pcDNA4-hGITR-EGFP, pcDNA4-cynoGITR-EGFP.

The related EGFP recombinant plasmids (i.e., pcDNA4-hGITR-EGFP and pcDNA4-cynoGITR-EGFP) were transfected into HEK293 (ATCC, CRL-1573™) cells to prepare hGITR-EGFP cells and cynoGITR-EGFP cells. 48 h after transfection, the expression of hGITR and cynoGITR was confirmed by Fluorescence-activated cell sorting (FACS).

pcDNA4-hGITR-Fc, pcDNA4-hGITR-muFc and pcDNA4-cynoGITR-muFc were transiently transfected into HEK293 cells for the production of antigen proteins. A specific method was as follows: the recombinant plasmid was diluted with Freestyle 293 medium and added with a PEI (Polyethylenimine) solution required for transformation. Each group of plasmid/PEI mixture was respectively added into a cell suspension and cultured at 37° C., 10% $CO_2$, and 90 rpm. After cultivation for 5 to 6 days, the supernatant of the transiently expressed culture was collected, and preliminarily purified through Protein A affinity chromatography to obtain hGITR-Fc, hGITR-muFc and cynoGITR-muFc antigen protein samples, which were used in the following examples. The obtained antigen protein samples were preliminarily detected by SDS-PAGE, and the target bands could be clearly observed.

Example 2. Preparation of the Isolated Antigen-Binding Protein 3E2 of the Present Application by a Method of Hybridoma The hGITR-muFc prepared in Example 1 was used to immunize mice, and the antibody titer was tested after three immunizations. Mice with high titers were selected for the fourth immunization. The spleen cells were separated from the mice after the fourth immunization, and the spleen cells were fused with myeloma cells SP2/0 of the mice. The supernatant after fusion (i.e., hybridoma supernatant) was tested for ELISA binding, totally obtaining 382 hybridoma clones which can bind to GITR. The ELISA detection method was specifically as follows: coating 2 μg/ml of hGITR-Fc on an ELISA plate at 100 μl/well, and incubating overnight at 4° C.; washing once with 10 mM of PBS/Tween (the volume fraction of Tween was 0.05%) at pH 7.4, blocking with PBS containing 3% BSA, incubating at 37° C. for 2 h; washing the plate for 3 times, then adding the hybridoma supernatant, incubating at 37° C. for 1 h, washing the plate for 3 times, adding anti-mouse IgG-HRP enzyme-labeled secondary antibody, incubating at 37° C. for 1 h, cleaning and then developing the plate with TMB substrate, performing spectrophotometric analysis at OD450 nm, and selecting clones with OD>0.8 to be judged as positive.

The obtained positive clones were subjected to FACS binding detection and activating activity detection, and antibodies with activating activity were selected for subsequent experiments. The FACS binding detection method was as follows: hGITR-EGFP cells prepared in Example 1 were washed twice with PBS, 50 μl hybridoma supernatant and 50 μl PBS were added and incubated at 4° C. for 30 min, washed twice with PBS, anti-mouse Ig-PE was added and incubated at 4° C. for 30 min, washed twice with PBS and resuspended in 300 μl PBS, with the results detected by flow cytometry, totally obtaining two positive clones.

Two clones with strong binding ability were selected for activating activity detection. The activating activity detection method was as follows: a 48-well plate was coated with 0.3 μg/ml of anti-CD3 (OKT3) at 150 μl/well, overnight at 4° C. The next day, the coated 48-well plate was washed twice at 500 μl/well and inoculated with Jurkat-GITR cells (purchased from promega) at $1*10^5$/well and 250 μl/well. Different concentrations of the above two cloned antibodies with strong binding ability were respectively added and stimulated by crosslinking at 250 μl/well. After 6 h, the cells were lysed and detected with a luciferase detection system (Promega: E1500), finally obtaining one monoclonal antibody, which was subcloned and the obtained monoclone (i.e., the isolated antigen-binding protein of the present application, represented with 3E2) was sequenced. The amino acid sequence of VH of 3E2 is shown in SEQ ID NO:1, and the amino acid sequence of VL is shown in SEQ ID NO: 9. The nucleotide sequence of VH encoding 3E2 is shown in SEQ ID NO: 70, and the nucleotide sequence of VL encoding 3E2 is shown in SEQ ID NO: 71.

Example 3. Preparation of the Isolated Antigen-Binding Protein C3E2 of the Present Application According to the amino acid sequence (P01857) of the constant region of human immunoglobulin gamma1 (IgG1) on the protein database Uniprot, the amino acid sequence of human IgG1 heavy chain constant region is obtained, whose amino acid sequence is shown in SEQ ID NO: 53. A DNAworks online tool (http://helixweb.nih.gov/dnaworks/) was utilized to design the corresponding coding DNA sequences to obtain the gene of the human IgG1 heavy chain constant region. The VH sequence of the heavy chain variable region of the 3E2 protein screened in Example 2 was spliced together with the gene sequence of the human IgG1 heavy chain constant region to synthesize a spliced gene, which was subcloned into the vector pcDNA4/myc-HisA by double digestion with HindIII and PmeI of Fermentas Co. to get the heavy chain expression plasmid of the antibody.

According to the amino acid sequence (P01934) of the constant region of human immunoglobulin Kappa on the protein database Uniprot, the amino acid sequence of human immunoglobulin Kappa light chain constant region is obtained, whose amino acid sequence is shown in SEQ ID NO: 55. A DNAworks online tool (http://helixweb.nih.gov/dnaworks/) was utilized to design the corresponding coding DNA sequences to obtain the gene of the human Kappa light chain constant region. The VL sequence of the light chain variable region of the 3E2 protein screened in Example 2 was spliced together with the gene sequence of the human Kappa light chain constant region to synthesize a spliced gene, which was subcloned into the vector pcDNA4/myc-HisA by double digestion with HindIII and PmeI of Fermentas Co. to get the light chain expression plasmid of the antibody.

The heavy chain and light chain expression plasmids obtained above were subjected to large-scale plasmid extraction by using the plasmid maxi kit (PL14) provided by AidLab Co. The recombinantly constructed light chain and heavy chain plasmids were co-transfected into HEK293 cells for antibody expression. The recombinantly expressed plasmids were diluted with Freestyle 293 medium and added with a PEI (Polyethylenimine) solution required for transformation. Each group of plasmid/PEI mixture was respectively added into a cell suspension and cultured at 37° C., 10% $CO_2$, and 90 rpm; meanwhile, 50 μg/L of IGF-1 was supplemented. Four hours later, EX293 medium, 2 mM Glutamine and 50 μg/L of IGF-1 were further supplemented and cultured at 135 rpm. 24 hours later, 3.8 mM of VPA was added. After cultivation for 5 to 6 days, the supernatant of the transiently expressed culture was collected, and purified through Protein A affinity chromatography to get the isolated antigen-binding protein of the present application (represented by C3E2, its heavy chain amino acid sequence is shown in SEQ ID NO: 63, and its light chain amino acid sequence is shown in SEQ ID NO: 64), the expression amount of which was 42.5 µg/ml.

Example 4. Characterization of the Isolated Antigen-Binding Protein C3E2 of the Present Application 4.1. Detection of the Ability of Binding to GITR on the Cell Surface (FACS)

hGITR-EGFP cells and cynoGITR-EGFP cells prepared in Example 1 were taken and washed twice with PBS, 10 µg/ml of C3E2 was added and incubated at 4° C. for 30 min, washed twice with PBS, anti-human Ig-PE was added and incubated at 4° C. for 30 min, washed twice with PBS, resuspended in 300 µl of PBS, and detected by flow cytometry, with the results shown in FIG. 1. Where, FIG. 1A-FIG. 1D respectively shows the profiles of negative control (addition of only PBS), anti-human Ig-PE, C3E2-bound hGITR (human GITR), C3E2-bound cynoGITR (monkey GITR).

It can be seen from FIG. 1 that, the isolated antigen-binding protein C3E2 of the present application may bind to human and monkey GITR on the cell surface.

4.2. Detection of the Activating Activity

A 48-well plate was coated with 0.3 µg/ml of anti-CD3 (OKT3) at $10^5$ µl/well, overnight at 4° C. The next day, the coated 48-well plate was washed twice at 500 µl/well and inoculated with Jurkat-GITR cells (promega) at $10^5$ µl/well and 250 µl/well. Different concentrations of C3E2 was respectively added for stimulation by crosslinking at 250 µl/well. After 6 h, the cells were lysed and detected with a luciferase detection system (Promega: E6110), with the results shown in FIG. 2.

It can be seen from FIG. 2 that, the EC50 value of the isolated antigen-binding protein C3E2 of the present appli- Tianjin Haoyang). The PBMCs were separated by EasySep Negative Human CD4 Kit (Stem cells: 19052) to get CD4$^+$ T cells, which were washed twice with PBS, counted and added into a 96-well plate at $1.5*10^5$ cells per well. The 96-well plate was pre-coated with 0.2 µg/ml of anti-CD3 antibody and C3E2, and incubated at 37° C. for 2 h, into which was added 0.2 µg/ml of CD28. For the negative control, only anti-CD3 antibody or IgG was added. The next day, the plate was washed with PBS for 3 times. After adding CD4+ T cells into the 96-well plate, the 96-well plate was cultured in a carbon dioxide incubator for 3 d and then the cells were collected, of which the proliferation was detected by flow cytometry, and the supernatant was collected to detect the changes of cytokines. The results are shown in FIG. 3 and FIG. 4. The negative control in the figure means that only anti-CD3 antibody was added. It can be seen from FIG. 3 and FIG. 4 that, the isolated antigen-binding protein C3E2 of the present application is capable of stimulating T cell proliferation and promoting the increase of the content of cytokine IFN-7.

Example 5. Preparation and Characterization of the Isolated Antigen-Binding Proteins 3E2 1-2, 3E2 1-3, 3E2 1-4, 3E2 2-2, 3E2 2-3, 3E2 2-4, 3E2 3-2, 3E2 3-3 and 3E2 3-4 of the Present Application 5.1. Preparation of the Isolated Antigen-Binding Protein of the Present Application 3E2 prepared in Example 2 was used for humanization. The antibodies were humanized by changing some amino acid residues of the framework regions of heavy chain and light chain variable regions, totally obtaining 9 humanized antibodies as shown in Table 1, which were the 9 isolated antigen-binding proteins of the present application, represented by 3E2 1-2, 3E2 1-3, 3E2 1-4, 3E2 2-2, 3E2 2-3, 3E2 2-4, 3E2 3-2, 3E2 3-3 and 3E2 3-4, respectively.

TABLE 1

| | | | | | | | Nucleotide SEQ ID NO encoding heavy chain variable region | Nucleotide SEQ ID NO encoding light chain variable region |
|---|---|---|---|---|---|---|---|---|
| | Heavy chain variable region | | Light chain variable region | | SEQ ID | SEQ ID NO | | |
| Humanized antibody | Humanized VH | SEQ ID NO | Humanized VL | SEQ ID NO | NO of heavy chain | of light chain | | |
| 3E2 1-2 | VHV1 | 17 | VLV2 | 20 | 43 | 46 | 72 | 75 |
| 3E2 1-3 | VHV1 | 17 | VLV3 | 21 | 43 | 47 | 72 | 76 |
| 3E2 1-4 | VHV1 | 17 | VLV4 | 22 | 43 | 48 | 72 | 77 |
| 3E2 2-2 | VHV2 | 18 | VLV2 | 20 | 44 | 46 | 73 | 75 |
| 3E2 2-3 | VHV2 | 18 | VLV3 | 21 | 44 | 47 | 73 | 76 |
| 3E2 2-4 | VHV2 | 18 | VLV4 | 22 | 44 | 48 | 73 | 77 |
| 3E2 3-2 | VHV3 | 19 | VLV2 | 20 | 45 | 46 | 74 | 75 |
| 3E2 3-3 | VHV3 | 19 | VLV3 | 21 | 45 | 47 | 74 | 76 |
| 3E2 3-4 | VHV3 | 19 | VLV4 | 22 | 45 | 48 | 74 | 77 |

Sequences of heavy chain and light chain of the 9 humanized antibodies cation is 0.5063, and the isolated antigen-binding protein C3E2 of the present application is capable of activating downstream NFκB signals, having a good activating activity.

4.3. Detection of the Activity to Activate T Cells

Peripheral blood mononuclear cells PBMCs were separated from concentrated leukocytes in peripheral blood of healthy donors by means of density gradient centrifugation of human lymphocyte separation solution (purchased from The above humanized VH gene and VL gene were synthesized. And according to the construction method of C3E2 in Example 3, VH and human IgG1 heavy chain constant region constitute the heavy chain of the antibody, VL and human kappa light chain constant region constitute the light chain of the antibody. Each gene was cloned into the vector of pcDNA4/myc-HisA to obtain heavy chain expression plasmids and light chain expression plasmids. The heavy chain expression plasmids and light chain expression plasmids were respectively paired according to Table 1 and then transiently transfected into HEK293 (ATCC, CRL-1573™) cell lines for the production of proteins. The recombinantly expressed plasmids were diluted with Freestyle 293 medium and added with a PEI (Polyethylenimine) solution required for transformation. Each group of plasmid/PEI mixture was respectively added into a cell suspension and cultured at 37° C., 10% $CO_2$, and 90 rpm. After cultivation for 5 to 6 days, the supernatant of the transiently expressed culture was collected, and preliminarily purified through Protein A affinity chromatography to obtain the 9 isolated antigen-binding proteins of the present application, i.e., 3E2 1-2, 3E2 1-3, 3E2 1-4, 3E2 2-2, 3E2 2-3, 3E2 2-4, 3E2 3-2, 3E2 3-3 and 3E2 3-4, which were used in the following examples. The obtained protein samples were preliminarily detected by SDS-PAGE, and the target bands could be clearly observed. The expression amounts of the above 9 isolated antigen-binding proteins of the present application were shown in Table 2.

TABLE 2

Expression amounts of the 9 isolated antigen-binding
proteins of the present application

| Name | Expression amount (μg/ml) |
|---|---|
| 3E2 3-2 | 19.4 |
| 3E2 3-3 | 48 |
| 3E2 3-4 | 37.1 |
| 3E2 2-2 | 18.4 |
| 3E2 2-3 | 61.4 |
| 3E2 2-4 | 57.1 |
| 3E2 1-2 | 35.9 |
| 3E2 1-3 | 78.7 |
| 3E2 1-4 | 91 |

5.2. Detection of the Ability of the Isolated Antigen-Binding Protein of the Present Application Binding to Human GITR Protein (ELISA)

An ELISA plate was coated with 5 μg/ml of hGITR-muFc at 100 μl/well, and incubated overnight at 4° C. The plate was washed with 10 mM of PBS/Tween (0.05%) at pH 7.4 for 3 times, blocked with PBS containing 3% BSA and incubated at 37° C. for 2 h; then washed for 3 times, added with the above 9 isolated antigen-binding proteins of the present application in 3-fold dilutions starting from 10 μg/ml, incubated at 37° C. for 2 h, washed for 3 times, added with anti-human IgG-HRP enzyme-labeled secondary antibody, incubated at 37° C. for 1 h, cleaned, then developed with TMB substrate, and subjected to spectrophotometric analysis at OD450 nm. The results are shown in FIG. 5 and FIG. 6, in which the $EC_{50}$ values of various proteins in FIG. 5 and FIG. 6 are shown in Table 3 and Table 4, respectively. It can be seen from FIG. 5 and FIG. 6 as well as Table 3 and Table 4 that, the humanized antibodies (i.e., the isolated antigen-binding proteins of the present application 3E2 1-2, 3E2 1-3, 3E2 1-4, 3E2 2-2, 3E2 2-3, 3E2 2-4, 3E2 3-2, 3E2 3-3 and 3E2 3-4) have a binding affinity to the antigen that is equivalent to that of the parent antibody (i.e., the isolated antigen-binding protein C3E2 of the present application).

TABLE 3

$EC_{50}$ values of various proteins in FIG. 5

| Name | Human GITR $EC_{50}$ (ng/ml) |
|---|---|
| C3E2 | 6.212 |
| 3E2 1-2 | 5.899 |
| 3E2 1-3 | 5.832 |

TABLE 3-continued $EC_{50}$ values of various proteins in FIG. 5

| Name | Human GITR $EC_{50}$ (ng/ml) |
|---|---|
| 3E2 1-4 | 4.517 |
| 3E2 2-2 | 5.644 |

TABLE 4

$EC_{50}$ values of various proteins in FIG. 6

| Name | Human GITR $EC_{50}$ (ng/ml) |
|---|---|
| C3E2 | 6.721 |
| 3E2 2-3 | 4.711 |
| 3E2 2-4 | 4.800 |
| 3E2 3-2 | 5.275 |
| 3E2 3-3 | 6.041 |
| 3E2 3-4 | 6.435 |

5.3. Detection of the Ability of the Isolated Antigen-Binding Protein of the Present Application to Bind to Monkey GITR Protein (ELISA)

An ELISA plate was coated with 5 μg/ml of cynoGITR-muFc prepared in Example 1 at 100 μl/well, and incubated overnight at 4° C. The plate was washed with 10 mM of PBS/Tween (0.05%) at pH 7.4 for 3 times, blocked with PBS containing 3% BSA and incubated at 37° C. for 2 h; then washed for 3 times, added with the above 9 isolated antigen-binding proteins of the present application in 3-fold dilutions starting from 10 μg/ml as well as C3E2, incubated at 37° C. for 2 h, washed for 3 times, added with anti-human IgG-HRP enzyme-labeled secondary antibody, incubated at 37° C. for 1 h, cleaned, then developed with TMB substrate, and subjected to spectrophotometric analysis at OD450 nm.

The results are shown in FIG. 7 and FIG. 8, in which the $EC_{50}$ values of various proteins in FIG. 7 and FIG. 8 are shown in Table 5 and Table 6, respectively. It can be seen from FIG. 7 and FIG. 8 as well as Table 5 and Table 6 that, the binding affinity of the humanized antibodies (i.e., the isolated antigen-binding proteins of the present application 3E2 1-2, 3E2 1-3, 3E2 1-4, 3E2 2-2, 3E2 2-3, 3E2 2-4, 3E2 3-2, 3E2 3-3 and 3E2 3-4) to the antigen of monkey is improved compared to that of the parent antibody (i.e., the isolated antigen-binding protein C3E2 of the present application).

TABLE 5

$EC_{50}$ values of various proteins in FIG. 7

| Name | Monkey GITR $EC_{50}$ (ng/ml) |
|---|---|
| C3E2 | 70.39 |
| 3E2 1-2 | 51.65 |
| 3E2 1-3 | 51.70 |
| 3E2 1-4 | 54.89 |
| 3E2 2-2 | 64.02 |

TABLE 6

$EC_{50}$ values of various proteins in FIG. 8

| Name | Monkey GITR $EC_{50}$ (ng/ml) |
|---|---|
| C3E2 | 74.74 |
| 3E2 2-3 | 51.05 |

TABLE 6-continued

| EC$_{50}$ values of various proteins in FIG. 8 | |
| --- | --- |
| Name | Monkey GITR EC$_{50}$ (ng/ml) |
| 3E2 2-4 | 54.58 |
| 3E2 3-2 | 48.93 |
| 3E2 3-3 | 52.51 |
| 3E2 3-4 | 53.17 |

5.4. Detection of the Binding Kinetics Between the Isolated Antigen-Binding Protein of the Present Application and Human GITR Protein Using the BLI method, the above 9 isolated antigen-binding proteins of the present application and C3E2 were immobilized on the AHC biosensor at a concentration of 10 g/ml. At the same time, the hGITR-muFc prepared in Example 1 was diluted 2-fold from 100 nM in 5 gradients. The reaction plate was placed on Octet K2 instrument, meanwhile the program was set as Baseline 60 s, Association 20 s, Dissociation 300 s, Baseline 2 30 s, Loading 40 s, custom 5 s. At the end of the program, curve fitting and parameter conversion were conducted. The results are shown in Table 7, from which it can be seen that the KD value of the above 9 isolated antigen-binding proteins of the present application may be $7 \times 10^{-12}$ or less.

TABLE 7

Detection results of the binding kinetics of the isolated antigen-binding protein of the present application to human GITR protein

| Sample Name | KD (M) | Kon (1/Ms) | Koff (1/s) | X$^2$ | R$^2$ |
| --- | --- | --- | --- | --- | --- |
| C3E2 | $6.01 \times 10^{-12}$ | $3.05 \times 10^{6}$ | $1.83 \times 10^{-5}$ | 0.0224 | 0.9978 |
| 3E2 1-2 | $<1.0 \times 10^{-12}$ | $2.49 \times 10^{6}$ | $<1.0 \times 10^{-7}$ | 0.0224 | 0.9974 |
| 3E2 1-3 | $<1.0 \times 10^{-12}$ | $2.32 \times 10^{6}$ | $<1.0 \times 10^{-7}$ | 0.0255 | 0.9967 |
| 3E2 1-4 | $<1.0 \times 10^{-12}$ | $2.55 \times 10^{6}$ | $<1.0 \times 10^{-7}$ | 0.0238 | 0.9969 |
| 3E2 2-2 | $1.25 \times 10^{-11}$ | $2.40 \times 10^{6}$ | $3.01 \times 10^{-5}$ | 0.0068 | 0.9989 |
| 3E2 2-3 | $<1.0 \times 10^{-12}$ | $2,46 \times 10^{6}$ | $<1.0 \times 10^{-7}$ | 0.0128 | 0.9981 |
| 3E2 2-4 | $<1.0 \times 10^{-12}$ | $2.41 \times 10^{6}$ | $<1.0 \times 10^{-7}$ | 0.0152 | 0.9976 |
| 3E2 3-2 | $<1.0 \times 10^{-12}$ | $2.52 \times 10^{6}$ | $<1.0 \times 10^{-7}$ | 0.0134 | 0.9976 |
| 3E2 3-3 | $<1.0 \times 10^{-12}$ | $2.49 \times 10^{6}$ | $<1.0 \times 10^{-7}$ | 0.0112 | 0.9978 |
| 3E2 3-4 | $4.72 \times 10^{-12}$ | $2.60 \times 10^{6}$ | $1.23 \times 10^{-5}$ | 0.0107 | 0.998 |

5.5. Detection of the Activating Activity of the Isolated Antigen-Binding Protein of the Present Application (Luciferase Reporter Gene Method)

Jurkat-GITR-NF-kB stable cell lines were digested for 2-3 min by adding trypsin, and then a DMEM complete medium was added to terminate the digestion. The cells were blown gently and the cell suspension was transferred and inoculated into a 96-well plate at 100 μl/well. The above 9 isolated antigen-binding proteins of the present application and C3E2 were diluted 10-fold starting from 10 μg/ml. The diluted antibodies were mixed with anti-human crosslinking antibody (Jackson Immuno Research Laboratories: 109-006-008) and added into the 96-well plate. A complete medium was added into the control group. The cells were lysed after 6 h, and detected with a luciferase detection system (Promega: E6110), with the results shown in FIG. 9.

It can be seen from FIG. 9 that the ability of the above 9 isolated antigen-binding proteins of the present application to activate downstream signaling pathways has not changed, thus demonstrating that the activating activity of the humanized antibodies (i.e., the isolated antigen-binding proteins of the present application: 3E2 1-2, 3E2 1-3, 3E2 1-4, 3E2 2-2, 3E2 2-3, 3E2 2-4, 3E2 3-2, 3E2 3-3 and 3E2 3-4) is equivalent to that of the parent antibody (i.e., the isolated antigen-binding protein C3E2 of the present application), and the above 9 isolated antigen-binding proteins of the present application are activating antibodies.

5.6. Detection of the Activity of the Isolated Antigen-Binding Protein of the Present Application to Activate T Cells Peripheral blood mononuclear cells PBMCs were separated from concentrated leukocytes in peripheral blood of healthy donors by means of density gradient centrifugation of human lymphocyte separation solution (purchased from Tianjin Haoyang). The PBMCs were separated by Easy Sep Negative Human CD4 Kit (Stem cells: 19052) to get CD4$^+$ T cells, which were washed twice with PBS, counted and added into a 96-well plate at $1.5 \times 10^5$ cells per well. The 96-well plate was pre-coated with 0.2 μg/ml of anti-CD3 antibody and chimeric antibody, and incubated at 37° C. for 2 h, into which was added 0.2 μg/ml of CD28. For the negative control, only anti-CD3 antibody and IgG were added. For the positive control, soluble anti-CD28 antibodies were added (together with cells on the next day). The next day, the plate was washed with PBS for 3 times. After adding CD4+ T cells into the 96-well plate, the 96-well plate was cultured in a carbon dioxide incubator for 4 d and then the cells were collected, of which the proliferation was detected by flow cytometry, and meanwhile the supernatant was collected to detect the changes of IFN-γ. The results are shown in FIG. 10 and FIG. 11. The control group in the figure indicates the above negative control. It can be seen that the isolated antigen-binding proteins of the present application, 3E2 1-2, 3E2 1-4, 3E2 1-3 and 3E2 2-3, are all capable of stimulating T cell proliferation, and capable of increasing the secretion of IFN-7, thus having a good activating activity.

5.7. Detection of the Stability of the Isolated Antigen-Binding Protein of the Present Application (Differential Scanning Calorimetry, DSC)

The thermal stability of the isolated antigen-binding protein of the present application was detected by using the DSC method. In order to complete the test correctly by DSC, the scanning results of a separate buffer and a buffer with protein were collected. The isolated antigen-binding protein of the present application was diluted to 1 mg/ml (PBS buffer). The conditions for collecting data were: the DSC was set to scanning at 10-110° C., the scanning speed was 100° C. per hour, and there was 15 min of equilibrium before each scanning. The submission of the DSC sample room was 0.5 ml. After collecting the scanning results of the buffer and protein, the scanning results of the buffer can be subtracted from the scanning results of the protein to obtain the concentration of protein in the sample, thereby obtaining the Tm value of the isolated antigen-binding protein of the present application, with the results shown in FIG. 12, FIG. 13 and FIG. 14, from which it can be seen from that, the Tm of 3E2 1-3, 3E2 1-4 and 3E2 2-3 are all above 80° C., showing excellent stability.

5.8. Detection of the Stability of the Isolated Antigen-Binding Protein of the Present Application by an Accelerated Stabilization Experiment at 45° C.

An accelerated stabilization experiment at 45° C. was performed on the isolated antigen-binding protein of the present application, which was specifically: the isolated antigen-binding protein of the present application that had been purified in one step through protein A was dissolved in PBS (pH 7.4), and the protein was concentrated to 2 mg/ml. 100 μg of the concentrated protein was charged into a 200 μl PCR tube and placed in a water bath at 45° C. Samples were collected on days 0, 7, and 14 for SDS-PAGE detection and SEC-HPLC analysis, with the results shown in FIG. 15-FIG. 20 (FIGS. 15-17 show the SDS-PAGE of 3E2 1-3, 3E2 1-4 and 3E2 2-3, respectively, and FIGS. 18-20 show the SEC-HPLC of 3E2 1-3, 3E2 1-4 and 3E2 2-3, respectively), and the isolated antigen-binding proteins of the present application, 3E2 1-3, 3E2 1-4 and 3E2 2-3, at a concentration of 2 mg/ml were very stable at the condition of 45° C.

The foregoing detailed description is provided by way of explanation and examples, and is not intended to limit the scope of the appended claims. Various changes of the embodiments currently listed in the present application are obvious to those of ordinary skills in the art, and are reserved within the scope of the appended claims and their equivalents.

What is claimed is:

1. An isolated antigen-binding protein, having one or more of the following properties:
   1) Capable of binding to human and monkey-derived GITR proteins at a $K_D$ value of $7 \times 10^{-12}$ M or below, wherein the $K_D$ value is measured by Bio-Layer Interferometry (BLI) method;
   2) capable of stimulating immune cell proliferation;
   3) capable of stimulating immune cells to secrete IFN-γ, wherein the secretion is measured in T cell viability assay;
   4) capable of inhibiting tumor growth and/or tumor cell proliferation;
   5) capable of activating GITR signaling pathway;
   6) capable of inhibiting the binding of GITR to GITRL, wherein VH of the isolated antigen-binding protein comprises HCDR3 as set forth in SEQ ID NO: 4, HCDR1 as set forth in SEQ ID NO: 2, and HCDR2 as set forth in SEQ ID NO: 3, and
   wherein VL of the isolated antigen-binding protein comprises LCDR1 as set forth in SEQ ID NO: 10, LCDR2 as set forth in SEQ ID NO: 11, and LCDR3 as set forth in SEQ ID NO: 12.

2. The isolated antigen-binding protein according to claim 1, wherein the VL comprises framework regions L-FR1, L-FR2, L-FR3, and L-FR4, wherein a C-terminus of the L-FR1 is directly or indirectly linked to an N-terminus of the LCDR1, wherein the L-FR1 comprises an amino acid sequence as shown in any one of SEQ ID NOs: 13, 30, 34.

3. The isolated antigen-binding protein according to claim 2, wherein the L-FR2 is located between the LCDR1 and the LCDR2, and the L-FR2 comprises an amino acid sequence as shown in any one of SEQ ID NOs: 14, 31.

4. The isolated antigen-binding protein according to claim 2, wherein the L-FR3 is located between the LCDR2 and the LCDR3, and the L-FR3 comprises an amino acid sequence as shown in any one of SEQ ID NOs: 15, 32.

5. The isolated antigen-binding protein according to claim 2, wherein an N-terminus of the L-FR4 is linked to a C-terminus of the LCDR3, and the L-FR4 comprises an amino acid sequence as shown in any one of SEQ ID NOs: 16, 33.

6. The isolated antigen-binding protein according to claim 1, wherein the VL comprises an amino acid sequence as shown in any one of SEQ ID NOs: 9, 20-22.

7. The isolated antigen-binding protein according to claim 1, comprising an antibody light chain constant region, and the antibody light chain constant region comprises a human Igκ constant region.

8. The isolated antigen-binding protein according to claim 1, comprising an antibody light chain LC, and the LC comprises an amino acid sequence as shown in any one of SEQ ID NOs: 64, 46-48.

9. The isolated antigen-binding protein according to claim 1, wherein the VH comprises framework regions H-FR1, H-FR2, H-FR3, and H-FR4, a C-terminus of the H-FR1 is directly or indirectly linked to an N-terminus of the HCDR1, and wherein the H-FR1 comprises an amino acid sequence as shown in any one of SEQ ID NOs: 5, 25, 29.

10. The isolated antigen-binding protein according to claim 9, wherein the H-FR2 is located between the HCDR1 and the HCDR2, and the H-FR2 comprises an amino acid sequence as shown in any one of SEQ ID NOs: 6, 26.

11. The isolated antigen-binding protein according to claim 9, wherein the H-FR3 is located between the HCDR2 and the HCDR3, and the H-FR3 comprises an amino acid sequence as shown in any one of SEQ ID NOs: 7, 27.

12. The isolated antigen-binding protein according to claim 9, wherein an N-terminus of the H-FR4 is linked to a C-terminus of the HCDR3, and the H-FR4 comprises an amino acid sequence as shown in any one of SEQ ID NOs: 8, 28.

13. The isolated antigen-binding protein according to claim 1, wherein the VH comprises an amino acid sequence as shown in any one of SEQ ID NOs: 1, 17-19.

14. The isolated antigen-binding protein according to claim 1, comprising an antibody heavy chain constant region, and the antibody heavy chain constant region is derived from a human IgG1 heavy chain constant region.

15. The isolated antigen-binding protein according to claim 1, comprising an antibody heavy chain HC, and the HC comprises an amino acid sequence as shown in any one of SEQ ID NOs: 63, 43-45.

16. A pharmaceutical composition, comprising the isolated antigen-binding protein according to claim 1, as well as optionally a pharmaceutically acceptable adjuvant.

17. A method for activating GITR, comprising administering the isolated antigen-binding protein according to claim 1.

* * * * *